United States Patent [19]

Barnett et al.

[11] Patent Number: 6,013,772
[45] Date of Patent: Jan. 11, 2000

[54] ANTIBODY PREPARATIONS SPECIFICALLY BINDING TO UNIQUE DETERMINANTS OF CEA ANTIGENS OR FRAGMENTS THEREOF AND USE OF THE ANTIBODY PREPARATIONS IN IMMUNOASSAYS

[75] Inventors: Thomas R. Barnett, East Haven, Conn.; James J. Elting, Madison, Conn.; Michael E. Kamarck, Bethany, Conn.; Axel W. Kretschmer, Wulfrath, Germany

[73] Assignee: Bayer Corporation, Tarrytown, N.Y.

[21] Appl. No.: 08/468,856

[22] Filed: Jun. 6, 1995

Related U.S. Application Data

[62] Division of application No. 08/027,974, Mar. 8, 1993, which is a division of application No. 07/760,031, Sep. 13, 1992, Pat. No. 5,231,009, which is a division of application No. 07/274,107, Nov. 21, 1988, Pat. No. 5,122,599, which is a continuation-in-part of application No. 07/207,678, Jun. 16, 1988, abandoned, which is a continuation-in-part of application No. 07/060,031, Jun. 19, 1987, abandoned, which is a continuation-in-part of application No. 07/016,683, Feb. 19, 1987, abandoned, which is a continuation-in-part of application No. 06/896,361, Aug. 13, 1986, abandoned.

[51] Int. Cl.$^7$ .......................... C07K 16/30; G01N 33/53
[52] U.S. Cl. ..................... 530/387.7; 530/387.9; 530/388.8; 530/388.85; 530/389.7; 435/7.1; 435/7.23
[58] Field of Search .............................. 530/387.7, 387.9, 530/389.7, 391.3, 388.8, 388.85; 435/7.1, 7.23; 424/138.1, 139.1, 141.1, 155.1, 156.1, 178.1

[56] References Cited

U.S. PATENT DOCUMENTS

| | | |
|---|---|---|
| 3,663,684 | 5/1972 | Orkin et al. . |
| 3,697,638 | 10/1972 | Hansen . |
| 3,852,415 | 12/1974 | Vandervoorde . |
| 3,867,363 | 2/1975 | Hansen . |
| 3,927,193 | 12/1975 | Hansen et al. . |
| 3,956,258 | 5/1976 | Hansen . |
| 4,086,217 | 4/1978 | Hansen . |
| 4,140,753 | 2/1979 | Edington et al. . |
| 4,145,336 | 3/1979 | Edington et al. . |
| 4,180,499 | 12/1979 | Hansen . |
| 4,228,236 | 10/1980 | Jakstys et al. . |
| 4,272,504 | 6/1981 | Kim et al. . |
| 4,299,815 | 11/1981 | Hansen et al. . |
| 4,349,528 | 9/1982 | Koprowski et al. . |
| 4,467,031 | 8/1984 | Gallati et al. . |
| 4,489,167 | 12/1984 | Ochi et al. . |
| 4,578,349 | 3/1986 | Schaffel . |

FOREIGN PATENT DOCUMENTS

| | | |
|---|---|---|
| 92223 | 4/1983 | European Pat. Off. . |
| 92225 | 10/1983 | European Pat. Off. . |
| 98162 | 1/1984 | European Pat. Off. . |
| 102008 | 3/1984 | European Pat. Off. . |
| 97373 | 4/1984 | European Pat. Off. . |
| 113072 | 7/1984 | European Pat. Off. . |
| 8402983 | 8/1984 | WIPO . |

OTHER PUBLICATIONS

Springer–Verlag, Practical Methods in Molecular Biology, pp. 145–146 (1981).
Barnett, J. Cell Biology 108:267–276, 1989.
Kuroki, Molecular Immunology 19:399–406, 1982.
Shiveley & Beatty, CRC Critical Rev. Oncology/Hematology 2:355–399 1985.
Rogers, et al. (1983), Biochim. Biophys. Acta vol. 695, pp. 227–249.
Sapporo Igaku Zasshi, vol. 55, No. 2, pp. 79–91 (1986), "Studies of DNA Methylation and Gene Expression".
J.E. Shively, et al., Chemical Abstracts, vol. 101, No. 21, 19th, Nov. 1984, p. 189, abstract No. 185160x, Columbus, Ohio, US; "Structural studies on carcinoembryonic antigen: molecular cloning o carcinoembryonic antigen using mixed synthetic oligonucleotide probes", & Prog. Cancer Res. Ther. 1984, 29 (Markers Colonic Cell Differ), 147–57.
Shively, et al., Prog. Cancer Res. Therapy, vol. 29, pp. 147–157, (1984).
Suggs, et al. (1981), Proceedings of the National Academy of Sciences of the USA, vol. 78, pp. 6613–6617.
Tawaragi, et al., Biochem. Biophys. Res. Comm., vol. 150, No. 1, pp. 89–96, (1988).
J.A. Thompson, et al., Proceedings of the National Academy of Sciences of the USA, vol. 84, No. 9, May 1987, pp. 2965–2969; "Molecular cloning of a gene belonging to the carcinoembryonic antigen gene family and discussion of a domain model".
Young, et al., Proceedings of the National Academy of Sciences of the USA, vol. 80, pp. 1194–1198, (1983).
W. Zimmermann, et al. Proceedings of the National Academy of Sciences of the USA, vol. 84, No. 9, May 1987, pp. 2960–2964; "Isolation and characterization of cDNA clones encoding the human carcinoembryonic antigen reveals a highly conserved repeating structure".
W. Zimmermann, et al., Chemical Abstracts, vol. 100, No. 23, Jun. 4, 1984, p. 216, abstract No. 187487n, Columbus, Ohio, US; "Characterization of messenger RNA specific for carcinoembryonic antigen", & Ann. NY. Y. Acad. Sci. 1983, 417 (Oncodev. Biol. Med.), 21–30.

(List continued on next page.)

*Primary Examiner*—Toni R. Scheiner
*Assistant Examiner*—Nancy A. Johnson
*Attorney, Agent, or Firm*—Sprung Kramer Schaefer & Briscoe

[57] ABSTRACT

A nucleic acid comprising a base sequence which codes for a CEA family member peptide sequence or nucleic acids having a base sequence hybridizable therewith, replicable recombinant cloning vehicles having an insert comprising such nucleic acid, cells transfected, infected or injected with such cloning vehicles, polypeptides expressed by such cells, synthetic peptides derived from the coding sequence of CEA family member nucleic acids, antibody preparations specific for such polypeptides, immunoassays for detecting CEA family members using such antibody preparations and nucleic acid hybridization methods for detecting CEA family member nucleic acid sequences using a nucleic acid probe comprising the above described nucleic acid.

2 Claims, 1 Drawing Sheet

OTHER PUBLICATIONS

Zimmerman, et al., Annals. New York Academy of Sciences, pp. 21–30 (1983).

Paxton, et al.; Proceedings of National Academy of Sciences, vol. 84, pp. 920–924, (1987).

Beauchemin, et al., Mol. Cell Biol., vol. 7, No. 9, pp. 3221–3230, (1987).

Cabilly, et al., Proceedings of the National Academy of Sciences of the USA, vol. 81, (1984), pp. 3273–3277.

Engvall, et al., Proceedings of the National Academy of Sciences of the USA, vol. 75 1978, pp. 1670–1674, Isolation and characterization of the normal crossreacting antigen: Homology of its $NH_2$ –terminal amino acid sequence with that of carcinoembryonic antigen.

Engvall, et al., Proceedings of the National Academy of Sciences of the USA, vol. 75, (1978), pp. 1170–1174.

Glassman, et al. (1978), Biochem. Biophys. Res. Com., vol. 85, pp. 209–216.

Gold and Freedman, J. Exp. Med., vol. 121, pp. 439–462, (1965).

Harlow, et al. Mol. and Cell Biol. (1985), vol. 5, No. 7, pp. 1601–1610, "Molecular Cloning and In Vitro Expression of a cDNA Clone for Human Cellular Tumor Antigen p. 53".

Harlow, et al., Mol. and Cell Biol., vol. 5, No. 7, pp. 1001–1010, (1985).

T. Higashide, et al. CA107 100h (1987), "Preparation of the CEA mRNA for CEA gene cloning".

T. Higashide, Chemical Abstracts, vol. 105, No. 7, Aug. 17, 1986, p. 162, abstract No. 55557d, Columbus, Ohio, US;"Studies on DNA methylation and gene expression. With special reference to the onocodevelopmental protein genes", & Sapporo Igaku Zasshi 1986, 55 (2), 79–91.

T. Higashide, Igaku NoArjumi, vol. 140, pp. 827–828, (1987).

M.E. Kamarck, et al., Proceedings of the National Academy of Sciences of the USA, vol. 84, No. 16, Aug. 1987, pp. 5350–5354; "Carcinoembryonic antigen family; Expression in a mouse L–cell transfectant and characterization of a partial cDNA in bacteriophage lambdagt 11".

Larhammer, et al., Proceedings of the National Academy of Sciences of the USA, vol. 82,, pp. 1475–1479, (1985).

T. Maniatis, Molecular Cloning, A Laboratory Manual, Cold Spring Harbor, 1982, pp. 387–388.

Neumaier, et al., J. Biol. Chem., vol. 263, pp. 3202–3207, (1988).

Oikawa, et al., Biochem. Biophys. Res. Comm., vol. 142, No. 2, pp. 511–518, (1978).

Oikawa, et al., Biochem. Biophys. Res. Comm., vol. 144, No. 2, pp. 634–642, (1987).

Oikawa, et al., Biochem. Biophys. Res. Comm., vol. 146, No. 2, pp. 464–469, (1987).

Paxton, et al. (1985), Abst. Int., Soc. Oncodev. Biol. Med., p. 47.

6,013,772

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 3173 nucleotides
        (B) TYPE: nucleic acid
        (C) STRANDEDNESS: single
        (D) TOPOLOGY: linear (xi) SEQUENCE DESCRIPTION: SEQ ID NO: 1:

```
CAGCCGTGCT CGAAGCGTTC CTGGAGCCCA AGCTGTCCTC                    40

CACAGGTGAA GACAGGGCCA GCAGGAGACA CC ATG GGC                    78
                                    Met Gly

CAC CTC TCA GCC CCA CTT CAC AGA GTG CGT GTA CCC TGG           117
His Leu Ser Ala Pro Leu His Arg Val Arg Val Pro Trp
        5               10                  15

CAG GGG CTT CTG CTC ACA GCC TCA CTT CTA ACC TTC TGG           156
Gln Gly Leu Leu Leu Thr Ala Ser Leu Leu Thr Phe Trp
            20                  25

AAC CCG CCC ACC ACT GCC CAG CTC ACT ACT GAA TCC ATG           195
Asn Pro Pro Thr Thr Ala Gln Leu Thr Thr Glu Ser Met
        30                  35                  40

CCA TTC AAT GTT GCA GAG GGG AAG GAG GTT CTT CTC CTT           234
Pro Phe Asn Val Ala Glu Gly Lys Glu Val Leu Leu Leu
                45                  50

GTC CAC AAT CTG CCC CAG CAA CTT TTT GGC TAC AGC TGG           273
Val His Asn Leu Pro Gln Gln Leu Phe Gly Tyr Ser Trp
55                  60                  65

TAC AAA GGG GAA AGA GTG GAT GGC AAC CGT CAA ATT GTA           312
Tyr Lys Gly Glu Arg Val Asp Gly Asn Arg Gln Ile Val
        70                  75                  80

GGA TAT GCA ATA GGA ACT CAA CAA GCT ACC CCA GGG CCC           351
Gly Tyr Ala Ile Gly Thr Gln Gln Ala Thr Pro Gly Pro
```

-continued

|  |  |
|---|---|
| GCA AAC AGC GGT CGA GAG ACA ATA TAC CCC AAT GCA TCC<br>Ala Asn Ser Gly Arg Glu Thr Ile Tyr Pro Asn Ala Ser<br>95                           100                        105 | 390 |
| CTG CTG ATC CAG AAC GTC ACC CAG AAT GAC ACA GAA TTC<br>Leu Leu Ile Gln Asn Val Thr Gln Asn Asp Thr Gly Phe<br>               110                         115 | 429 |
| TAC ACC CTA CAA GTC ATA AAG TCA GAT CTT GTG AAT GAA<br>Tyr Thr Leu Gln Val Ile Lys Ser Asp Leu Val Asn Glu<br>120                         125                   130 | 468 |
| GAA GCA ACT GGA CAG TTC CAT GTA TAC CCG GAG CTG CCC<br>Glu Ala Thr Gly Gln Phe His Val Tyr Pro Glu Leu Pro<br>             135                    140                145 | 507 |
| AAG CCC TCC ATC TCC AGC AAC AAC TCC AAC CCT GTG GAG<br>Lys Pro Ser Ile Ser Ser Asn Asn Ser Asn Pro Val Glu<br>                  150                    155 | 546 |
| GAC AAG GAT GCT GTG GCC TCC ACC TGT GAA CCT GAG ACT<br>Asp Lys Asp Ala Val Ala Phe Thr Cys Glu Pro Glu Thr<br>160                         165                   170 | 585 |
| CAG GAC ACA ACC TAC CTG TGG TGG ATA AAC AAT CAG AGC<br>Gln Asp Thr Thr Tyr Leu Trp Trp Ile Asn Asn Gln Ser<br>             180                    190 | 624 |
| CTC CCG GTC AGT CCC AGG CTG CAG CTG TCC AAT GGC AAC<br>Leu Pro Val Ser Pro Arg Leu Gln Leu Ser Asn Gly Asn<br>195                         200                   205 | 663 |
| AGG ACC CTC ACT CTA CTC AGT GTC ACA AGG AAT GAC ACA<br>Arg Thr Leu Thr Leu Leu Ser Val Thr Arg Asn Asp Thr<br>             210                    215                220 | 702 |
| GGA CCC TAT GAG TGT GAA ATA CAG AAC CCA GTG AGT GCG<br>Gly Pro Tyr Glu Cys Glu Ile Gln Asn Pro Val Ser Ala<br>                       225                    230 | 741 |
| AAC CTC AGT GAC CCA GTC ACC TTG AAT GTC ACC TAT GGC<br>Asn Arg Ser Asp Pro Val Thr Leu Asn Val Thr Tyr Gly<br>235                         230                   235 | 780 |
| CCG GAC ACC CCC ACC ATT TCC CCT TCA GAC ACC TAT TAC<br>Pro Asp Thr Pro Thr Ile Ser Pro Ser Asp Thr Tyr Tyr<br>             240                    245 | 819 |
| CGT CCA GGG GCA AAC CTC AGC CTC TCC TGC TAT GCA GCC<br>Arg Pro Gly Ala Asn Leu Ser Leu Ser Cys Tyr Ala Ala<br>250                         255                   260 | 858 |
| TCT AAC CCA CCT GCA CAG TAC TCC TGG CTT ATC AAT GGA<br>Ser Asn Pro Pro Ala Gln Tyr Ser Trp Leu Ile Asn Gly<br>                  265                    270                275 | 897 |
| ACA TTC CAG CAA AGC ACA CAA GAG CTC TTT ATC CCT AAC<br>Thr Phe Gln Gln Ser Thr Gln Glu Leu Phe Ile Pro Asn<br>                       280                    285 | 936 |
| ATC ACT GTG AAT AAT AGT GGA TCC TAT ACC TGG CAC GCC<br>Ile Thr Val Asn Asn Ser Gly Ser Tyr Thr Cys His Ala<br>             290                    295                300 | 975 |
| AAT AAC TCA GTC ACT GGC TGC AAC AGG ACC ACA GTC AAG<br>Asn Asn Ser Val Thr Gly Cys Asn Arg Thr Thr Val Lys<br>                  305                    310 | 1014 |
| ACG ATC ATA GTC ACT GAT AAT GCT CTA CCA CAA GAA AAT<br>Thr Ile Ile Val Thr Asp Asn Ala Leu Pro Gln Glu Asn<br>315                         320                   325 | 1053 |
| GGC CTC TCA CCT GGG GCC ATT GCT GGC ATT GTG ATT GGA<br>Gly Leu Ser Pro Gly Ala Ile Ala Gly Ile Val Ile Gly<br>             330                    335                340 | 1092 |
| GTA GTG GCC CTG GTT GCT CTG ATA GCA GTA GCC CTG GCA<br>Val Val Ala Leu Val Ala Leu Ile Ala Val Ala Leu Ala | 1131 |

```
                345                      350
TGT TTT CTG CAT TTC GGG AAG ACC GGC AGG GCA AGC GAC       1170
Cys Phe Leu His Phe Gly Lys Thr Gly Arg Ala Ser Asp
    355                 360                 365
CAG CGT GAT CTC ACA GAG CAC AAA CCC TCA GTC TCC AAC       1209
Gln Arg Asp Leu Thr Glu His Lys Pro Ser Val Ser Asn
            370                 375
CAC ACT CAG GAC CAC TCC AAT GAC CCA CCT AAC AAG ATG       1248
His Thr Gln Asp His Ser Asn Asp Pro Pro Asn Lys Met
380                 385                 390
AAT GAA GTT ACT TAT TCT ACC CTG AAC TTT GAA GCC CAG       1287
Asn Glu Val Thr Tyr Ser Thr Leu Asn Phe Glu Ala Gln
        395                 400                 405
CAA CCC ACA CAA CCA ACT TCA GCC TCC CCA TCC CTA ACA       1326
Gln Pro Thr Gln Pro Thr Ser Ala Ser Pro Ser Leu Thr
                410                 415
GCC ACA GAA ATA ATT TAT TCA GAA GTA AAA AAG CAG           1362
Ala Thr Glu Ile Ile Tyr Ser Glu Val Lys Lys Gln
420                 425                 430

TAATGAAACC TGTCCTGCTC ACTGCAGTGC TGATGTATTT               1402
CAAGTCTCTC ACCCTCATCA CTAGGAGATT CCTTTCCCCT               1442
GTAGGGTAGA GGGGTGGGGA CAGAAACAAC TTTCTCCTAC               1482
TCTTCCTTCC TAATAGGCAT CTCCAGGCTG CCTGGTCACT               1522
GCCCCTCTCT CAGTGTCAAT AGATGAAAGT ACATTGGGAG               1562
TCTGTAGGAA ACCCAACCTT CTTGTCATTG AAATTTGGCA               1602
AAGCTGACTT TGGGAAAGAG GGACCAGAAC TTCCCCTCCC               1642
TTCCCCTTTT CCCAACCTGG ACTTGTTTTA AACTTGCCTG               1682
TTCAGAGCAC TCATTCCTTC CCACCCCCAG TCCTGTCCTA               1722
TCACTCTAAT TCGGATTTGC CATAGCCTTG AGGTTATGTC               1762
CTTTTCCATT AAGTACATGT GCCAGGAAAC AGCGAGAGAG               1802
AGAAAGTAAA CGGCAGTAAT GCTTCTCCTA TTTCTCCAAA               1842
GCCTTGTGTG AACTAGCAAA GAGAAGAAAA TCAAATATAT               1882
AACCAATAGT GAAATGCCAC AGGTTTGTCC ACTGTCAGGG               1922
TTGTCTACCT GTAGGATCAG GGTCTAAGCA CCTTGGTGCT               1962
TAGCTAGAAT ACCACCTAAT CCTTCTGGCA AGCCTGTCTT               2002
CAGAGAACCC ACTAGAAGCA ACTAGGAAAA ATCACTTGCC               2042
AAAATCCAAG GCAATTCCTG ATGGAAAATG CAAAAGCACA               2082
TATATGTTTT AATATCTTTA TGGGCTCTGT TCAAGGCAGT               2122
GCTGAGAGGG AGGGGTTATA GCTTCAGGAG GGAACCAGCT               2162
TCTGATAAAC ACAATCTGCT AGGAACTTGG GAAAGGAATC               2202
AGAGAGCTGC CCTTCAGCGA TTATTTAAAT TGTTAAAGAA               2242
TACACAATTT GGGGTATTGG GATTTTCTC CTTTTCTCTG                2282
AGACATTCCA CCATTTTAAT TTTTGTAACT GCTTATTTAT               2322
GTGAAAAGGG TTATTTTTAC TTAGCTTAGC TATGTCAGCC               2362
AATCCGATTG CCTTAGGTGA AAGAAACCAC CGAAATCCCT               2402
CAGGTCCCTT GGTCAGGAGC CTCTCAAGAT TTTTTTTGTC               2442
```

```
AGAGGCTCCA AATAGAAAAT AAGAAAAGGT TTTCTTCATT              2482

CATGGCTAGA GCTAGATTTA ACTCAGTTTC TAGGCACCTC              2522

AGACCAATCA TCAACTACCA TTCTATTCCA TGTTTGCACC              2562

TGTGCATTTT CTGTTTGCCC CCATTCACTT TGTCAGGAAA              2602

CCTTGGCCTC TGCTAAGGTG TATTTGGTCC TTGAGAAGTG              2642

GGAGCACCCT ACAGGGACAC TATCACTCAT GCTGGTGGCA              2682

TTGTTTACAG CTAGAAAGCT GCACTGGTGC TAATGCCCCT              2722

TGGGAAATGG GGCTGTGAGG AGGAGGATTA TAACTTAGGC              2762

CTAGCCTCTT TTAACAGCCT CTGAAATTTA TCTTTTCTTC              2802

TATGGGGTCT ATAAATGTAT CTTATAATAA AAAGGAAGGA              2842

CAGGAGGAAG ACAGGCAAAT GTACTTCTCA CCCAGTCTTC              2882

TACACAGATG GAATCTCTTT GGGGCTAAGA GAAAGGTTTT              2922

ATTCTATATT GCTTACCTGA TCTCATGTTA GGCCTAAGAG              2962

GCTTTCTCCA GGAGGATTAG CTTGGAGTTC TCTATACTCA              3002

GGTACCTCTT TCAGGGTTTT CTAACCCTGA CACGGACTGT              3042

GCATACTTTC CCTCATCCAT GCTGTGCTGT GTTATTTAAT              3082

TTTTCCTGGC TAAGATCATG TCTGAATTAT GTATGAAAAT              3122

TATTCTATGT TTTTATAATA AAAATAATAT ATCAGACATC              3162

GAAAAAAAAA A                                             3173

(2) INFORMATION FOR SEQ ID NO: 2:

(i) SEQUENCE CHARACTERISTICS:
        (A) LENGTH: 1630 nucleotides
        (B) TYPE: nucleic acid
        (C) STRANDEDNESS: single
        (D) TOPOLOGY: linear (xi) SEQUENCE DESCRIPTION: SEQ ID NO: 2:

CAGCCGTGCT CGAAGCGTTC CTGGAGCCCA AGCTCTCCTC              40

CACAGGTGAA GACAGGGCCA GCAGGAGACA                         70

CC ATG GGG CAC CTC TCA GCC CCA CTT CAC AGA GTG CGT       108
   Met Gly His Leu Ser Ala Pro Leu His Arg Val Arg
        5                  10

GTA CCC TGG CAG GGG CTT CTG CTC ACA GCC TCA CTT CTA      147
Val Pro Trp Gln Gly Leu Leu Leu Thr Ala Ser Leu Leu
        15                 20                 25

ACC TTC TGG AAC CCG CCC ACC ACT GCC CAG CTC ACT ACT      186
Thr Phe Trp Asn Pro Pro Thr Thr Ala Gln Leu Thr Thr
        30                 35

GAA TCC ATG CCA TTC AAT GTT GCA GAG GGG AAG GAG GTT      225
Glu Ser Met Pro Phe Asn Val Ala Glu Gly Lys Glu Val
 40                 45                 50

CTT CTC CTT GTC CAC AAT CTG CCC CAG CAA CTT TTT GGC      264
Leu Leu Leu Val His Asn Leu Pro Gln Gln Leu Phe Gly
            55                 60

TAC AGC TGG TAC AAA GGG GAA AGA GTG GAT GGC AAC CGT      303
Tyr Ser Trp Tyr Lys Gly Glu Arg Val Asp Gly Asn Arg
 65                 70                 75

CAA ATT GTA GGA TAT GCA ATA GGA ACT CAA CAA GCT ACC      342
Gln Ile Val Gly Tyr Ala Ile Gly Thr Gln Gln Ala Thr
        80                 85                 90
```

| | | |
|---|---|---|
| CCA GGG CCC GCA AAC AGC GGT CGA GAG ACA ATA TAC CCC<br>Pro Gly Pro Ala Asn Ser Gly Arg Glu Thr Ile Tyr Pro<br>                95                      100 | | 381 |
| AAT GCA TCC CTG CTG ATC CAG AAC GTC ACC CAG AAT GAC<br>Asn Ala Ser Leu Leu Ile Gln Asn Val Thr Gln Asn Asp<br>    105                   110               115 | | 420 |
| ACA GGA TTC TAC ACC CTA CAA GTC ATA AAG TCA GAT CTT<br>Thr Gly Phe Tyr Thr Leu Gln Val Ile Lys Ser Asp Leu<br>             120                 125 | | 459 |
| GTG AAT GAA GAA GCA ACT GGA CAG TTC CAT GTA TAC CCG<br>Val Asn Glu Glu Ala Thr Gly Gln Phe His Val Tyr Pro<br>130                 135               140 | | 498 |
| GAG CTG CCC AAG CCC TCC ATC TCC AGC AAC AAC TCC AAC<br>Glu Leu Pro Lys Pro Ser Ile Ser Ser Asn Asn Ser Asn<br>            145               150             155 | | 537 |
| CCT GTG GAG GAC AAG GAT GCT GTG GCC TTC ACC TGT GAA<br>Pro Val Glu Asp Lys Asp Ala Val Ala Phe Thr Cys Glu<br>                 160               165 | | 576 |
| CCT GAG ACT CAG GAC ACA ACC TAC CTG TGG TGG ATA AAC<br>Pro Glu Thr Gln Asp Thr Thr Tyr Leu Trp Trp Ile Asn<br>170                 175               180 | | 615 |
| AAT CAG AGC CTC CCG GTC AGT CCC AGG CTG CAG CTG TCC<br>Asn Gln Ser Leu Pro Val Ser Pro Arg Leu Gln Leu Ser<br>            185               190 | | 654 |
| AAT GGC AAC AGG ACC CTC ACT CTA CTC AGT GTC ACA AGG<br>Asn Gly Asn Arg Thr Leu Thr Leu Leu Ser Val Thr Arg<br>195                 200               205 | | 693 |
| AAT GAC ACA GGA CCC TAT GAG TGT GAA ATA CAG AAC CCA<br>Asn Asp Thr Gly Pro Tyr Glu Cys Glu Ile Gln Asn Pro<br>            210               215             220 | | 732 |
| GTG AGT GCG AAC CGC AGT GAC CCA GTC ACC TTG AAT GTC<br>Val Ser Ala Asn Arg Ser Asp Pro Val Thr Leu Asn Val<br>                 225               230 | | 771 |
| AAC TAT GGC CCG GAC ACC CCC ACC ATT TCC CCT TCA GAC<br>Thr Tyr Gly Pro Asp Thr Pro Thr Ile Ser Pro Ser Asp<br>         235                240             245 | | 810 |
| ACC TAT TAC CGT CCA GGG GCA AAC CTC AGC CTC TCC TGC<br>Thr Tyr Tyr Arg Pro Gly Ala Asn Leu Ser Leu Ser Cys<br>             250               255 | | 849 |
| TAT GCA GCC TCT AAC CCA CCT GCA CAG TAC TCC TGG CTT<br>Tyr Ala Ala Ser Asn Pro Pro Ala Gln Tyr Ser Trp Leu<br>260                 265               270 | | 888 |
| ATC AAT GGA ACA TTC CAG CAA AGC ACA CAA GAG CTC TTT<br>Ile Asn Gly Thr Phe Gln Gln Ser Thr Gln Glu Leu Phe<br>            275               280             285 | | 927 |
| ATC CCT AAC ATC ACT GTG AAT AAT AGT GGA TCC TAT ACC<br>Ile Pro Asn Ile Thr Val Asn Asn Ser Gly Ser Tyr Thr<br>                 290               295 | | 966 |
| TGC CAC GCC AAT AAC TCA GTC ACT GGC TGC AAC AGG ACC<br>Cys His Ala Asn Asn Ser Val Thr Gly Cys Asn Arg Thr<br>300                 305               310 | | 1005 |
| ACA GTC AAG ACG ATC ATA GTC ACT GAG CTA AGT CCA GTA<br>Thr Val Lys Thr Ile Ile Val Thr Glu Leu Ser Pro Val<br>            315               320 | | 1044 |
| GTA GCA AAG CCC CAA ATC AAA GCC AGC AAG ACC ACA GTC<br>Val Ala Lys Pro Gln Ile Lys Ala Ser Lys Thr Thr Val<br>325                 330               335 | | 1083 |
| ACA GGA GAT AAG GAC TCT GTG AAC CTG ACC TGC TCC ACA<br>Thr Gly Asp Lys Asp Ser Val Asn Leu Thr Cys Ser Thr<br>                 340               345             350 | | 1122 |

| | | |
|---|---|---|
| AAT GAC ACT GGA ATC TCC ATC CGT TGG TTC TTC AAA AAC<br>Asn Asp Thr Gly Ile Ser Ile Arg Trp Phe Phe Lys Asn<br>355 360 | | 1161 |
| CAG AGT CTC CCG TCC TCG GAG AGG ATG AAG CTG TCC CAG<br>Gln Ser Leu Pro Ser Ser Glu Arg Met Lys Leu Ser Gln<br>365 370 375 | | 1200 |
| GGC AAC ACC ACC CTC AGC ATA AAC CCT GTC AAG AGG GAG<br>Gly Asn Thr Thr Leu Ser Ile Asn Pro Val Lys Arg Glu<br>380 385 | | 1239 |
| GAT GCT GGG ACG TAT TGG TGT GAG GTC TTC AAC CCA ATC<br>Asp Ala Gly Thr Tyr Trp Cys Glu Val Phe Asn Pro Ile<br>390 395 400 | | 1278 |
| AGT AAG AAC CAA AGC GAC CCC ATC ATG CTG AAC GTA AAC<br>Ser Lys Asn Gln Ser Asp Pro Ile Met Leu Asn Val Asn<br>405 410 415 | | 1317 |
| TAT AAT GCT CTA CCA CAA GAA AAT GGC CTC TCA CCT GGG<br>Tyr Asn Ala Leu Pro Gln Glu Asn Gly Leu Ser Pro Gly<br>420 425 | | 1356 |
| GCC ATT GCT GGC ATT GTG ATT GGA GTA GTG GCC CTG GTT<br>Ala Ile Ala Gly Ile Val Ile Gly Val Val Ala Leu Val<br>430 435 440 | | 1395 |
| GCT CTG ATA GCA GTA GCC CTG GCA TGT TTT CTG CAT TTC<br>Ala Leu Ile Ala Val Ala Leu Ala Cys Phe Leu His Phe<br>445 450 | | 1434 |
| GGG AAG ACC GGC AGC TCA GGA CCA CTC CAA<br>Gly Lys Thr Gly Ser Ser Gly Pro Leu Gln<br>455 460 | | 1464 |
| TGACCCACCT AACAAGATGA ATGAAGTTAC TTATTCTACC | | 1504 |
| CTGAACTTTG AAGCCCAGCA ACCCACACAA CCAACTTCAG | | 1544 |
| CCTCCCCATC CCTAACAGCC ACAGAAATAA TTTATTCAGA | | 1584 |
| AGTAAAAAAG CAGTAATGAA ACCTGAAAAA AAAAAAAAA | | 1624 |
| AAAAAA | | 1630 |

(2) INFORMATION FOR SEQ ID NO: 3:

(i) SEQUENCE CHARACTERISTICS:
        (A) LENGTH: 1339 nucleotides
        (B) TYPE: nucleic acid
        (C) STRANDEDNESS: single
        (D) TOPOLOGY: linear (xi) SEQUENCE DESCRIPTION: SEQ ID NO: 3:

| | | |
|---|---|---|
| CAGCCGTGCT CGAAGCGTTC CTGGAGCCCA AGCTCTCCTC | | 40 |
| CACAGGTGAA GACAGGGCCA GCAGGAGACA CC ATG<br>                                              Met | | 75 |
| GGG CAC CTC TCA GCC CCA CTT CAC AGA GTG CGT GTA CCC<br>Gly His Leu Ser Ala Pro Leu His Arg Val Arg Val Pro<br>5 10 | | 114 |
| TGG CAG GGG CTT CTG CTC ACA GCC TCA CTT CTA ACC TTC<br>Trp Gln Gly Leu Leu Leu Thr Ala Ser Leu Leu Thr Phe<br>15 20 25 | | 153 |
| TGG AAC CCG CCC ACC ACT GCC CAG CTC ACT ACT GAA TCC<br>Trp Asn Pro Pro Thr Thr Ala Gln Leu Thr Thr Glu Ser<br>30 35 40 | | 192 |
| ATG CCA TTC AAT GTT GCA GAG GGG AAG GAG GTT CTT CTC<br>Met Pro Phe Asn Val Ala Glu Gly Lys Glu Val Leu Leu<br>45 50 | | 231 |
| CTT GTC CAC AAT CTG CCC CAG CAA CTT TTT GGC TAC AGC | | 270 |

-continued

| | | |
|---|---|---|
| Leu Val His Asn Leu Pro Gln Gln Leu Phe Gly Tyr Ser<br>55                   60                        65 | | |

```
TGG TAC AAA GGG GAA AGA GTG GAT GGC AAC CGT CAA ATT           309
Trp Tyr Lys Gly Glu Arg Val Asp Gly Asn Arg Gln Ile
            70                  75

GTA GGA TAT GCA ATA GGA ACT CAA CAA GCT ACC CCA GGG           348
Val Gly Tyr Ala Ile Gly Thr Gln Gln Ala Thr Pro Gly
 80              85                  90

CCC GCA AAC AGC GGT CGA GAG ACA ATA TAC CCC AAT GCA           387
Pro Ala Asn Ser Gly Arg Glu Thr Ile Tyr Pro Asn Ala
         95                 100                 105

TCC CTG CTG ATC CAG AAC GTC ACC CAG AAT GAC ACA GGA           426
Ser Leu Leu Ile Gln Asn Val Thr Gln Asn Asp Thr Gly
                110                 115

TTC TAC ACC CTA CAA GTC ATA AAG TCA GAT CTT GTG AAT           465
Phe Tyr Thr Leu Gln Val Ile Lys Ser Asp Leu Val Asn
120                 125                 130

GAA GAA GCA ACT GGA CAG TTC CAT GTA TAC CCG GAG CTG           504
Glu Glu Ala Thr Gly Gln Phe His Val Tyr Pro Glu Leu
            135                 140

CCC AAG CCC TCC ATC TCC AGC AAC AAC TCC AAC CCT GTG           543
Pro Lys Pro Ser Ile Ser Ser Asn Asn Ser Asn Pro Val
145                 150                 155

GAG GAC AAG GAT GCT GTG GCC TTC ACC TGT GAA CCT GAG           582
Glu Asp Lys Asp Ala Val Ala Phe Thr Cys Glu Pro Glu
        160                 165                 170

ACT CAG GAC ACA ACC TAC CTG TGG TGG ATA AAC AAT CAG           621
Thr Gln Asp Thr Thr Tyr Leu Trp Trp Ile Asn Asn Gln
                175                 180

AGC CTC CCG GTC AGT CCC AGG CTG CAG CTG TCC AAT GGC           660
Ser Leu Pro Val Ser Pro Arg Leu Gln Leu Ser Asn Gly
    185                 190                 195

AAC AGG ACC CTC ACT CTA CTC AGT GTC ACA AGG AAT GAC           699
Asn Arg Thr Leu Thr Leu Leu Ser Val Thr Arg Asn Asp
                200                 205

ACA GGA CCC TAT GAG TGT GAA ATA CAG AAC CCA GTG AGT           738
Thr Gly Pro Tyr Glu Cys Glu Ile Gln Asn Pro Val Ser
210                 215                 220

GCG AAC CGC AGT GAC CCA GTC ACC TTG AAT GTC ACC TAT           777
Ala Asn Arg Ser Asp Pro Val Thr Leu Asn Val Thr Tyr
        225                 230                 235

GGC CCG GAC ACC CCC ACC ATT TCC CCT TCA GAC ACC TAT           816
Gly Pro Asp Thr Pro Thr Ile Ser Pro Ser Asp Thr Tyr
                240                 245

TAC CGT CCA GGG GCA AAC CTC AGC CTC TCC TGC TAT GCA           855
Tyr Arg Pro Gly Ala Asn Leu Ser Leu Ser Cys Tyr Ala
    250                 255                 260

GCC TCT AAC CCA CCT GCA CAG TAC TCC TGG CTT ATC AAT           894
Ala Ser Asn Pro Pro Ala Gln Tyr Ser Trp Leu Ile Asn
                265                 270

GGA ACA TTC CAG CAA AGC ACA CAA GAG CTC TTT ATC CCT           933
Gly Thr Phe Gln Gln Ser Thr Gln Glu Leu Phe Ile Pro
275                 280                 285

AAC ATC ACT GTG AAT AAT AGT GGA TCC TAT ACC TGC CAC           972
Asn Ile Thr Val Asn Asn Ser Gly Ser Tyr Thr Cys His
        290                 295                 300

GCC AAT AAC TCA GTC ACT GGC TGC AAC AGG ACC ACA GTC          1011
Ala Asn Asn Ser Val Thr Gly Cys Asn Arg Thr Thr Val
                305                 310

AAG ACG ATC ATA GTC ACT GAT AAT GCT CTA CCA CAA GAA          1050
```

-continued

```
        Lys Thr Ile Ile Val Thr Asp Asn Ala Leu Pro Gln Glu
            315                 320                 325

AAT GGC CTC TCA CCT GGG GCC ATT GCT GGC ATT GTG ATT              1089
Asn Gly Leu Ser Pro Gly Ala Ile Ala Gly Ile Val Ile
                330                 335

GGA GTA GTG GCC CTG GTT GCT CTG ATA GCA GTA GCC CTG              1128
Gly Val Val Ala Leu Val Ala Leu Ile Ala Val Ala Leu
340                 345                 350

GCA TGT TTT CTG CAT TTC GGG AAG ACC GGC AGC TCA GGA              1167
Ala Cys Phe Leu His Phe Gly Lys Thr Gly Ser Ser Gly
            355                 360                 365

CCA CTC CAA TGACCCACCT AACAAGATGA ATGAAGTTAC                     1206
Pro Leu Gln

TTATTCTACC CTGAACTTTG AAGCCCAGCA ACCCACACAA                      1246

CCAACTTCAG CCTCCCCATC CCTAACAGCC ACAGAAATAA                      1286

TTTATTCAGA AGTAAAAAAG CAGTAATGAA ACCTGAAAAA                      1326

AAAAAAAAAA AAA                                                   1339

(2) INFORMATION FOR SEQ ID NO: 4:

(i) SEQUENCE CHARACTERISTICS:
        (A) LENGTH: 862 nucleotides
        (B) TYPE: nucleic acid
        (C) STRANDEDNESS: single
        (D) TOPOLOGY: linear (xi) SEQUENCE DESCRIPTION: SEQ ID NO: 4:

GGGGTTTACA CAACCACCAC CCCATCAAAC CCTTCATCAC                        40

CAGCAACAAC TCCAACCCCG TGGAGGATGA GGATGCTGTA                        80

GCCTTAACCT GTGAACCTCA GATTCAGAAC ACAACCTACC                       120

TGTGGTGGGT AAATAATCAG AGCCTCCCGG TCAGTCCCAG                       160

GCTGCAGCTG TCCAATGACA CAGGACCCT CACTCTACTC                        200

AGTGTCACAA GGAATGATGT AGGACCCTAT GAGTGTGGAA                       240

TCCAGAACGA ATTAAGTGTT GACCACAGCG ACCCAGTCAT                       280

CCTGAATGTC CTCTATGGCC CAGACGACCC CACCATTTCC                       320

CCCTCATACA CCTATTACCG TCCAGGGGTG AACCTCAGCC                       360

TCTCCTGCCA TGCAGCCTCT AACCCACCTG CACAGTATTC                       400

TTGGCTGATT GATGGGAACA TCCAGCAACA CACACAAGAG                       440

CTCTTTATCT CCAACATCAC TGAGAAGAAC AGCGGACTCT                       480

ATACCTGCCA GGCCAATAAC TCAGCCAGTG GCCACAGCAG                       520

GACTACAGTC AAGACAATCA CAGTCTCTGC GGACGTGCCC                       560

AAGCCCTCCA TCTCCAGCAA CAACTCCAAA CCCGTGGAGG                       600

ACAAGGATGC TGTGGCCTTC ACTGTGAAC CTGAGGCTCA                        640

GAACACAACC TACCTGTGGT GGGTAAATGG TCAGAGCCTC                       680

CCAGTCAGTC CCAGGCTGCA GCTGTCCAAT GGCAACAGGA                       720

CCCTCACTCT ATTCAATGTC ACAAGAAATG ACGCAAGAGC                       760

CTATGTATGT GGAATCCAGA ACTCAGTGAG TGCAAACCGC                       800

AGTGACCCAG TCACCCTGGA TGTCCTCTAT GGGCCGGACA                       840

CCCCCATCAT TTCCCCCCCC CC                                          862
```

(2) INFORMATION FOR SEQ ID NO: 5:

(i) SEQUENCE CHARACTERISTICS:
        (A) LENGTH: 2839 nucleotides
        (B) TYPE: nucleic acid
        (C) STRANDEDNESS: single
        (D) TOPOLOGY: linear (xi) SEQUENCE DESCRIPTION: SEQ ID NO: 5:

```
CACC ATG GAG TCT CCC TCG GCC CCT CTC CAC AGA TGG TGC                40
     Met Glu Ser Pro Ser Ala Pro Leu His Arg Trp Cys
             -30                 -25

ATC CCC TGG CAG AGG CTC CTG CTC ACA GCC TCA CTT CTA                 79
Ile Pro Trp Gln Arg Leu Leu Leu Thr Ala Ser Leu Leu
        -20                 -15                 -10

ACC TTC TGG AAC CCG CCC ACC ACT GCC AAG CTC ACT ATT                 118
Thr Phe Trp Asn Pro Pro Thr Thr Ala Lys Leu Thr Ile
                -5                   1

GAA TCC ACG CCG TTC AAT GTC GCA GAG GGG AAG GAG GTG                 157
Glu Ser Thr Pro Phe Asn Val Ala Glu Gly Lys Glu Val
 5                  10                  15

CTT CTA CTT GTC CAC AAT CTG CCC CAG CAT CTT TTT GGC                 196
Leu Leu Leu Val His Asn Leu Pro Gln His Leu Phe Gly
         20                  25                  30

TAC AGC TGG TAC AAA GGT GAA AGA GTG GAT GGC AAC CGT                 235
Tyr Ser Trp Tyr Lys Gly Glu Arg Val Asp Gly Asn Arg
             35                  40

CAA ATT ATA GGA TAT GTA ATA GGA ACT CAA CAA GCT ACC                 274
Gln Ile Ile Gly Tyr Val Ile Gly Thr Gln Gln Ala Thr
     45                  50                  55

CCA GGG CCC GCA TAC AGT GGT CGA GAG ATA ATA TAC CCC                 313
Pro Gly Pro Ala Tyr Ser Gly Arg Glu Ile Ile Tyr Pro
             60                  65

AAT GCA TCC CTG CTG ATC CAG AAC ATC ATC CAG AAT GAC                 352
Asn Ala Ser Leu Leu Ile Gln Asn Ile Ile Gln Asn Asp
 70                  75                  80

ACA GGA TTC TAC ACC CTA CAC GTC ATA AAG TCA GAT CTT                 391
Thr Gly Phe Tyr Thr Leu His Val Ile Lys Ser Asp Leu
         85                  90                  95

GTG AAT GAA GAA GCA ACT GGC CAG TTC CGG GTA TAC CCG                 430
Val Asn Glu Glu Ala Thr Gly Gln Phe Arg Val Tyr Pro
                 100                 105

GAG CTG CCC AAG CCC TCC ATC TCC AGC AAC AAC TCC AAA                 469
Glu Leu Pro Lys Pro Ser Ile Ser Ser Asn Asn Ser Lys
     110                 115                 120

CCC GTG GAG GAC AAG GAT GCT GTG GCC TTC ACC TGT GAA                 508
Pro Val Glu Asp Lys Asp Ala Val Ala Phe Thr Cys Glu
             125                 130

CCT GAG ACT CAG GAC GCA ACC TAC CTG TGG TGG GTA AAC                 547
Pro Glu Thr Gln Asp Ala Thr Tyr Leu Trp Trp Val Asn
135                 140                 145

AAT CAG AGC CTC CCG GTC AGT CCC AGG CTG CAG CTG TCC                 586
Asn Gln Ser Leu Pro Val Ser Pro Arg Leu Gln Leu Ser
         150                 155                 160

AAT GGC AAC AGG ACC CTC ACT CTA TTC AAT GTC ACA AGA                 625
Asn Gly Asn Arg Thr Leu Thr Leu Phe Asn Val Thr Arg
                 165                 170

AAT GAA CAA GCA AGC TAC AAA TGT GAA ACC CAG AAC CCA                 664
Asn Glu Gln Ala Ser Tyr Lys Cys Glu Thr Gln Asn Pro
     175                 180                 185
```

```
GTG AGT GCC AGG CGC AGT GAT TCA GTC ATC CTG AAT GTC          703
Val Ser Ala Arg Arg Ser Asp Ser Val Ile Leu Asn Val
        190                 195

CTC TAT GGC CCG GAT GCC CCC ACC ATT TCC CCT CTA AAC          742
Leu Tyr Gly Pro Asp Ala Pro Thr Ile Ser Pro Leu Asn
200             205                 210

ACA TCT TAC AGA TCA GGG GAA AAT CTG AAC CTC TCC TGC          781
Thr Ser Tyr Arg Ser Gly Glu Asn Leu Asn Leu Ser Cys
        215                 220                 225

CAC GCA GCC TCT AAC CCA CCT GCA CAG TAC TCT TGG TTT          820
His Ala Ala Ser Asn Pro Pro Ala Gln Tyr Ser Trp Phe
            230                 235

GTC AAT GGG ACT TTC CAG CAA TCC ACC CAA GAG CTC TTT          859
Val Asn Gly Thr Phe Gln Gln Ser Thr Gln Glu Leu Phe
240                 245                 250

ATC CCC AAC ATC ACT GTG AAT AAT AGT GGA TCC TAT ACG          898
Ile Pro Asn Ile Thr Val Asn Asn Ser Gly Ser Tyr Thr
        255                 260

TGC CAA GCC CAT AAC TCA GAC ACT GGC CTC AAT AGG ACC          937
Cys Gln Ala His Asn Ser Asp Thr Gly Leu Asn Arg Thr
265             270                 275

ACA GTC ACG ACG ATC ACA GTC TAT GCA GAG CCA CCC AAA          976
Thr Val Thr Thr Ile Thr Val Tyr Ala Glu Pro Pro Lys
        280                 285                 290

CCC TTC ATC ACC AGC AAC AAC TCC AAC CCC GTG GAG GAT         1015
Pro Phe Ile Thr Ser Asn Asn Ser Asn Pro Val Glu Asp
                295                 300

GAG GAT GCT GTA GCC TTA ACC TGT GAA CCT GAG ATT CAG         1054
Glu Asp Ala Val Ala Leu Thr Cys Glu Pro Glu Ile Gln
        305                 310                 315

AAC ACA ACC TAC CTG TGG TGG GTA AAT AAT CAG AGC CTC         1093
Asn Thr Thr Tyr Leu Trp Trp Val Asn Asn Gln Ser Leu
                320                 325

CCG GTC AGT CCC AGG CTG CAG CTG TCC AAT GAC AAC AGG         1132
Pro Val Ser Pro Arg Leu Gln Leu Ser Asn Asp Asn Arg
330                 335                 340

ACC CTC ACT CTA CTC AGT GTC ACA AGG AAT GAT GTA GGA         1171
Thr Leu Thr Leu Leu Ser Val Thr Arg Asn Asp Val Gly
        345                 350                 355

CCC TAT GAG TGT GGA ATC CAG AAC GAA TTA AGT GTT GAC         1210
Pro Tyr Glu Cys Gly Ile Gln Asn Glu Leu Ser Val Asp
                360                 365

CAC AGC GAC CCA GTC ATC CTG AAT GTC CTC TAT GGC CCA         1249
His Ser Asp Pro Val Ile Leu Asn Val Leu Tyr Gly Pro
        370                 375                 380

GAC GAC CCC ACC ATT TCC CCC TCA TAC ACC TAT TAC CGT         1288
Asp Asp Pro Thr Ile Ser Pro Ser Tyr Thr Tyr Tyr Arg
                385                 390

CCA GGG GTG AAC CTC AGC CTC TCC TGC CAT GCA GCC TCT         1327
Pro Gly Val Asn Leu Ser Leu Ser Cys His Ala Ala Ser
395                 400                 405

AAC CCA CCT GCA CAG TAT TCT TGG CTG ATT GAT GGG AAC         1366
Asn Pro Pro Ala Gln Tyr Ser Trp Leu Ile Asp Gly Asn
        410                 415                 420

ATC CAG CAA CAC ACA CAA GAG CTC TTT ATC TCC ACC ATC         1405
Ile Gln Gln His Thr Gln Glu Leu Phe Ile Ser Asn Ile
                425                 430

ACT GAG AAG AAC AGC GGA CTC TAT ACC TGC CAG GCC AAT         1444
Thr Glu Lys Asn Ser Gly Leu Tyr Thr Cys Gln Ala Asn
435                 440                 445
```

| | |
|---|---|
| AAC TCA GCC AGT GGC CAC AGC AGG ACT ACA GTC AAG ACA<br>Asn Ser Ala Ser Gly His Ser Arg Thr Thr Val Lys Thr<br>              450                             455 | 1483 |
| ATC ACA GTC TCT GCG GAC GTG CCC AAG CCC TCC ATC TCC<br>Ile Thr Val Ser Ala Asp Val Pro Lys Pro Ser Ile Ser<br>460                       465                       470 | 1522 |
| AGC AAC AAC TCC AAA CCC GTG GAG GAC AAG GAT GCT GTG<br>Ser Asn Asn Ser Lys Pro Val Glu Asp Lys Asp Ala Val<br>           475                     480               485 | 1561 |
| GCC TTC ACC TGT GAA CCT GAG GCT CAG AAC ACA ACC TAC<br>Ala Phe Thr Cys Glu Pro Glu Ala Gln Asn Thr Thr Tyr<br>              490                       495 | 1600 |
| CTG TGG TGG GTA AAT GGT CAG AGC CTC CCA GTC AGT CCC<br>Leu Trp Trp Val Asn Gly Gln Ser Leu Pro Val Ser Pro<br>    500                     505                   510 | 1639 |
| AGG CTG CAG CTG TCC AAT GGC AAC AGG ACC CTC ACT CTA<br>Arg Leu Gln Leu Ser Asn Gly Asn Arg Thr Leu Thr Leu<br>           515                     520 | 1678 |
| TTC AAT GTC ACA AGA AAT GAC GCA AGA GCC TAT GTA TGT<br>Phe Asn Val Thr Arg Asn Asp Ala Arg Ala Tyr Val Cys<br>525                     530                     535 | 1717 |
| GGA ATC CAG AAC TCA GTG AGT GCA AAC CGC AGT GAC CCA<br>Gly Ile Gln Asn Ser Val Ser Ala Asn Arg Ser Asp Pro<br>           540                   545               550 | 1756 |
| GTC ACC CTG GAT GTC CTC TAT GGG CCG GAC ACC CCC ATC<br>Val Thr Leu Asp Val Leu Tyr Gly Pro Asp Thr Pro Ile<br>                555                     560 | 1795 |
| ATT TCC CCC CCA GAC TCG TCT TAC CTT TCG GGA GCG AAC<br>Ile Ser Pro Pro Asp Ser Ser Tyr Leu Ser Gly Ala Asn<br>565                     570                     575 | 1834 |
| CTC AAC CTC TCC TGC CAC TCG GCC TCT AAC CCA TCC CCG<br>Leu Asn Leu Ser Cys His Ser Ala Ser Asn Pro Ser Pro<br>           580                   585 | 1873 |
| CAG TAT TCT TGG CGT ATC AAT GGG ATA CCG CAG CAA CAC<br>Gln Tyr Ser Trp Arg Ile Asn Gly Ile Pro Gln Gln His<br>590                     595                     600 | 1912 |
| ACA CAA GTT CTC TTT ATC GCC AAA ATC ACG CCA AAT AAT<br>Thr Gln Val Leu Phe Ile Ala Lys Ile Thr Pro Asn Asn<br>           605                   610               615 | 1951 |
| AAC GGG ACC TAT GCC TGT TTT GTC TCT AAC TTG GCT ACT<br>Asn Gly Thr Tyr Ala Cys Phe Val Ser Asn Leu Ala Thr<br>                620                     625 | 1990 |
| GGC CGC AAT AAT TCC ATA GTC AAG AGC ATC ACA GTC TCT<br>Gly Arg Asn Asn Ser Ile Val Lys Ser Ile Thr Val Ser<br>    630                     635                   640 | 2029 |
| GCA TCT GGA ACT TCT CCT GGT CTC TCA GCT GGG GCC ACT<br>Ala Ser Gly Thr Ser Pro Gly Leu Ser Ala Gly Ala Thr<br>           645                     650 | 2068 |
| GTC GGC ATC ATG ATT GGA GTG CTG GTT GGG GTT GCT CTG<br>Val Gly Ile Met Ile Gly Val Leu Val Gly Val Ala Leu<br>655                     660                     665 | 2107 |
| ATA TAGCAGCCCT GGTGTAGTTT CTTCATTTCA GGAAGACTGA<br>Ile | 2150 |
| CAGTTGTTTT GCTTCTTCCT TAAAGCATTT GCAACAGCTA | 2190 |
| CAGTCTAAAA TTGCTTCTTT ACCAAGGATA TTTACAGAAA | 2230 |
| ATACTCTGAC CAGAGATCGA GACCATCCTA GCCAACATCG | 2270 |
| TGAAACCCCA TCTCTACTAA AAATACAAAA ATGAGCTGGG | 2310 |
| CTTGGTGGCG CGCACCTGTA GTCCCAGTTA CTCGGGAGGC | 2350 |

-continued

| | |
|---|---|
| TGAGGCAGGA GAATCGCTTG AACCCGGGAG GTGGAGATTG | 2390 |
| CAGTGAGCCC AGATCGCACC ACTGCACTCC AGTCTGGCAA | 2430 |
| CAGAGCAAGA CTCCATCTCA AAAAGAAAAG AAAAGAAGAC | 2470 |
| TCTGACCTGT ACTCTTGAAT ACAAGTTTCT GATACCACTG | 2510 |
| CACTGTCTGA GAATTTCCAA AACTTTAATG AACTAACTGA | 2550 |
| CAGCTTCATG AAACTGTCCA CCAAGATCAA GCAGAGAAAA | 2590 |
| TAATTAATTT CATGGGGACT AAATGAACTA ATGAGGATAA | 2630 |
| TATTTTCATA ATTTTTTATT TGAAATTTTG CTGATTCTTT | 2670 |
| AAATGTCTTG TTTCCCAGAT TTCAGGAAAC TTTTTTTCTT | 2710 |
| TTAAGCTATC CACTCTTACA GCAATTTGAT AAAATATACT | 2750 |
| TTTGTGAACA AAAATTGAGA CATTTACATT TTATCCCTAT | 2790 |
| GTGGTCGCTC CAGACTTGGG AAACTATTCA TGAATATTTA | 2830 |
| TATTGTATG | 2839 |

(2) INFORMATION FOR SEQ ID NO: 6:

(i) SEQUENCE CHARACTERISTICS:
        (A) LENGTH: 3461 nucleotides
        (B) TYPE: nucleic acid
        (C) STRANDEDNESS: single
        (D) TOPOLOGY: linear (xi) SEQUENCE DESCRIPTION: SEQ ID NO: 6:

```
CAGCCGTGCT CGAAGCGTTC CTGGAGCCCA AGCTCTCCTC                        40

CACAGGTGAA GACAGGGCCA GCAGGAGACA CC ATG GGG                        78
                                     Met Gly

CAC CTC TCA GCC CCA CTT CAC AGA GTC CGT GTA CCC TGG               117
His Leu Ser Ala Pro Leu His Arg Val Arg Val Pro Trp
          5                  10                  15

CAG GGG CTT CTG CTC ACA GCC TCA CTT CTA ACC TTC TGG               156
Gln Gly Leu Leu Leu Thr Ala Ser Leu Leu Thr Phe Trp
                 20                  25

AAC CCG CCC ACC ACT GCC CAG CTC ACT ACT GAA TCC ATG               195
Asn Pro Pro Thr Thr Ala Gln Leu Thr Thr Glu Ser Met
         30                  35                  40

CCA TTC AAT GTT GCA GAG GGG AAG GAG GTT CTT CTC CTT               234
Pro Phe Asn Val Ala Glu Gly Lys Glu Val Leu Leu Leu
                 45                  50

GTC CAC AAT CTG CCC CAG CAA CTT TTT GGC TAC AGC TGG               273
Val His Asn Leu Pro Gln Gln Leu Phe Gly Tyr Ser Trp
55                  60                  65

TAC AAA GGG GAA AGA GTG GAT GGC AAC CGT CAA ATT GTA               312
Tyr Lys Gly Glu Arg Val Asp Gly Asn Arg Gln Ile Val
         70                  75                  80

GGA TAT GCA ATA GGA ACT CAA CAA GCT ACC CCA GGG CCC               351
Gly Tyr Ala Ile Gly Thr Gln Gln Ala Thr Pro Gly Pro
                 85                  90

GCA AAC AGC GGT CGA GAG ACA ATA TAC CCC AAT GCA TCC               390
Ala Asn Ser Gly Arg Glu Thr Ile Tyr Pro Asn Ala Ser
     95                  100                 105

CTG CTG ATC CAG AAC GTC ACC CAG AAT GAC ACA GGA TTC               429
Leu Leu Ile Gln Asn Val Thr Gln Asn Asp Thr Gly Phe
             110                 115

TAC ACC CTA CAA GTC ATA AAG TCA GAT CTT GTG AAT GAA               468
```

```
                Tyr Thr Leu Gln Val Ile Lys Ser Asp Leu Val Asn Glu
                120             125             130

GAA GCA ACT GGA CAG TTC CAT GTA TAC CCG GAG CTG CCC                      507
Glu Ala Thr Gly Gln Phe His Val Tyr Pro Glu Leu Pro
            135             140             145

AAG CCC TCC ATC TCC AGC AAC AAC TCC ACC CCT GTG GAG                      546
Lys Pro Ser Ile Ser Ser Asn Asn Ser Thr Pro Val Glu
                150             155

GAC AAG GAT GCT GTG GCC TTC ACC TGT GAA CCT GAG ACT                      585
Asp Lys Asp Ala Val Ala Phe Thr Cys Glu Pro Glu Thr
        160             165             170

CAG GAC ACA ACC TAC CTG TGG TGG ATA AAC AAT CAG AGC                      624
Gln Asp Thr Thr Tyr Leu Trp Trp Ile Asn Asn Gln Ser
            175             180

CTC CCG GTC AGT CCC AGG CTG CAG CTG TCC AAT GGC AAC                      663
Leu Pro Val Ser Pro Arg Leu Gln Leu Ser Asn Gly Asn
185             190             195

AGG ACC CTC ACT CTA CTC AGT GTC ACA AGG AAT GAC ACA                      702
Arg Thr Leu Thr Leu Leu Ser Val Thr Arg Asn Asp Thr
                200             205             210

GGA CCC TAT GAG TGT GAA ATA CAG AAC CCA GTG AGT GCG                      741
Gly Pro Tyr Glu Cys Glu Ile Gln Asn Pro Val Ser Ala
                    215             220

AAC CGC AGT GAC CCA GTC ACC TTG AAT GTC ACC TAT GGC                      780
Asn Arg Ser Asp Pro Val Thr Leu Asn Val Thr Tyr Gly
        225             230             235

CCG GAC ACC CCC ACC ATT TCC CCT TCA GAC ACC TAT TAC                      819
Pro Asp Thr Pro Thr Ile Ser Pro Ser Asp Thr Tyr Tyr
            240             245

CGT CCA GGG GCA AAC CTC AGC CTC TCC TGC TAT GCA GCC                      858
Arg Pro Gly Ala Asn Leu Ser Leu Ser Cys Tyr Ala Ala
250             255             260

TCT AAC CCA CCT GCA CAG TAC TCC TGG CTT ATC AAT GGA                      897
Ser Asn Pro Pro Ala Gln Tyr Ser Trp Leu Ile Asn Gly
                265             270             275

ACA TTC CAG CAA AGC ACA CAA GAG CTC TTT ATC CCT AAC                      936
Thr Phe Gln Gln Ser Thr Gln Glu Leu Phe Ile Pro Asn
                    280             285

ATC ACT GTG AAT AAT AGT GGA TCC TAT ACC TGC CAC GCC                      975
Ile Thr Val Asn Asn Ser Gly Ser Tyr Thr Cys His Ala
        290             295             300

AAT AAC TCA GTC ACT GGC TGC AAC AGG ACC ACA GTC AAG                     1014
Asn Asn Ser Val Thr Gly Cys Asn Arg Thr Thr Val Lys
            305             310

ACG ATC ATA GTC ACT GAG CTA AGT CCA GTA GTA GCA AAG                     1053
Thr Ile Ile Val Thr Glu Leu Ser Pro Val Val Ala Lys
315             320             325

CCC CAA ATC AAA GCC AGC AAG ACC ACA GTC ACA GGA GAT                     1092
Pro Gln Ile Lys Ala Ser Lys Thr Thr Val Thr Gly Asp
                330             335             340

AAG GAC TCT GTG AAC CTG ACC TGC TCC ACA AAT GAC ACT                     1131
Lys Asp Ser Val Asn Leu Thr Cys Ser Thr Asn Asp Thr
                    345             350

GGA ATC TCC ATC CGT TGG TTC TTC AAA AAC CAG AGT CTC                     1170
Gly Ile Ser Ile Arg Trp Phe Phe Lys Asn Gln Ser Leu
        355             360             365

CCG TCC TCG GAG AGG ATG AAG CTG TCC CAG GGC AAC ACC                     1209
Pro Ser Ser Glu Arg Met Lys Leu Ser Gln Gly Asn Thr
            370             375

ACC CTC AGC ATA AAC CCT GTC AAG AGG GAG GAT GCT GGG                     1248
Thr Leu Ser Ile Asn Pro Val Lys Arg Glu Asp Ala Gly
```

```
                                                        -continued

Thr Leu Ser Ile Asn Pro Val Lys Arg Glu Asp Ala Gly
380                 385                 390

ACG TAT TGG TGT GAG GTC TTC AAC CCA ATC AGT AAG AAC        1287
Thr Tyr Trp Cys Glu Val Phe Asn Pro Ile Ser Lys Asn
            395                 400                 405

CAA AGC GAC CCC ATC ATG CTG AAC GTA AAC TAT AAT GCT        1326
Gln Ser Asp Pro Ile Met Leu Asn Val Asn Tyr Asn Ala
                        410                 415

CTA CCA CAA GAA AAT GGC CTC TCA CCT GGG GCC ATT GCT        1365
Leu Pro Gln Glu Asn Gly Leu Ser Pro Gly Ala Ile Ala
        420                 425                 430

GGC ATT GTG ATT GGA GTA GTG GCC CTG GTT GCT CTG ATA        1404
Gly Ile Val Ile Gly Val Val Ala Leu Val Ala Leu Ile
                435                 440

GCA GTA GCC CTG GCA TGT TTT CTG CAT TTC GGG AAG ACC        1443
Ala Val Ala Leu Ala Cys Phe Leu His Phe Gly Lys Thr
445                 450                 455

GGC AGG GCA AGC GAC CAG CGT GAT CTC ACA GAG CAC AAA        1482
Gly Arg Ala Ser Asp Gln Arg Asp Leu Thr Glu His Lys
            460                 465                 470

CCC TCA GTC TCC AAC CAC ACT CAG GAC CAC TCC AAT GAC        1521
Pro Ser Val Ser Asn His Thr Gln Asp His Ser Asn Asp
                        475                 480

CCA CCT AAC AAG ATG AAT GAA GTT ACT TAT TCT ACC CTG        1560
Pro Pro Asn Lys Met Asn Glu Val Thr Tyr Ser Thr Leu
        485                 490                 495

AAC TTT GAA GCC CAG CAA CCC ACA CAA CCA ACT TCA GCC        1599
Asn Phe Glu Ala Gln Gln Pro Thr Gln Pro Thr Ser Ala
                500                 505

TCC CCA TCC CTA ACA GCC ACA GAA ATA ATT TAT TCA GAA        1638
Ser Pro Ser Leu Thr Ala Thr Glu Ile Ile Tyr Ser Glu
510                 515                 520

GTA AAA AAG CAG TAATGAAACC TGTCCTGCTC ACTGCAGTGC            1680
Val Lys Lys Gln
            525

TGATGTATTT CAAGTCTCTC ACCCTCATCA CTAGGAGATT                 1720

CCTTTCCCCT GTAGGGTAGA GGGGTGGGGA CAGAAACAAC                 1760

TTTCTCCTAC TCTTCCTTCC TAATAGGCAT CTCCAGGCTG                 1800

CCTGGTCACT GCCCCTCTCT CAGTGTCAAT AGATGAAAGT                 1840

ACATTGGGAG TCTGTAGGAA ACCCAACCTT CTTGTCATTG                 1880

AAATTTGGCA AAGCTGACTT TGGGAAAGAG GGACCAGAAC                 1920

TTCCCCTCCC TTCCCCTTTT CCCAACCTGG ACTTGTTTTA                 1960

AACTTGCCTG TTCAGAGCAC TCATTCCTTC CCACCCCCAG                 2000

TCCTGTCCTA TCACTCTAAT TCGGATTTGC CATAGCCTTG                 2040

AGGTAATGTC CTTTTCCATT AAGTACATGT GCCAGGAAAC                 2080

AGCGAGAGAG AGAAAGTAAA CGGCAGTAAT GCTTCTCCTA                 2120

TTTCTCCAAA GCCTTGTGTG AACTAGCAAA GAGAAGAAAA                 2160

TCAAATATAT AACCAATAGT GAAATGCCAC AGGTTTGTCC                 2200

ACTGTCAGGG TTGTCTACCT GTAGGATCAG GGTCTAAGCA                 2240

CCTTGGTGCT TAGCTAGAAT ACCACCTAAT CCTTCTGGCA                 2280

AGCCTGTCTT CAGAGAACCC ACTAGAAGCA ACTAGGAAAA                 2320

ATCACTTGCC AAAATCCAAG GCAATTCCTG ATGGAAAATG                 2360
```

-continued

| | |
|---|---|
| CAAAAGCACA TATATGTTTT AATATCTTTA TGGGCTCTGT | 2400 |
| TCAAGGCAGT GCTGAGAGGG AGGGGTTATA GCTTCAGGAG | 2440 |
| GGAACCAGCT TCTGATAAAC ACAATCTGCT AGGAACTTGG | 2480 |
| GAAAGGAAT CAGAGAGCTGC CCTTCAGCGA TTATTTAAAT | 2520 |
| TGTTAAAGAA TACACAATTT GGGGTATTGG GATTTTCTC | 2560 |
| CTTTTCTCTG AGACATTCCA CCATTTTAAT TTTTGTAACT | 2600 |
| GCTTATTTAT GTGAAAAGGG TTATTTTTAC TTAGCTTAGC | 2640 |
| TATGTCAGCC AATCCGATTG CCTTAGGTGA AAGAAACCAC | 2680 |
| CGAAATCCCT CAGGTCCCTT GGTCAGGAGC CTCTCAAGAT | 2720 |
| TTTTTTTGTC AGAGGCTCCA AATAGAAAAT AAGAAAAGGT | 2760 |
| TTTCTTCATT CATGGCTAGA GCTAGATTTA ACTCAGTTTC | 2800 |
| TAGGCACCTC AGACCAATCA TCAACTACCA TTCTATTCCA | 2840 |
| TGTTTGCACC TGTGCATTTT CTGTTTGCCC CCATTCACTT | 2880 |
| TGTCAGGAAA CCTTGGCCTC TGCTAAGGTG TATTTGGTCC | 2920 |
| TTGAGAAGTG GGAGCACCCT ACAGGGACAC TATCACTCAT | 2960 |
| GCTGGTGGCA TTGTTTACAG CTAGAAAGCT GCACTGGTGC | 3000 |
| TAATGCCCCT TGGGAAATGG GGCTGTGAGG AGGAGGATTA | 3040 |
| TAACTTAGGC CTAGCCTCTT TTAACAGCCT CTGAAATTTA | 3080 |
| TCTTTTCTTC TATGGGGTCT ATAAATGTAT CTTATAATAA | 3120 |
| AAAGGAAGGA CAGGAGGAAG ACAGGCAAAT GTACTTCTCA | 3160 |
| CCCAGTCTTC TACACAGATG GAATCTCTTT GGGGCTAAGA | 3200 |
| GAAAGGTTTT ATTCTATATT GCTTACCTGA TCTCATGTTA | 3240 |
| GGCCTAAGAG GCTTTCTCCA GGAGGATTAG CTTGGAGTTC | 3280 |
| TCTATACTCA GGTACCTCTT TCAGGGTTTT CTAACCCTGA | 3320 |
| CACGGACTGT GCATACTTTC CCTCATCCAT GCTGTGCTGT | 3360 |
| GTTATTTAAT TTTTCCTGGC TAAGATCATG TCTGAATTAT | 3400 |
| GTATGAAAAT TATTCTATGT TTTTATAATA AAAATAATAT | 3440 |
| ATCAGACATC GAAAAAAAAA A | 3461 |

(2) INFORMATION FOR SEQ ID NO: 7:

(i) SEQUENCE CHARACTERISTICS:
        (A) LENGTH: 1964 nucleotides
        (B) TYPE: nucleic acid
        (C) STRANDEDNESS: single
        (D) TOPOLOGY: linear (xi) SEQUENCE DESCRIPTION: SEQ ID NO: 7:

| | |
|---|---|
| CCGGGGGACA CGCAGGGCCA ACAGTCACAG CAGCCCTGAC | 40 |
| CAGAGCATTC CTGGAGCTCA AGCTCTCTAC AAAGAGGTGG | 80 |
| ACAGAGAAGA CAGCAGAGAC C ATG GGA CCC CCC TCA GCC<br>                                Met Gly Pro Pro Ser Ala<br>                                            -30 | 119 |
| CCT CCC TGC AGA TTG CAT GTC CCC TGG AAG GAG GTC CTG<br>Pro Pro Cys Arg Leu His Val Pro Trp Lys Glu Val Leu<br>   -25                          -20 | 158 |

| | | |
|---|---|---|
| CTC ACA GCC TCA CTT CTA ACC TTC TGG AAC CCA CCC ACC<br>Leu Thr Ala Ser Leu Leu Thr Phe Trp Asn Pro Pro Thr<br>-15                 -10                        -5 | | 197 |
| ACT GCC AAG CTC ACT ATT GAA TCC ACG CCA TTC AAT GTC<br>Thr Ala Lys Leu Thr Ile Glu Ser Thr Pro Phe Asn Val<br>     1                       5                         10 | | 236 |
| GCA GAG GGG AAG GAG GTT CTT CTA CTC GCC CAC AAC CTG<br>Ala Glu Gly Lys Glu Val Leu Leu Leu Ala His Asn Leu<br>              15                        20 | | 275 |
| CCC CAG AAT CGT ATT GGT TAC AGC TGG TAC AAA GGC GAA<br>Pro Gln Asn Arg Ile Gly Tyr Ser Trp Tyr Lys Gly Glu<br>25                    30                    35 | | 314 |
| AGA GTG GAT GGC AAC AGT CTA ATT GTA GGA TAT GTA ATA<br>Arg Val Asp Gly Asn Ser Leu Ile Val Gly Tyr Val Ile<br>       40                       45                    50 | | 353 |
| GGA ACT CAA CAA GCT ACC CCA GGG CCC GCA TAC AGT GGT<br>Gly Thr Gln Gln Ala Thr Pro Gly Pro Ala Tyr Ser Gly<br>                  55                          60 | | 392 |
| CGA GAG ACA ATA TAC CCC AAT GCA TCC CTG CTG ATC CAG<br>Arg Glu Thr Ile Tyr Pro Asn Ala Ser Leu Leu Ile Gln<br>     65                      70                    75 | | 431 |
| AAC GTC ACC CAG AAT GAC ACA GGA TTC TAC ACC CTA CAA<br>Asn Val Thr Gln Asn Asp Thr Gly Phe Tyr Thr Leu Gln<br>                  80                        85 | | 470 |
| GTC ATA AAG TCA GAT CTT GTG AAT GAA GAA GCA ACC GGA<br>Val Ile Lys Ser Asp Leu Val Asn Glu Glu Ala Thr Gly<br>90                    95                       100 | | 509 |
| CAG TTC CAT GTA TAC CCG GAG CTG CCC AAG CCC TCC ATC<br>Gln Phe His Val Tyr Pro Glu Leu Pro Lys Pro Ser Ile<br>             105                   110               115 | | 548 |
| TCC AGC AAC AAC TCC AAC CCC GTG GAG GAC AAG GAT GCT<br>Ser Ser Asn Asn Ser Asn Pro Val Glu Asp Lys Asp Ala<br>                 120                       125 | | 587 |
| GTG GCC TTC ACC TGT GAA CCT GAG GTT CAG AAC ACA ACC<br>Val Ala Phe Thr Cys Glu Pro Glu Val Gln Asn Thr Thr<br>130                   135                       140 | | 626 |
| TAC CTG TGG TGG GTA AAT GGT CAG AGC CTC CCG GTC AGT<br>Tyr Leu Trp Trp Val Asn Gly Gln Ser Leu Pro Val Ser<br>         145                     150 | | 665 |
| CCC AGG CTG CAG CTG TCC AAT GGC AAC AGG ACC CTC ACT<br>Pro Arg Leu Gln Leu Ser Asn Gly Asn Arg Thr Leu Thr<br>155                   160                       165 | | 704 |
| CTA CTC AGC GTC AAA AGG AAC GAT GCA GGA TCG TAT GAA<br>Leu Leu Ser Val Lys Arg Asn Asp Ala Gly Ser Tyr Glu<br>          170                   175               180 | | 743 |
| TGT GAA ATA CAG AAC CCA GCG AGT GCC AAC CGC AGT GAC<br>Cys Glu Ile Gln Asn Pro Ala Ser Ala Asn Arg Ser Asp<br>                 185                       190 | | 782 |
| CCA GTC ACC CTG AAT GTC CTC TAT GGC CCA GAT GGC CCC<br>Pro Val Thr Leu Asn Val Leu Tyr Gly Pro Asp Gly Pro<br>195                   200                       205 | | 821 |
| ACC ATT TCC CCC TCA AAG GCC AAT TAC CGT CCA GGG GAA<br>Thr Ile Ser Pro Ser Lys Ala Asn Tyr Arg Pro Gly Glu<br>          210                   215 | | 860 |
| AAT CTG AAC CTC TCC TGC CAC GCA GCC TCT AAC CCA CCT<br>Asn Leu Asn Leu Ser Cys His Ala Ala Ser Asn Pro Pro<br>220                   225                       230 | | 899 |
| GCA CAG TAC TCT TGG TTT ATC AAT GGG ACG TTC CAG CAA<br>Ala Gln Tyr Ser Trp Phe Ile Asn Gly Thr Phe Gln Gln<br>             235                   240               245 | | 938 |

```
TCC ACA CAA GAG CTC TTT ATC CCC AAC ATC ACT GTG AAT        977
Ser Thr Gln Glu Leu Phe Ile Pro Asn Ile Thr Val Asn
                250                 255

AAT AGC GGA TCC TAT ATG TGC CAA GCC CAT AAC TCA GCC        1016
Asn Ser Gly Ser Tyr Met Cys Gln Ala His Asn Ser Ala
    260                 265                 270

ACT GGC CTC AAT AGG ACC ACA GTC ACG ATG ATC ACA GTC        1055
Thr Gly Leu Asn Arg Thr Thr Val Thr Met Ile Thr Val
                275                 280

TCT GGA AGT GCT CCT GTC CTC TCA GCT GTG GCC ACC GTC        1094
Ser Gly Ser Ala Pro Val Leu Ser Ala Val Ala Thr Val
285                 290                 295

GGC ATC ACG ATT GGA GTG CTG GCC AGG GTG GCT CTG ATA        1133
Gly Ile Thr Ile Gly Val Leu Ala Arg Val Ala Leu Ile
                300                 305                 310

TAGCAGCCCT GGTGTATTTT CGATATTTCA GGAAGACTGG                1173

CAGATTGGAC CAGACCCTGA ATTCTTCTAG CTCCTCCAAT                1213

CCCATTTTAT CCCATGGAAC CACTAAAAAC AAGGTCTGCT                1253

CTGCTCCTGA AGCCCTATAT GCTGGAGATG ACAACTCAA                 1293

TGAAAATTTA AAGGAAAAAC CCTCAGCCCT GAGGTGTGTG                1333

CCACTCAGAG ACTTCACCTA ACTAGAGACA GGCAAACTGC                1373

AAACCANNCC TCTTTCGCTT GGCAGGATGA TGGTGTCATT                1413

AGTATTTCAC AAGAAGTAGC TTCAGAGGGT AACTTAACAG                1453

AGTATCAGAT CTATCTTGTC AATCCCAACG TTTTACATAA                1493

AATAAGCGAT CCTTTAGTGC ACCCAGTGAG TGACATTAGC                1533

AGCATCTTTA ACACAGCCGT GTGTTCAAGT GTACAGTGGT                1573

CCTTTTCAGA GTTGGNNNTA CTCCAACTGA AATGTTAAGG                1613

AAGAAGATAG ATCCAATTAA AAAAAATTAA AACCAATTTA                1653

AAAAAAAAAA AGAACACAGG AGATTCCAGT CTACTTGAGT                1693

TAGCATAATA CAGAAGTCCC CTCTACTTTA ACTTTTACAA                1733

AAAAGTAACC TGAACTAATC TGATGTTAAC CAATGTATTT                1773

ATTTGTCTGG TTCTGTTTCC TTGTTCCAAT TTGACAAAAC                1813

CCACTGTTCT TGTATTGTAT TGCCCAGGGG GAGCTATCAC                1853

TGTACTTGTA GAGTGGTGCT GCTTTAAGTT CATAAATCAC                1893

AAATAAAAGC CAATTAGCTC TATAACTAAA AAAAAAAAA                 1933

AAAAAAAAAA AAAAAAAAA AAAAAAAAA A                          1964
```

(2) INFORMATION FOR SEQ ID NO: 8:

(i) SEQUENCE CHARACTERISTICS:
        (A) LENGTH: 2009 nucleotides
        (B) TYPE:  nucleic acid
        (C) STRANDEDNESS: single
        (D) TOPOLOGY:  linear (xi) SEQUENCE DESCRIPTION: SEQ ID NO: 8:

```
ACAGCACAGC TGACAGCCGT ACTCAGGAAG CTTCTGGATC                40

CTAGGCTTAT CTCCACAGAG GAGAACACAC AAGCAGCAGA                80

GACC ATG GGG CCC CTC TCA GCC CCT CCC TGC ACA               114
     Met Gly Pro Leu Ser Ala Pro Pro Cys Thr
         5                  10
```

| | | |
|---|---|---|
| CAC CTC ATC ACT TGG AAG GGG GTC CTG CTC ACA GCA TCA<br>His Leu Ile Thr Trp Lys Gly Val Leu Leu Thr Ala Ser<br>15 20 | | 153 |
| CTT TTA AAC TTC TGG AAT CCG CCC ACA ACT GCC CAA GTC<br>Leu Leu Asn Phe Trp Asn Pro Pro Thr Thr Ala Gln Val<br>25 30 35 | | 192 |
| ACG ATT GAA GCC CAG CCA CCC AAA GTT TCT GAG GGG AAG<br>Thr Ile Glu Ala Gln Pro Pro Lys Val Ser Glu Gly Lys<br>40 45 50 | | 231 |
| GAT GTT CTT CTA CTT GTC CAC AAT TTG CCC CAG AAT CTT<br>Asp Val Leu Leu Leu Val His Asn Leu Pro Gln Asn Leu<br>55 60 65 | | 270 |
| GCT GGC TAC ATT TGG TAC AAA GGG CAA ATG ACA TAC GTC<br>Ala Gly Tyr Ile Trp Tyr Lys Gly Gln Met Thr Tyr Val<br>70 75 | | 309 |
| TAC CAT TAC ATT ACA TCA TAT GTA GTA GAC GGT CAA AGA<br>Tyr His Tyr Ile Thr Ser Tyr Val Val Asp Gly Gln Arg<br>80 85 90 | | 348 |
| ATT ATA TAT GGG CCT GCA TAC AGT GGA AGA GAA AGA GTA<br>Ile Ile Tyr Gly Pro Ala Tyr Ser Gly Arg Glu Arg Val<br>90 95 | | 387 |
| TAT TCC AAT GCA TCC CTG CTG ATC CAG AAT GTC ACG CAG<br>Tyr Ser Asn Ala Ser Leu Leu Ile Gln Asn Val Thr Gln<br>100 105 110 | | 426 |
| GAG GAT GCA GGA TCC TAC ACC TTA CAC ATC ATA AAG CGA<br>Glu Asp Ala Gly Ser Tyr Thr Leu His Ile Ile Lys Arg<br>115 120 125 | | 465 |
| CGC GAT GGG ACT GGA GGA GTA ACT GGA CAT TTC ACC TTC<br>Arg Asp Gly Thr Gly Gly Val Thr Gly His Phe Thr Phe<br>130 135 | | 504 |
| ACC TTA CAC CTG GAG ACT CCC AAG CCC TCC ATC TCC AGC<br>Thr Leu His Leu Glu Thr Pro Lys Pro Ser Ile Ser Ser<br>145 150 155 | | 543 |
| AGC AAC TTA AAT CCC AGG GAG GCC ATG GAG GCT GTG ATC<br>Ser Asn Leu Asn Pro Arg Glu Ala Met Glu Ala Val Ile<br>155 160 | | 582 |
| TTA ACC TGT GAT CCT GCG ACT CCA GCC GCA AGC TAC CAG<br>Leu Thr Cys Asp Pro Ala Thr Pro Ala Ala Ser Tyr Gln<br>170 175 180 | | 621 |
| TGG TGG ATG AAT GGT CAG AGC CTC CCT ATG ACT CAC AGG<br>Trp Trp Met Asn Gly Gln Ser Leu Pro Met Thr His Arg<br>180 185 190 | | 660 |
| TTG CAG CTG TCC AAA ACC AAC AGG ACC CTC TTT ATA TTT<br>Leu Gln Leu Ser Lys Thr Asn Arg Thr Leu Phe Ile Phe<br>195 200 | | 699 |
| GGT GTC ACA AAG TAT ATT GCA GGA CCC TAT GAA TGT GAA<br>Gly Val Thr Lys Tyr Ile Ala Gly Pro Tyr Glu Cys Glu<br>205 210 215 | | 738 |
| ATA CGG AAC CCA GTG AGT GCC AGC CGC AGT GAC CCA GTC<br>Ile Arg Asn Pro Val Ser Ala Ser Arg Ser Asp Pro Val<br>220 225 230 | | 777 |
| ACC CTG AAT CTC CTC CCA AAG CTG TCC AAG CCC TAC ATC<br>Thr Leu Asn Leu Leu Pro Lys Leu Ser Lys Pro Tyr Ile<br>235 240 | | 816 |
| ACA ATC AAC AAC TTA AAC CCC AGA GAG AAT AAG GAT GTC<br>Thr Ile Asn Asn Leu Asn Pro Arg Glu Asn Lys Asp Val<br>245 250 255 | | 855 |
| TTA ACC TTC ACC TGT GAA CCT AAG AGT GAG AAC TAC ACC<br>Leu Thr Phe Thr Cys Glu Pro Lys Ser Glu Asn Tyr Thr<br>260 265 | | 894 |

| | |
|---|---|
| TAC ATT TGG TGG CTA AAT GGT CAG AGC CTC CCT GTC AGT<br>Tyr Ile Trp Trp Leu Asn Gly Gln Ser Leu Pro Val Ser<br>270                        275                     280 | 933 |
| CCC AGG GTA AAG CGA CCC ATT GAA AAC AGG ATC CTC ATT<br>Pro Arg Val Lys Arg Pro Ile Glu Asn Arg Ile Leu Ile<br>              285                    290                    295 | 972 |
| CTA CCC AAT GTC ACG AGA AAT GAA ACA GGA CCT TAT CAA<br>Leu Pro Asn Val Thr Arg Asn Glu Thr Gly Pro Tyr Gln<br>                    300                    305 | 1011 |
| TGT GAA ATA CGG GAC CGA TAT GGT GGC ATC CGC AGT GAC<br>Cys Glu Ile Arg Asp Arg Tyr Gly Gly Ile Arg Ser Asp<br>310                        315                    320 | 1050 |
| CCA GTC ACC CTG AAT GTC CTC TAT GGT CCA GAC CTC CCC<br>Pro Val Thr Leu Asn Val Leu Tyr Gly Pro Asp Leu Pro<br>              325                    330 | 1089 |
| AGC ATT TAC CCT TCA TTC ACC TAT TAC CGT TCA GGA GAA<br>Ser Ile Tyr Pro Ser Phe Thr Tyr Tyr Arg Ser Gly Glu<br>335                        340                    345 | 1128 |
| AAC CTC TAC TTT TCC TGC TTC GGT GAG TCT AAC CCA CGG<br>Asn Leu Tyr Phe Ser Cys Phe Gly Glu Ser Asn Pro Arg<br>              350                    355                    360 | 1167 |
| GCA CAA TAT TCT TGG ACA ATT AAT GGG AAG TTT CAG CTA<br>Ala Gln Tyr Ser Trp Thr Ile Asn Gly Lys Phe Gln Leu<br>                    365                    370 | 1206 |
| TCA GGA CAA AAG CTC TCT ATC CCC CAA ATA ACT ACA AAG<br>Ser Gly Gln Lys Leu Ser Ile Pro Gln Ile Thr Thr Lys<br>375                        380                    385 | 1245 |
| CAT AGT GGG CTC TAT GCT TGC TCT GTT CGT AAC TCA GCC<br>His Ser Gly Leu Tyr Ala Cys Ser Val Arg Asn Ser Ala<br>              390                    395 | 1284 |
| ACT GGC AAG GAA AGC TCC AAA TCC ATC ACA GTC AAA GTC<br>Thr Gly Lys Glu Ser Ser Lys Ser Ile Thr Val Lys Val<br>405                        410                    415 | 1323 |
| TCT GAC TGG ATA TTA CCC TGAATTCTAC TAGTTCCTCC<br>Ser Asp Trp Ile Leu Pro<br>                    420 | 1361 |
| AATTCCATTT TCTCCCATGG AATCACGAAG AGCAAGACCC | 1401 |
| ACTCTGTTCC AGAAGCCCTA TAATCTGGAG GTGGACAACT | 1441 |
| CGATGTAAAT TCATGGGAA ACCCTTGTA CCTGACATGT | 1481 |
| GAGCCACTCA GAACTCACCA AAATGTTCGA CACCATAACA | 1521 |
| ACAGCTACTC AAACTGTAAA CCAGGATAAG AAGTTGATGA | 1561 |
| CTTCACACTG TGGACAGTTT TTCAAAGATG TCATAACAAG | 1601 |
| ACTCCCCATC ATGACAAGGC TCCACCCTCT ACTGTCTGCT | 1641 |
| CATGCCTGCC TCTTTCACTT GGCAGGATAA TGCAGTCATT | 1681 |
| AGAATTTCAC ATGTAGTAGC TTCTGAGGGT AACAACAGAG | 1721 |
| TGTCAGATAT GTCATCTCAA CCTCAAACTT TTACGTAACA | 1761 |
| TCTCAGGGAA ATGTGGCTCT CTCCATCTTG CATACAGGGC | 1801 |
| TCCCAATAGA AATGAACACA GAGATATTGC CTGTGTGTTT | 1841 |
| GCAGAGAAGA TGGTTTCTAT AAAGAGTAGG AAAGCTGAAA | 1881 |
| TTATAGTAGA GTCTCCTTTA AATGCACATT GTGTGGATGG | 1921 |
| CTCTCACCAT TTCCTAAGAG ATACAGTGTA AAAACGTGAC | 1961 |
| AGTAATACTG ATTCTAGCAG AATAAACATG TACCACATTT | 2001 |

| | | |
|---|---|---|
| GCAAAAAA | | 2009 |

(2) INFORMATION FOR SEQ ID NO: 9:

(i) SEQUENCE CHARACTERISTICS:
        (A) LENGTH: 1591 nucleotides
        (B) TYPE: nucleic acid
        (C) STRANDEDNESS: single
        (D) TOPOLOGY: linear (xi) SEQUENCE DESCRIPTION: SEQ ID NO: 9:

```
GGGTGGATCC TAGGCTCATC TCCATAGGGG AGAACACACA                              40

TACAGCAGAG ACC ATG GGA CCC CTC TCA GCC CCT CCC TGC                       80
               Met Gly Pro Leu Ser Ala Pro Pro Cys
                                 5

ACT CAG CAC ATC ACC TGG AAG GGG CTC CTG CTC ACA GCA                     119
Thr Gln His Ile Thr Trp Lys Gly Leu Leu Leu Thr Ala
 10              15                  20

TCA CTT TTA AAC TTC TGG AAC CTG CCC ACC ACT GCC CAA                     158
Ser Leu Leu Asn Phe Trp Asn Leu Pro Thr Thr Ala Gln
         25                  30                  35

GTA ATA ATT GAA GCC CAG CCA CCC AAA GTT TCT GAG GGG                     197
Val Ile Ile Glu Ala Gln Pro Pro Lys Val Ser Glu Gly
                 40                  45

AAG GAT GTT CTT CTA CTT GTC CAC AAT TTG CCC CAG AAT                     236
Lys Asp Val Leu Leu Leu Val His Asn Leu Pro Gln Asn
 50                  55                  60

CTT ACT GGC TAC ATC TTG TAC AAA GGG CAA ATG ACG GAC                     275
Leu Thr Gly Tyr Ile Leu Tyr Lys Gly Gln Met Thr Asp
         65                  70

CTC TAC CAT TAC ATT ACA TCA TAT GTA GTA GAC GGT CAA                     314
Leu Tyr His Tyr Ile Thr Ser Tyr Val Val Asp Gly Gln
 75                  80                  85

ATT ATA TAT GGG CCT GCC TAC AGT GGA CGA GAA ACA GTA                     353
Ile Ile Tyr Gly Pro Ala Tyr Ser Gly Arg Glu Thr Val
                 90                  95                 100

TAT TCC AAT GCA TCC CTG CTG ATC CAG AAT GTC ACA CAG                     392
Tyr Ser Asn Ala Ser Leu Leu Ile Gln Asn Val Thr Gln
                105                 110

GAG GAT GCA GGA TCC TAC ACC TTA CAC ATC ATA AAG CGA                     431
Glu Asp Ala Gly Ser Tyr Thr Leu His Ile Ile Lys Arg
115                 120                 125

GGC GAT GGG ACT GGA GGA GTA ACT GGA TAT TTC ACT GTC                     470
Gly Asp Gly Thr Gly Gly Val Thr Gly Tyr Phe Thr Val
                130                 135

ACC TTA TAC TCG GAG ACT CCC AAG CGC TCC ATC TCC AGC                     509
Thr Leu Tyr Ser Glu Thr Pro Lys Arg Ser Ile Ser Ser
140                 145                 150

AGC AAC TTA AAC CCC AGG GAG GTC ATG GAG GCT GTG CGC                     548
Ser Asn Leu Asn Pro Arg Glu Val Met Glu Ala Val Arg
                155                 160                 165

TTA ATC TGT GAT CCT GAG ACT CCG GAT GCA AGC TAC CTG                     587
Leu Ile Cys Asp Pro Glu Thr Pro Asp Ala Ser Tyr Leu
                170                 175

TGG TTG CTG AAT GGT CAG AAC CTC CCT ATG ACT CAC AGG                     626
Trp Leu Leu Asn Gly Gln Asn Leu Pro Met Thr His Arg
                180                 185                 190

TTG CAG CTG TCC AAA ACC AAC AGG ACC CTC TAT CTA TTT                     665
Leu Gln Leu Ser Lys Thr Asn Arg Thr Leu Tyr Leu Phe
                195                 200
```

| | | |
|---|---|---|
| GGT GTC ACA AAG TAT ATT GCA GGG CCC TAT GAA TGT GAA<br>Gly Val Thr Lys Tyr Ile Ala Gly Pro Tyr Glu Cys Glu<br>205                 210                 215 | | 704 |
| ATA CGG AGG GGA GTG AGT GCC AGC CGC AGT GAC CCA GTC<br>Ile Arg Arg Gly Val Ser Ala Ser Arg Ser Asp Pro Val<br>        220                 225                 230 | | 743 |
| ACC CTG AAT CTC CTC CCG AAG CTG CCC ATG CCT TAC ATC<br>Thr Leu Asn Leu Leu Pro Lys Leu Pro Met Pro Tyr Ile<br>                235                 240 | | 782 |
| ACC ATC AAC AAC TTA AAC CCC AGG GAG AAG AAG GAT GTG<br>Thr Ile Asn Asn Leu Asn Pro Arg Glu Lys Lys Asp Val<br>245                 250                 255 | | 821 |
| TTA GCC TTC ACC TGT GAA CCT AAG AGT CGG AAC TAC ACC<br>Leu Ala Phe Thr Cys Glu Pro Lys Ser Arg Asn Tyr Thr<br>        260                 265 | | 860 |
| TAC ATT TGG TGG CTA AAT GGT CAG AGC CTC CCG GTC AGT<br>Tyr Ile Trp Trp Leu Asn Gly Gln Ser Leu Pro Val Ser<br>270                 275                 280 | | 899 |
| CCG AGG GTA AAG CGA CCC ATT GAA AAC AGG ATA CTC ATT<br>Pro Arg Val Lys Arg Pro Ile Glu Asn Arg Ile Leu Ile<br>                285                 290                 295 | | 938 |
| CTA CCC AGT GTC ACG AGA AAT GAA ACA GGA CCC TAT CAA<br>Leu Pro Ser Val Thr Arg Asn Glu Thr Gly Pro Tyr Gln<br>                300                 305 | | 977 |
| TGT GAA ATA CGG GAC CGA TAT GGT GGC ATC CGC AGT AAC<br>Cys Glu Ile Arg Asp Arg Tyr Gly Gly Ile Arg Ser Asn<br>310                 315                 320 | | 1016 |
| CCA GTC ACC CTG AAT GTC CTC TAT GGT CCA GAC CTC CCC<br>Pro Val Thr Leu Asn Val Leu Tyr Gly Pro Asp Leu Pro<br>                325                 330 | | 1055 |
| AGA ATT TAC CCT TAC TTC ACC TAT TAC CGT TCA GGA GAA<br>Arg Ile Tyr Pro Tyr Phe Thr Tyr Tyr Arg Ser Gly Glu<br>335                 340                 345 | | 1094 |
| AAC CTC GAC TTG TCC TGC TTT GCG GAC TCT AAC CCA CCG<br>Asn Leu Asp Leu Ser Cys Phe Ala Asp Ser Asn Pro Pro<br>        350                 355                 360 | | 1133 |
| GCA GAG TAT TTT TGG ACA ATT AAT GGG AAG TTT CAG CTA<br>Ala Glu Tyr Phe Trp Thr Ile Asn Gly Lys Phe Gln Leu<br>                365                 370 | | 1172 |
| TCA GGA CAA AAG CTC TTT ATC CCC CAA ATT ACT ACA AAT<br>Ser Gly Gln Lys Leu Phe Ile Pro Gln Ile Thr Thr Asn<br>375                 380                 385 | | 1211 |
| CAT AGC GGG CTC TAT GCT TGC TCT GTT CGT AAC TCA GCC<br>His Ser Gly Leu Tyr Ala Cys Ser Val Arg Asn Ser Ala<br>                390                 395 | | 1250 |
| ACT GGC AAG GAA ATC TCC AAA TCC ATG ATA GTC AAA GTC<br>Thr Gly Lys Glu Ile Ser Lys Ser Met Ile Val Lys Val<br>400                 405                 410 | | 1289 |
| TCT GGT CCC TGC CAT GGA AAC CAG ACA GAG TCT CAT<br>Ser Gly Pro Cys His Gly Asn Gln Thr Glu Ser His<br>        415                 420 | | 1325 |
| TAATGGCTGC CACAATAGAG ACACTGAGAA AAAGAACAGG | | 1365 |
| TTGATACCTT CATGAAATTC AAGACAAAGA AGAAAAAGGC | | 1405 |
| TCAATGTTAT TGGACTAAAT AATCAAAAGG ATAATGTTTT | | 1445 |
| CATAATTTTT ATTGGAAAAT GTGCTGATTC TTGGAATGTT | | 1485 |
| TTATTCTCCA GATTTATGAA CTTTTTTTCT TCAGCAATTG | | 1525 |
| GTAAAGTATA CTTTTGTAAA CAAAAATTGA AACATTTGCT | | 1565 |

-continued

```
TTTGCTCTCT ATCTGAGTGC CCCCCC                                           1591

(2) INFORMATION FOR SEQ ID NO: 10:

(i) SEQUENCE CHARACTERISTICS:
        (A) LENGTH: 12 nucleotides
        (B) TYPE:  nucleic acid
        (C) STRANDEDNESS: single
        (D) TOPOLOGY:  linear (xi) SEQUENCE DESCRIPTION: SEQ ID NO: 10:

GCTCCTTGTA AG                                                          12

(2) INFORMATION FOR SEQ ID NO: 11:

(i) SEQUENCE CHARACTERISTICS:
        (A) LENGTH: 12 nucleotides
        (B) TYPE:  nucleic acid
        (C) STRANDEDNESS: single
        (D) TOPOLOGY:  linear (xi) SEQUENCE DESCRIPTION: SEQ ID NO: 11:

GCT GGT TGT AAG                                                        12
Ala Gly Cys Lys (2) INFORMATION FOR SEQ ID NO: 12:

(i) SEQUENCE CHARACTERISTICS:
        (A) LENGTH: 12 nucleotides
        (B) TYPE:  nucleic acid
        (C) STRANDEDNESS: single
        (D) TOPOLOGY:  linear (xi) SEQUENCE DESCRIPTION: SEQ ID NO: 12:

G CTG GTT GTA AG                                                       12
  Leu Val Val (2) INFORMATION FOR SEQ ID NO: 13:

(i) SEQUENCE CHARACTERISTICS:
        (A) LENGTH: 12 nucleotides
        (B) TYPE:  nucleic acid
        (C) STRANDEDNESS: single
        (D) TOPOLOGY:  linear (xi) SEQUENCE DESCRIPTION: SEQ ID NO: 13:

GC TGG TTG TAAG                                                        12
   Trp Leu (2) INFORMATION FOR SEQ ID NO: 14:

(i) SEQUENCE CHARACTERISTICS:
        (A) LENGTH: 10 nucleotides
        (B) TYPE:  nucleic acid
        (C) STRANDEDNESS: single
        (D) TOPOLOGY:  linear (xi) SEQUENCE DESCRIPTION: SEQ ID NO: 14:

GGGCCCTTAA                                                             60
```

ANTIBODY PREPARATIONS SPECIFICALLY BINDING TO UNIQUE DETERMINANTS OF CEA ANTIGENS OR FRAGMENTS THEREOF AND USE OF THE ANTIBODY PREPARATIONS IN IMMUNOASSAYS

CROSS-REFERENCES TO RELATED APPLICATIONS

This application is a divisional, of application Ser. No. 08/027,974, filed Mar. 8, 1993, which is a divisional of Ser. No. 07/760,031, filed Sep. 13, 1992 issued to U.S. Pat. No. 5,231,009; which is a division of Ser. No. 07/274,107, filed Nov. 21, 1988 issued to U.S. Pat. No. 5,122,599; which is a CIP of Ser. No. 07/207,678 filed Jun. 16, 1988. now abandoned; which is a CIP of Ser. No. 07/060,031 filed Jun. 19, 1987. now abandoned; which is a CIP of Ser. No. 07/016,683 filed Feb. 19, 1987. now abandoned; which is a CIP of Ser. No. 06/896,361 filed Aug. 13, 1986, now abandoned.

BACKGROUND OF THE INVENTION

1. Field of the Invention

The present invention concerns nucleic acid sequences which code for carcinoembryonic antigen (CEA) antigen family peptide sequences.

2. Background Information

Carcinoembryonic antigen was first described by Gold and Freedman, *J. Exp. Med.,* 121, 439–462, (1965). CEA is characterized as a glycoprotein of approximately 200,000 molecular weight with 50–60% by weight of carbohydrate. CEA is present during normal human fetal development, but only in very low concentration in the normal adult intestinal tract. It is produced and secreted by a number of different tumors.

CEA is a clinically useful tumor marker for the management of colorectal cancer patients. CEA can be measured using sensitive immunoassay methods. When presurgical serum levels of CEA are elevated, a postsurgical drop in serum CEA to the normal range typically indicates successful resection of the tumor. Postsurgical CEA levels that do riot return to normal often indicate incomplete resection of the tumor or the presence of additional tumor sites in the patient. After returning to normal levels, subsequent rapid rises in serum CEA levels usually indicate the presence of metastages. Slower postsurgical rises from the normal level are most often interpreted to indicate the presence of new primary tumors not previously detected. Post surgical management of colon cancer patients is thus facilitated by the measurement of CEA.

CEA is a member of an antigen family. Because of this, the immunoassay of CEA by presently available methods is complicated by the fact that CEA is but one of several potentially reactive antigens. There have been at least sixteen CEA-like antigens described in the literature. Since some of these appear to be the same antigen described by different investigators, the actual number of different antigens is somewhat less than this number. Nonetheless, there is a complex array of cross-reactive antigens which can potentially interfere with an immunoassay of the CEA released by tumors. It is known that serum levels of CEA-like antigens are elevated in many non-cancerous conditions such an inflammatory liver diseases and also in smokers. It is important that immunoassays used for the monitoring of cancer patient status not be interfered with by these other CEA-like antigens. Conversely, it is important to be able to distinguish the antigens by immunoassays because of the possibility that different tumor types may preferentially express different forms of CEA. If so, then the ability to reliably measure the different forms of CEA can provide the means to diagnose or more successfully treat different forms of cancer.

The members of the "CEA family" share some antigenic determinants. These common epitopes are not useful in distinguishing the members of the antigen family and antibodies recognizing them are of little use for measuring tumor-specific CEA levels.

U.S. Pat. No. 3,663,684, entitled "Carcinoembryonic Antigen and Diagnostic Method Using Radioactive Iodine", concerns purification and radioiodination of CEA for use in a RIA.

U.S. Pat. No. 3,697,638 describes that CEA is a mixture of antigens (components A and B in this case). U.S. Pat. No. 3,697,638 mentions methods for separating and radioiodinating each component and their use in specific RIA'S.

U.S. Pat. No. 3,852,415, entitled "Compositions for Use in Radioimmunoassay, as Substitute for Blood Plasma Extract in Determination of Carcinoembryonic Antigen" relates to the use of a buffer containing EDTA and bovine serum albumin as a substitute for plasma as a diluent for CEA RIA's.

U.S. Pat. No. 3,867,363, entitled "Carcinoembryonic Antigens", is directed to the isolation of CEA components A and B, their labelling and use in a RIA.

U.S. Pat. No. 3,927,193, entitled "Localization of Tumors by Radiolabelled Antibodies", concerns the use of radiolabelled anti-CEA antibodies in whole body tumor imaging.

U.S. Pat. No. 3,956,258, entitled "Carcinoembryonic Antigens", relates to the isolation of CEA components A and B.

U.S. Pat. No. 4,086,217, entitled "Carcinoembryonic Antigens", is directed to the isolation of CEA components A and B.

U.S. Pat. No. 4,140,753, entitled "Diagnostic Method and Reagent", concerns the purification of a CEA isomer called CEA-Si and its use in a RIA.

U.S. Pat. No. 4,145,336, entitled "Carcinoembryonic Antigen Isomer", relates to the antigen CEA-S1.

U.S. Pat. No. 4,180,499, entitled "Carcinoembryonic Antigens", describes a process for producing CEA component B.

U.S. Pat. No. 4,228,236, entitled "Process of Producing Carcinoembryonic Antigen", is directed to the use of the established cell lines LS-174T and LS-180 or clones or derivatives thereof for the production of CEA.

U.S. Pat. No. 4,272,504, entitled "Antibody Adsorbed Support Method for Carcinoembryonic Antigen Assay", concerns two concepts for the radioimmunoassay of CEA. First, U.S. Pat. No. 4,272,504 relates to a sample pretreatment in the form of heating to 65 to 85° C. at pH 5 to precipitate and eliminate extraneous protein. Second, it describes the use of a solid phase antibody (either on beads or tubes) as a means to capture analyte and radiolabelled CEA tracer.

U.S. Pat. No. 4,299,815, entitled "Carcinoembryonic Antigen Determination", concerns diluting a CEA sample with water and pretreating by heating to a temperature below which precipitation of protein will occur. The pretreated sample is then immunoassayed using RIA, EIA, FIA or chemiluminescent immunoassay.

U.S. Pat. No. 4,349,528, entitled "Monoclonal Hybridoma Antibody Specific for High Molecular Weight Carcinoembryonic Antigen", is directed to a monoclonal antibody reacting with 180 kD CEA, but not with other molecular weight forms.

U.S. Pat. No. 4,467,031, entitled "Enzyme-Immunoassay for Carcinoembryonic Antigen", relates to a sandwich enzyme immunoassay for CEA in which the first of two anti-CEA monoclonal antibodies is attached to a solid phase and the second monoclonal is conjugated with peroxidase.

U.S. Pat. No. 4,489,167, entitled "Methods and Compositions for Cancer Detection", describes that CEA shares an antigenic determinant with alpha-acid glycoprotein (AG), which is a normal component of human serum. The method described therein concerns a solid-phase sandwich enzyme immunoassay using as one antibody an antibody recognizing AG and another antibody recognizing CEA, but not AG.

U.S. Pat. No. 4,578,349, entitled "Immunoassay for Carcinoembryonic Antigen (CEA)", is directed to the use of high salt containing buffers as diluents in CEA immunoassays.

EP 113072-A, entitled "Assaying Blood Sample for Carcinoembryonic Antigen—After Removal of Interfering Materials by Incubation with Silica Gel", relates to the removal from a serum of a plasma sample of interfering substances by pretreatment with silica gel. The precleared sample is then subjected to an immunoassay.

EP 102008-A, entitled "Cancer Diagnostics Carcinoembryonic Antigen—Produced from Perchloric Acid Extracts Without Electrophoresis", relates to a procedure for the preparation of CEA from perchloric acid extracts, without the use of an electrophoresis step.

EP 92223-A, entitled "Determination of Carcinoembryonic Antigen in Cytosol or Tissue—for Therapy Control and Early Recognition of Regression", concerns an immunoassay of CEA, not in serum or plasma, but in the cytosol fraction of the tumor tissue itself.

EP 83103759.6, entitled "Cytosole-CEA-Measurement as Predictive Test in Carcinoma, Particularly Mammacarcinoma", is similar to EP 92223-A.

EP 83303759, entitled "Monoclonal Antibodies Specific to Carcinoembryonic Antigen", relates to the production of "CEA specific" monoclonal antibodies and their use in immunoassays.

WO 84/02983, entitled "Specific CEA-Family Antigens, Antibodies Specific Thereto and Their Methods of Use", is directed to the use of monoclonal antibodies to CEA-meconium (MA)-, and NCA-specific epitopes in immunoassays designed to selectively measure each of these individual components in a sample.

All of the heretofore CEA assays utilize either monoclonal or polyclonal antibodies which are generated by immunizing animals with the intact antigen of choice. None of them address the idea of making sequence specific antibodies for the detection of a unique primary sequence of the various antigens. They do not cover the use of any primary amino acid sequence for the production of antibodies to synthetic peptides or fragments of the natural product. They do not include the concept of using primary amino acid sequences to distinguish the CEA family members. None of them covers the use of DNA or RNA clones for isolating the genes with which to determine the primary sequence.

DEFINITIONS

| Nucleic Acid Abbreviations | |
| --- | --- |
| A | adenine |
| G | guanine |
| C | cytosine |
| T | thymidine |
| U | uracil |
| Amino Acid Abbreviations: | |
| Asp | aspartic acid |
| Asn | asparagine |
| Thr | threonine |
| Ser | serine |
| Glu | glutamic acid |
| Gln | glutamine |
| Pro | proline |
| Gly | glycine |
| Ala | alanine |
| Cys | cysteine |
| Val | valine |
| Met | methionine |
| Ile | isoleucine |
| Leu | leucine |
| Tyr | tyrosine |
| Phe | phenylalanine |
| Trp | tryptophan |
| Lys | lysine |
| His | histidine |
| Arg | arginine |

Nucleotide—A monomeric unit of DNA or RNA containing a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C and uracil ("U").

DNA Sequence—A linear array of nucleotides connected one to the other by phosphodiester bonds between the 3' and 5' carbons of adjacent pentoses.

Functional equivalents—It is well known in the art that in a DNA sequence some nucleotides can be replaced without having an influence on the sequence of the expression product. With respect to the peptide this term means that one or more amino acids which have no function in a particular use can be deleted or replaced by another one.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during translation of mRNA into amino acid sequences. During translation, the proper reading frame must be maintained. For example, the sequence GCTGGTTGTAAG SEQ ID NO: 10 may be translated in three reading frames or phases, each of which affords a different amino acid sequence GCT GGT TGT AAG—Ala-Gly-Cys-Lys SEQ ID NO: 11

G CTG GTT GTA AG—Leu-Val-Val SEQ ID NO: 12

GC TGG TTG TAA G—Trp-Leu-(STOP) SEQ ID NO: 13.

Polypeptide—A linear array of amino acids connected one to the other by peptide bonds between the alpha-amino and carboxy groups of adjacent amino acids.

Genome—The entire DNA of a cell or a virus. It includes inter alia the structural genes coding for the polypeptides of the cell or virus, as well as its operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus, many of which consist of DNA sequences encapsulated in a protein envelope or coat ("capsid protein").

Cloning Vehicle—A plasmid, phage DNA or other DNA sequence which is capable of replicating in a host cell, which is characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein. cDNA Expression Vector—A procaroytic cloning vehicle which also contains sequences of nucleotides that facilitate expression of cDNA sequences in eucaroytic cells. These nucleotides include sequences that function as eucaryotic promoter, alternative splice sites and polyadenylation signals.

Transformation/Transfection—DNA or RNA is introduced into cells in such a way as to allow gene expression. "Infected" referred to herein concerns the introduction of RNA or DNA by a viral vector into the host.

"Injected" referrred to herein concerns the microinjection (use of a small syringe) of DNA into a cell.

CEA antigen family (CEA gene family)—a set of genes (gene family) and their products (antigen family) that share nucleotide sequences homologous to partial cDNA LV-7 (CEA-(a)) and as a result of theses similarities also share a subset of their antigenic epitopes. Examples of the CEA antigen family include CEA (=CEA-(b)), transmembrane CEA (TMCEA)=CEA-(c) and normal crossreacting antigen NCA (=CEA-(d)).

SUMMARY OF THE INVENTION

The present invention concerns the following DNA sequences designated as TM-2 (CEA-(e)), TM-3 (CEA-(f)), TM-4 (CEA-(g)), KGCEAl and KGCEA2, which code for CEA antigen family peptide sequences or nucleic acids having a base sequence (DNA or RNA) that are hybridizable therewith:

```
              SEQUENCE AND TRANSLATION OF cDNA OF TM-2           (SEQ ID NO:1)
          10                     30                   50
           .                      .                    .
     CAGCCGTGCTCGAAGCGTTCCTGGAGCCCAAGCTCTCCTCCACAGGTGAAGACAGGGCCA 70                     90                   110
           .                      .                    .
     GCAGGAGACACCATGGGGCACCTCTCAGCCCCACTTCACAGAGTGCGTGTACCCTGGCAG
                  MetGlyHisLeuSerAlaProLeuHisArgValArgValProTrpGln 130                    150                  170
           .                      .                    .
     GGGCTTCTGCTCACAGCCTCACTTCTAACCTTCTGGAACCCGCCCACCACTGCCCAGCTC
     GlyLeuLeuLeuThrAlaSerLeuLeuThrPheTrpAsnProProThrThrAlaGlnLeu 190                    210                  230
           .                      .                    .
     ACTACTGAATCCATGCCATTCAATGTTGCAGAGGGGAAGGAGGTTCTTCTCCTTGTCCAC
     ThrThrGluSerMetProPheAsnValAlaGluGlyLysGluValLeuLeuLeuValHis 250                    270                  290
           .                      .                    .
     AATCTGCCCCAGCAACTTTTTGGCTACAGCTGGTACAAAGGGAAAGAGTGGATGGCAAC
     AsnLeuProGlnGlnLeuPheGlyTyrSerTrpTyrLysGlyGluArgValAspGlyAsn 310                    330                  350
           .                      .                    .
     CGTCAAATTGTAGGATATGCAATAGGAACTCAACAAGCTACCCCAGGGCCCGCAAACAGC
     ArgGlnIleValGlyTyrAlaIleGlyThrGlnGlnAlaThrProGlyProAlaAsnSer 370                    390                  410
           .                      .                    .
     GGTCGAGAGACAATATACCCCAATGCATCCCTGCTGATCCAGAACGTCACCCAGAATGAC
```

-continued

GlyArgGluThrIleTyrProAsnAlaSerLeuLeuIleGlnAsnValThrGlnAsnAsp

```
          430            450            470
            .              .              .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490            510            530
            .              .              .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550            570            590
            .              .              .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610            630            650
            .              .              .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670            690            710
            .              .              .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730            750            770
            .              .              .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790            810            830
            .              .              .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850            870            890
            .              .              .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910            930            950
            .              .              .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970            990           1010
            .              .              .
TATACCTGCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030           1050           1070
            .              .              .
ATAGTCACTGATAATGCTCTACCACAAGAAAATGGCCTCTCACCTGGGGCCATTGCTGGC
IleValThrAspAsnAlaLeuProGlnGluAsnGlyLeuSerProGlyAlaIleAlaGly 1090           1110           1130
            .              .              .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150           1170           1190
            .              .              .
CATTTCGGGAAGACCGGCAGGGCAAGCGACCAGCGTGATCTCACAGAGCACAAACCCTCA
HisPheGlyLysThrGlyArgAlaSerAspGlnArgAspLeuThrGluHisLysProSer 1210           1230           1250
            .              .              .
GTCTCCAACCACACTCAGGACCACTCCAATGACCCACCTAACAAGATGAATGAAGTTACT
ValSerAsnHisThrGlnAspHisSerAsnAspProProAsnLysMetAsnGluValThr 1270           1290           1310
            .              .              .
TATTCTACCCTGAACTTTGAAGCCCAGCAACCCACACAACCAACTTCAGCCTCCCCATCC
TyrSerThrLeuAsnPheGluAlaGlnGlnProThrGlnProThrSerAlaSerProSer 1330           1350           1370
            .              .              .
CTAACAGCCACAGAAATAATTTATTCAGAAGTAAAAAAGCAGTAATGAAACCTGTCCTGC
LeuThrAlaThrGluIleIleTyrSerGluValLysLysGln
```

```
              1390          1410          1430
               .             .             .
TCACTGCAGTGCTGATGTATTTCAAGTCTCTCACCCTCATCACTAGGAGATTCCTTTCCC 1450          1470          1490
               .             .             .
CTGTAGGGTAGAGGGGTGGGGACAGAAACAACTTTCTCCTACTCTTCCTTCCTAATAGGC 1510          1530          1550
               .             .             .
ATCTCCAGGCTGCCTGGTCACTGCCCCTCTCTCAGTGTCAATAGATGAAAGTACATTGGG 1570          1590          1610
               .             .             .
AGTCTGTAGGAAACCCAACCTTCTTGTCATTGAAATTTGGCAAAGCTGACTTTGGGAAAG 1630          1650          1670
               .             .             .
AGGGACCAGAACTTCCCCTCCCTTCCCCTTTTCCCAACCTGGACTTGTTTTAAACTTGCC 1690          1710          1730
               .             .             .
TGTTCAGAGCACTCATTCCTTCCCACCCCCAGTCCTGTCCTATCACTCTAATTCGGATTT 1750          1770          1790
               .             .             .
GCCATAGCCTTGAGGTTATGTCCTTTTCCATTAAGTACATGTGCCAGGAAACAGCGAGAG 1810          1830          1850
               .             .             .
AGAGAAAGTAAACGGCAGTAATGCTTCTCCTATTTCTCCAAAGCCTTGTGTGAACTAGCA 1870          1890          1910
               .             .             .
AAGAGAAGAAAATCAAATATATAACCAATAGTGAAATGCCACAGGTTTGTCCACTGTCAG 1930          1950          1970
               .             .             .
GGTTGTCTACCTGTAGGATCAGGGTCTAAGCACCTTGGTGCTTAGCTAGAATACCACCTA 1990          2010          2030
               .             .             .
ATCCTTCTGGCAAGCCTGTCTTCAGAGAACCCACTAGAAGCAACTAGGAAAAATCACTTG 2050          2070          2090
               .             .             .
CCAAAATCCAAGGCAATTCCTGATGGAAAATGCAAAAGCACATATATGTTTTAATATCTT 2110          2130          2150
               .             .             .
TATGGGCTCTGTTCAAGGCAGTGCTGAGAGGGAGGGGTTATAGCTTCAGGAGGGAACCAG 2170          2190          2210
               .             .             .
CTTCTGATAAACACAATCTGCTAGGAACTTGGGAAAGGAATCAGAGAGCTGCCCTTCAGC 2230          2250          2270
               .             .             .
GATTATTTAAATTGTTAAAGAATACACAATTTGGGGTATTGGGATTTTTCTCCTTTTCTC 2290          2310          2330
               .             .             .
TGAGACATTCCACCATTTTAATTTTTGTAACTGCTTATTTATGTGAAAAGGGTTATTTTT 2350          2370          2390
               .             .             .
ACTTAGCTTAGCTATGTCAGCCAATCCGATTGCCTTAGGTGAAAGAAACCACCGAAATCC 2410          2430          2450
               .             .             .
CTCAGGTCCCTTGGTCAGGAGCCTCTCAAGATTTTTTTTGTCAGAGGCTCCAAATAGAAA 2470          2490          2510
               .             .             .
ATAAGAAAAGGTTTTCTTCATTCATGGCTAGAGCTAGATTTAACTCAGTTTCTAGGCACC 2530          2550          2570
               .             .             .
TCAGACCAATCATCAACTACCATTCTATTCCATGTTTGCACCTGTGCATTTTCTGTTTGC
```

```
          2590           2610           2630
            .              .              .
CCCCATTCACTTTGTCAGGAAACCTTGGCCTCTGCTAAGGTGTATTTGGTCCTTGAGAAG 2650           2670           2690
            .              .              .
TGGGAGCACCCTACAGGGACACTATCACTCATGCTGGTGGCATTGTTTACAGCTAGAAAG 2710           2730           2750
            .              .              .
CTGCACTGGTGCTAATGCCCCTTGGGAAATGGGGCTGTGAGGAGGAGGATTATAACTTAG 2770           2790           2810
            .              .              .
GCCTAGCCTCTTTTAACAGCCTCTGAAATTTATCTTTTCTTCTATGGGGTCTATAAATGT 2830           2850           2870
            .              .              .
ATCTTATAATAAAAAGGAAGGACAGGAGGAAGACAGGCAAATGTACTTCTCACCCAGTCT 2890           2910           2930
            .              .              .
TCTACACAGATGGAATCTCTTTGGGGCTAAGAGAAAGGTTTTATTCTATATTGCTTACCT 2950           2970           2990
            .              .              .
GATCTCATGTTAGGCCTAAGAGGCTTTCTCCAGGAGGATTAGCTTGGAGTTCTCTATACT 3010           3030           3050
            .              .              .
CAGGTACCTCTTTCAGGGTTTTCTAACCCTGACACGGACTGTGCATACTTTCCCTCATCC 3070           3090           3110
            .              .              .
ATGCTGTGCTGTGTTATTTAATTTTTCCTGGCTAAGATCATGTCTGAATTATGTATGAAA 3130           3150           3170
            .              .              .
ATTATTCTATGTTTTTATAATAAAAATAATATATCAGACATCGAAAAAAAAAA

SEQUENCE AND TRANSLATION OF cDNA OF TM-3         (SEQ ID NO:2)
          10             30             50
            .              .              .
CAGCCGTGCTCGAAGCGTTCCTGGAGCCCAAGCTCTCCTCCACAGGTGAAGACAGGGCCA 70             90             110
            .              .              .
GCAGGAGACACCATGGGGCACCTCTCAGCCCCACTTCACAGAGTGCGTGTACCCTGGCAG
             MetGlyHisLeuSerAlaProLeuHisArgValArgValProTrpGln 130            150            170
            .              .              .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190            210            230
            .              .              .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250            270            290
            .              .              .
AATCTGCCCCAGCAACTTTTTGGCTACAGCTGGTACAAAGGGGAAAGAGTGGATGGCAAC
AsnLeuProGluGlnLeuPheGlyTyrSerTrpTyrLysGlyGluArgValAspGlyAsn 250            270            290
            .              .              .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310            330            350
            .              .              .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370            390            410
            .              .              .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430            450            470
```

```
                                      490                 510                 530
                                       .                   .                   .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 550                 570                 590
                                       .                   .                   .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 610                 630                 650
                                       .                   .                   .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 670                 690                 710
                                       .                   .                   .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 730                 750                 770
                                       .                   .                   .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 790                 810                 830
                                       .                   .                   .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 850                 870                 890
                                       .                   .                   .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 910                 930                 950
                                       .                   .                   .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 970                 990                1010
                                       .                   .                   .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 1030                1050                1070
                                       .                   .                   .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1090                1110                1130
                                       .                   .                   .
ATAGTCACTGAGCTAAGTCCAGTAGTAGCAAAGCCCCAAATCAAAGCCAGCAAGACCACA
IleValThrGluLeuSerProValValAlaLysProGlnIleLysAlaSerLysThrThr 1150                1170                1190
                                       .                   .                   .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer 1210                1230                1250
                                       .                   .                   .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1270                1290                1310
                                       .                   .                   .
GGCAACACCACCCTCAGCATAAACCCTGTCAAGAGGGAGGATGCTGGGACGTATTGGTGT
GlyAsnThrThrLeuSerIleAsnProValLysArgGluAspAlaGlyThrTyrTrpCys 1330                1350                1370
                                       .                   .                   .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1390                1410                1430
                                       .                   .                   .
AATGCTCTACCACAAGAAAATGGCCTCTCACCTGGGGCCATTGCTGGCATTGTGATTGGA
AsnAlaLeuProGlnGluAsnGlyLeuSerProGlyAlaIleAlaGlyIleValIleGly
```

-continued

```
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450          1470          1490
         .    .    .    .    .    .    .
ACCGGCAGCTCAGGACCACTCCAATGACCCACCTAACAAGATGAATGAAGTTACTTATTC
ThrGlySerSerGlyProLeuGln 1510          1530          1550
         .    .    .    .    .    .    .
TACCCTGAACTTTGAAGCCCAGCAACCCACACAACCAACTTCAGCCTCCCCATCCCTAAC 1570          1590          1610
         .    .    .    .    .    .    .
AGCCACAGAAATAATTTATTCAGAAGTAAAAAAGCAGTAATGAAACCTGAAAAAAAAAAA

1630
         .
AAAAAAAAAA

SEQUENCE AND TRANSLATION OF cDNA OF TM-4       (SEQ ID NO:3)
         10            30            50
         .    .    .    .    .    .    .
CAGCCGTGCTCGAAGCGTTCCTGGAGCCCAAGCTCTCCTCCACAGGTGAAGACAGGGCCA 70            90           110
         .    .    .    .    .    .    .
GCAGGAGACACCATGGGCACCTCTCAGCCCCACTTCACAGAGTGCGTGTACCCTGGCAG
              MetGlyHisLeuSerAlaProLeuHisArgValArgValProTrpGln 130           150           170
         .    .    .    .    .    .    .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190           210           230
         .    .    .    .    .    .    .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250           270           290
         .    .    .    .    .    .    .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310           330           350
         .    .    .    .    .    .    .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer 370           390           410
         .    .    .    .    .    .    .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430           450           470
         .    .    .    .    .    .    .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490           510           530
         .    .    .    .    .    .    .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550           570           590
         .    .    .    .    .    .    .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610           630           650
         .    .    .    .    .    .    .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670           690           710
         .    .    .    .    .    .    .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730           750           770
```

-continued

```
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790              810              830
           .                .                .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850              870              890
           .                .                .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910              930              950
           .                .                .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970              990             1010
           .                .                .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030             1050             1070
           .                .                .
ATAGTCACTGATAATGCTCTACCACAAGAAAATGGCCTCTCACCTGGGGCCATTGCTGGC
IleValThrAspAsnAlaLeuProGlnGluAsnGlyLeuSerProGlyAlaIleAlaGly 1090             1110             1130
           .                .                .
ATTGTGATTGGAGTAGTGGCCCTGGTTGCTCTGATAGCAGTAGCCCTGGCATGTTTTCTG
IleValIleGlyValValAlaLeuValAlaLeuIleAlaValAlaLeuAlaCysPheLeu 1150             1170             1190
           .                .                .
CATTTCGGGAAGACCGGCAGCTCAGGACCACTCCAATGACCCACCTAACAAGATGAATGA
HisPheGlyLysThrGlySerSerGlyProLeuGln 1210             1230             1250
           .                .                .
AGTTACTTATTCTACCCTGAACTTTGAAGCCCAGCAACCCACACAACCAACTTCAGCCTC 1270             1290             1310
           .                .                .
CCCATCCCTAACAGCCACAGAAATAATTTATTCAGAAGTAAAAAAGCAGTAATGAAACCT

1330
           .
GAAAAAAAAAAAAAAAAAA
```

The present invention is also directed to a replicable recombinant cloning vehicle ("vector") having an insert comprising a nucleic acid, e.g., DNA, which comprises a base sequence which codes for a CEA peptide or a base sequence hybridizable therewith.

This invention also relates to a cell that is transformed/transfected, infected or injected with the above described replicable recombinant cloning vehicle or nucleic acid hybridizable with the aforementioned cDNA. Thus the invention also concerns the transfection of cells using free nucleic acid, without the use of a cloning vehicle.

Still further, the present invention concerns a polypeptide expressed by the above described transfected, infected or injected cell, which polypeptide exhibits immunological cross-reactivity with a CEA, as well as labelled forms of the polypeptide. The invention also relates to polypeptides having an amino acid sequence, i.e., synthetic peptides, or the expression product of a cell that is transfected, injected, infected with the above described replicable recombinant cloning vehicles, as well as labelled forms thereof. Stated otherwise, the present invention concerns a synthetic peptide having an amino acid sequence corresponding to the entire amino acid sequence or a portion thereof having no less than five amino acids of the aforesaid expression product.

The invention further relates to an antibody preparation specific for the above described polypeptide.

Another aspect of the invention concerns an immunoassay method for detecting CEA or a functional equivalent thereof in a test sample comprising (a) contacting the sample with the above described antibody preparation, and (b) determining binding thereof to CEA in the sample.

The invention also is directed to a nucleic acid hybridization method for detecting a CEA or a related nucleic acid (DNA or RNA) sample in a test sample comprising (a) contacting the test sample with a nucleic acid probe comprising a nucleic acid, which comprises a base sequence which codes for a CEA peptide sequence or a base sequence that is hybridizable therewith, and (b) determining the formation of the resultant hybridized probe.

The present invention also concerns a method for detecting the presence of carcinoembryonic antigen or a functional equivalent thereof in an animal or human patient in vivo comprising a) introducing into said patient a labeled (e.g., a radio-opaque material that can be detected by X-rays, radio-labeled or labeled with paramagnetic materials that can be detected by NMR) antibody preparation according to the present invention and b) detecting the presence of such antibody preparation in the patient by detecting the label.

In another aspect, the present invention relates to the use of an antibody preparation according to the present invention for therapeutic purposes, namely, attaching to an antibody preparation radionuclides, toxins or other biological effectors to form a complex and introducing an effective amount of such complex into an animal or human patient, e.g., by injection or orally. The antibody complex would attach to CEA in a patient and the radionuclide, toxin or other biological effector would serve to destroy the CEA expressing cell.

DETAILED DESCRIPTION OF THE INVENTION

Figure 1A:
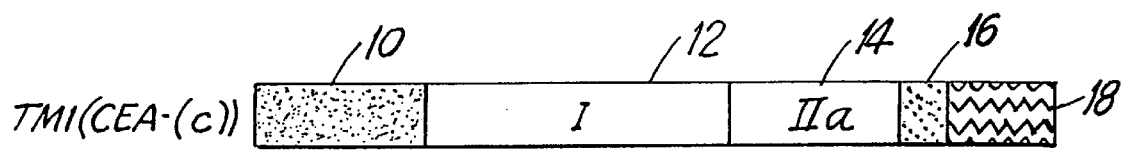
FIG. 1 is a schematic representation of the transmembrane CEA's

In parent applications, applicants described the following CEA's:

|  |  | ATCC No. |
|---|---|---|
| CEA-(a) | partial CEA (pcLV7) |  |
| CEA-(b) | full coding CEA (pc 15LV7) | 67709 |
| CEA-(c) | TM-1 (FL-CEA; pc 19–22) | 67710 |
| CEA-(d) | NCA (pcBT 20) | 67711 |

In the present application, applicants described the following CEA's:

|  |  | ATTC No. |
|---|---|---|
| CEA-(e) | TM-2 (pc E22) | 67712 |
| CEA-(f) | TM-3 (pc HT-6) | 67708 |
| CEA-(g) | TM-4. |  |

ATCC Nos. 67708, 67709, 67710, 67711 and 67712 were all deposited with the American Type Culture Collection on May 25, 1988.

The sequences for CEA-(a), CEA-(b), CEA-(c) and CEA-(d) are given hereinbelow:

```
CEA-(a) (SEQ ID NO:4):

GG GGT TTA CAC AAC CAC CAC CCC ATC AAA CCC TTC ATC ACC AGC AAC AAC TCC AAC CCC GTG

GAG GAT GAG GAT GCT GTA GCC TTA ACC TGT GAA CCT GAG ATT CAG AAC ACA ACC TAC CTG

TGG TGG GTA AAT AAT CAG AGC CTC CCG GTC AGT CCC AGG CTG CAG CTG TCC AAT GAC AAC

AGG ACC CTC ACT CTA CTC AGT GTC ACA AGG AAT GAT GTA GGA CCC TAT GAG TGT GGA ATC

CAG AAC GAA TTA AGT GTT GAC CAC AGC GAC CCA GTC ACC AGG CGA TTC CTC TAT GGC CCA

GAC GAC CCC ACC ATT TCC CCC TCA TAC ACC TAT TAC CGT CCA GGG GTG GAA CCT CAG CCT

CTC TGC CAT GCA GCC TCT AAC CCA CCT GCA CAG TAT TCT TGG CTG ATT GAT GGG ACC GTC

CAG CAA CAC ACA CAA GAG CTC TTT ATC TCC AAC ATC ACT GAG AAG AAC AGC GGA CTC TAT

ACC TGC CAG GCC AAT AAC TCA GCC AGT GGC ACA GCA GGA CTA CAG TCA AGA CAA TCA CAG

TCT CTG CGG ATG CCC AAG CCC TCC ATC TCC AGC AAC AAC TCC AAA CCC GTG GAG GAC AAG

GAT CGC TGT GGC CTT CAC TGT GAA CCT GAG GCT CAG AAC ACA ACC TAC CTG TGG TGG GTA

AAT GGT CAG AGC CTC CCA GTC AGT CCC AGG CTG CAG CTG TCC AAT GGC AAC AGG ACC CTC

ACT CTA TTC AAT GTC ACA AGA AAT GAC GCA AGA GCC TAT GTA TGT GGA ATC CAG AAC TCA

GTG AGT GCA AAC CGC AGT GAC CCA GTC ACC CTG GAT GTC CTC TAT GGG CCG GAC ACC CCC

ATC ATT TCC CCC CCC CC

CEA-(b) (SEQ ID NO:5):

10                   30                   50
                 .                    .                    .
     CACCATGGAGTCTCCCTCGGCCCCTCCCCACAGATGGTGCATCCCCTGGCAGAGGCTCCTG
         MetGluSerProSerAlaProProHisArgTrpCysIleProTrpGlnArgLeuLeu 70                   90                  110
                 .                    .                    .
     CTCACAGCCTCACTTCTAACCTTCTGGAACCCGCCCACCACTGCCAAGCTCACTATTGAA
         LeuThrAlaSerLeuLeuThrPheTrpAsnProProThrThrAlaLysLeuThrIleGlu 130                  150                  170
                 .                    .                    .
     TCCACGCCGTTCAATGTCGCAGAGGGGAAGGAGGTGCTTCTACTTGTCCACAATCTGCCC
         SerThrProPheAsnValAlaGluGlyLysGluValLeuLeuLeuValHisAsnLeuPro 190                  210                  230
```

-continued

```
CAGCATCTTTTTGGCTACAGCTGGTACAAAGGTGAAAGAGTGGATGGCAACCGTCAAATT
GlnHisLeuPheGlyTyrSerTrpTyrLysGlyGluArgValAspGlyAsnArgGlnIle 250                 270                 290
            .                   .                   .
ATAGGATATGTAATAGGAACTCAACAAGCTACCCCAGGGCCCGCATACAGTGGTCGAGAG
IleGlyTyrValIleGlyThrGlnGlnAlaThrProGlyProAlaTyrSerGlyArgGlu 310                 330                 350
            .                   .                   .
ATAATATACCCCAATGCATCCCTGCTGATCCAGAACATCATCCAGAATGACACAGGATTC
IleIleTyrProAsnAlaSerLeuLeuIleGlnAsnIleIleGlnAsnAspThrGlyPhe 370                 390                 410
            .                   .                   .
TACACCCTACACGTCATAAAGTCAGATCTTGTGAATGAAGAAGCAACTGGCCAGTTCCGG
TyrThrLeuHisValIleLysSerAspLeuValAsnGluGluAlaThrGlyGlnPheArg 430                 450                 470
            .                   .                   .
GTATACCCGGAGCTGCCCAAGCCCTCCATCTCCAGCAACAACTCCAAACCCGTGGAGGAC
ValTyrProGluLeuProLysProSerIleSerSerAsnAsnSerLysProValGluAsp 490                 510                 530
            .                   .                   .
AAGGATGCTGTGGCCTTCACCTGTGAACCTGAGACTCAGGACGCAACCTACCTGTGGTGG
LysAspAlaValAlaPheThrCysGluProGluThrGlnAspAlaThrTyrLeuTrpTrp 550                 570                 590
            .                   .                   .
GTAAACAATCAGAGCCTCCCGGTCAGTCCCAGGCTGCAGCTGTCCAATGGCAACAGGACC
ValAsnAsnGlnSerLeuProValSerProArgLeuGlnLeuSerAsnGlyAsnArgThr 610                 630                 650
            .                   .                   .
CTCACTCTATTCAATGTCACAAGAAATGACACAGCAAGCTACAAATGTGAAACCCAGAAC
LeuThrLeuPheAsnValThrArgAsnAspThrAlaSerTyrLysCysGluThrGlnAsn 670                 690                 710
            .                   .                   .
CCAGTGAGTGCCAGGCGCAGTGATTCAGTCATCCTGAATGTCCTCTATGGCCCGGATGCC
ProValSerAlaArgArgSerAspSerValIleLeuAsnValLeuTyrGlyProAspAla 730                 750                 770
            .                   .                   .
CCCACCATTTCCCCTCTAAACACATCTTACAGATCAGGGGAAAATCTGAACCTCTCCTGC
ProThrIleSerProLeuAsnThrSerTyrArgSerGlyGluAsnLeuAsnLeuSerCys 790                 810                 830
            .                   .                   .
CACGCAGCCTCTAACCCACCTGCACAGTACTCTTGGTTTGTCAATGGGACTTTCCAGCAA
HisAlaAlaSerAsnProProAlaGlnTyrSerTrpPheValAsnGlyThrPheGlnGln 850                 870                 890
            .                   .                   .
TCCACCCAAGAGCTCTTTATCCCCAACATCACTGTGAATAATAGTGGATCCTATACGTGC
SerThrGlnGluLeuPheIleProAsnIleThrValAsnAsnSerGlySerTyrThrCys 910                 930                 950
            .                   .                   .
CAAGCCCATAACTCAGACACTGGCCTCAATAGGACCACAGTCACGACGATCACAGTCTAT
GlnAlaHisAsnSerAspThrGlyLeuAsnArgThrThrValThrThrIleThrValTyr 970                 990                1010
            .                   .                   .
GCAGAGCCACCCAAACCCTTCATCACCAGCAACAACTCCAACCCCGTGGAGGATGAGGAT
AlaGluProProLysProPheIleThrSerAsnAsnSerAsnProValGluAspGluAsp 1030                1050                1070
            .                   .                   .
GCTGTAGCCTTAACCTGTGAACCTGAGATTCAGAACACAACCTACCTGTGGTGGGTAAAT
AlaValAlaLeuThrCysGluProGluIleGlnAsnThrThrTyrLeuTrpTrpValAsn 1090                1110                1130
            .                   .                   .
AATCAGAGCCTCCCGGTCAGTCCCAGGCTGCAGCTGTCCAATGACAACAGGACCCTCACT
AsnGlnSerLeuProValSerProArgLeuGlnLeuSerAsnAspAsnArgThrLeuThr 1150                1170                1190
            .                   .                   .
```

```
                                -continued
CTACTCAGTGTCACAAGGAATGATGTAGGACCCTATGAGTGTGGAATCCAGAACGAATTA
LeuLeuSerValThrArgAsnAspValGlyProTyrGluCysGlyIleGlnAsnGluLeu 1210           1230           1250
           .              .              .
AGTGTTGACCACAGCGACCCAGTCATCCTGAATGTCCTCTATGGCCCAGACGACCCCACC
SerValAspHisSerAspProValIleLeuAsnValLeuTyrGlyProAspAspProThr 1270           1290           1310
           .              .              .
ATTTCCCCCTCATACACCTATTACCGTCCAGGGGTGAACCTCAGCCTCTCCTGCCATGCA
IleSerProSerTyrThrTyrTyrArgProGlyValAsnLeuSerLeuSerCysHisAla 1330           1350           1370
           .              .              .
GCCTCTAACCCACCTGCACAGTATTCTTGGCTGATTGATGGGAACATCCAGCAACACACA
AlaSerAsnProProAlaGlnTyrSerTrpLeuIleAspGlyAsnIleGlnGlnHisThr 1390           1410           1430
           .              .              .
CAAGAGCTCTTTATCTCCAACATCACTGAGAAGAACAGCGGACTCTATACCTGCCAGGCC
GlnGluLeuPheIleSerAsnIleThrGluLysAsnSerGlyLeuTyrThrCysGlnAla 1450           1470           1490
           .              .              .
AATAACTCAGCCAGTGGCCACAGCAGGACTACAGTCAAGACAATCACAGTCTCTGCGGAG
AsnAsnSerAlaSerGlyHisSerArgThrThrValLysThrIleThrValSerAlaGlu 1510           1530           1550
           .              .              .
CTGCCCAAGCCCTCCATCTCCAGCAACAACTCCAAACCCGTGGAGGACAAGGATGCTGTG
LeuProLysProSerIleSerSerAsnAsnSerLysProValGluAspLysAspAlaVal 1570           1590           1610
           .              .              .
GCCTTCACCTGTGAACCTGAGGCTCAGAACACAACCTACCTGTGGTGGGTAAATGGTCAG
AlaPheThrCysGluProGluAlaGlnAsnThrThrTyrLeuTrpTrpValAsnGlyGln 1630           1650           1670
           .              .              .
AGCCTCCCAGTCAGTCCCAGGCTGCAGCTGTCCAATGGCAACAGGACCCTCACTCTATTC
SerLeuProValSerProArgLeuGlnLeuSerAsnGlyAsnArgThrLeuThrLeuPhe 1690           1710           1730
           .              .              .
AATGTCACAAGAAATGACGCAAGAGCCTATGTATGTGGAATCCAGAACTCAGTGAGTGCA
AsnValThrArgAsnAspAlaArgAlaTyrValCysGlyIleGlnAsnSerValSerAla 1750           1770           1790
           .              .              .
AACCGCAGTGACCCAGTCACCCTGGATGTCCTCTATGGGCCGGACACCCCCATCATTTCC
AsnArgSerAspProValThrLeuAspValLeuTyrGlyProAspThrProIleIleSer 1810           1830           1850
           .              .              .
CCCCCAGACTCGTCTTACCTTTCGGGAGCGAACCTCAACCTCTCCTGCCACTCGGCCTCT
ProProAspSerSerTyrLeuSerGlyAlaAsnLeuAsnLeuSerCysHisSerAlaSer 1870           1890           1910
           .              .              .
AACCCATCCCCGCAGTATTCTTGGCGTATCAATGGGATACCGCAGCAACACACACAAGTT
AsnProSerProGlnTyrSerTrpArgIleAsnGlyIleProGlnGlnHisThrGlnVal 1930           1950           1970
           .              .              .
CTCTTTATCGCCAAAATCACGCCAAATAATAACGGGACCTATGCCTGTTTTGTCTCTAAC
LeuPheIleAlaLysIleThrProAsnAsnAsnGlyThrTyrAlaCysPheValSerAsn 1990           2010           2030
           .              .              .
TTGGCTACTGGCCGCAATAATTCCATAGTCAAGAGCATCACAGTCTCTGCATCTGGAACT
LeuAlaThrGlyArgAsnAsnSerIleValLysSerIleThrValSerAlaSerGlyThr 2050           2070           2090
           .              .              .
TCTCCTGGTCTCTCAGCTGGGGCCACTGTCGGCATCATGATTGGAGTGCTGGTTGGGGTT
SerProGlyLeuSerAlaGlyAlaThrValGlyIleMetIleGlyValLeuValGlyVal 2110           2130           2150
           .              .              .
GCTCTGATATAGCAGCCCTGGTGTAGTTTCTTCATTTCAGGAAGACTGACAGTTGTTTTG
```

-continued

AlaLeuIleEnd

```
         2170              2190              2210
          .                 .                 .
CTTCTTCCTTAAAGCATTTGCAACAGCTACAGTCTAAAATTGCTTCTTTACCAAGGATAT 2230              2250              2270
          .                 .                 .
TTACAGAAAAGACTCTGACCAGAGATCGAGACCATCCTAGCCAACATCGTGAAACCCCAT 2290              2310              2330
          .                 .                 .
CTCTACTAAAAATACAAAAATGAGCTGGGCTTGGTGGCGCGCACCTGTAGTCCCAGTTAC 2350              2370              2390
          .                 .                 .
TCGGGAGGCTGAGGCAGGAGAATCGCTTGAACCCGGGAGGTGGAGATTGCAGTGAGCCCA 2410              2430              2450
          .                 .                 .
GATCGCACCACTGCACTCCAGTCTGGCAACAGAGCAAGACTCCATCTCAAA
```

```
      2460       2470       2480       2490       2500
       *          *          *          *          *
 AAG AAA AGA AAA GAA GAC TCT GAC CTG TAC TCT TGA ATA CAA GTT TCT GAT ACC ACT
2510       2520       2530       2540       2550       2560
 *          *          *          *          *          *
 GCA CTG TCT GAG AAT TTC CAA AAC TTT AAT GAA CTA ACT GAC AGC TTC ATG AAA CTG
2570       2580       2590       2600       2610       2620
 *          *          *          *          *          *
 TCC ACC AAG ATC AAG CAG AGA AAA TAA TTA ATT TCA TGG GGA CTA AAT GAA CTA ATG
2630       2640       2650       2660       2670       2680
 *          *          *          *          *          *
 AGG ATA ATA TTT TCA TAA TTT TTT ATT TGA AAT TTT GCT GAT TCT TTA AAT GTC TTG
2690       2700       2710       2720       2730
 *          *          *          *          *
 TTT CCC AGA TTT CAG GAA ACT TTT TTT CTT TTA AGC TAT CCA CTC TTA CAG CAA TTT
2740       2750       2760       2770       2780       2790
 *          *          *          *          *          *
 GAT AAA ATA TAC TTT TGT GAA CAA AAA TTG AGA CAT TTA CAT TTT ATC CCT ATG TGG
2800       2810       2820       2830
 *          *          *          *
 TCG CTC CAG ACT TGG GAA ACT ATT CAT GAA TAT TTA TAT TGT ATG
```

CEA-(c) (SEQ ID NO:6):

```
           10                30                50
            .                 .                 .
CAGCCGTGCTCGAAGCGTTCCTGGAGCCCAAGCTCTCCTCCACAGGTGAAGACAGGGCCA 70                90               110
            .                 .                 .
GCAGGAGACACCATGGGGCACCTCTCAGCCCCACTTCACAGAGTGCGTGTACCCTGGCAG
          MetGlyHisLeuSerAlaProLeuHisArgValArgValProTrpGln 130               150               170
            .                 .                 .
GGGCTTCTGCTCACAGCCTCACTTCTAACCTTCTGGAACCCGCCCACCACTGCCCAGCTC
GlyLeuLeuLeuThrAlaSerLeuLeuThrPheTrpAsnProProThrThrAlaGlnLeu 190               210               230
            .                 .                 .
ACTACTGAATCCATGCCATTCAATGTTGCAGAGGGGAAGGAGGTTCTTCTCCTTGTCCAC
ThrThrGluSerMetProPheAsnValAlaGluGlyLysGluValLeuLeuLeuValHis 250               270               290
            .                 .                 .
AATCTGCCCCAGCAACTTTTTGGCTACAGCTGGTACAAAGGGGAAAGAGTGGATGGCAAC
AsnLeuProGlnGlnLeuPheGlyTyrSerTrpTyrLysGlyGluArgValAspGlyAsn 310               330               350
            .                 .                 .
CGTCAAATTGTAGGATATGCAATAGGAACTCAACAAGCTACCCCAGGGCCCGCAAACAGC
ArgGlnIleValGlyTyrAlaIleGlyThrGlnGlnAlaThrProGlyProAlaAsnSer
```

-continued

```
           370                 390                 410
            .                   .                   .
GGTCGAGAGACAATATACCCCAATGCATCCCTGCTGATCCAGAACGTCACCCAGAATGAC
GlyArgGluThrIleTyrProAsnAlaSerLeuLeuIleGlnAsnValThrGlnAsnAsp 430                 450                 470
            .                   .                   .
ACAGGATTCTACACCCTACAAGTCATAAAGTCAGATCTTGTGAATGAAGAAGCAACTGGA
ThrGlyPheTyrThrLeuGlnValIleLysSerAspLeuValAsnGluGluAlaThrGly 490                 510                 530
            .                   .                   .
CAGTTCCATGTATACCCGGAGCTGCCCAAGCCCTCCATCTCCAGCAACAACTCCAACCCT
GlnPheHisValTyrProGluLeuProLysProSerIleSerSerAsnAsnSerAsnPro 550                 570                 590
            .                   .                   .
GTGGAGGACAAGGATGCTGTGGCCTTCACCTGTGAACCTGAGACTCAGGACACAACCTAC
ValGluAspLysAspAlaValAlaPheThrCysGluProGluThrGlnAspThrThrTyr 610                 630                 650
            .                   .                   .
CTGTGGTGGATAAACAATCAGAGCCTCCCGGTCAGTCCCAGGCTGCAGCTGTCCAATGGC
LeuTrpTrpIleAsnAsnGlnSerLeuProValSerProArgLeuGlnLeuSerAsnGly 670                 690                 710
            .                   .                   .
AACAGGACCCTCACTCTACTCAGTGTCACAAGGAATGACACAGGACCCTATGAGTGTGAA
AsnArgThrLeuThrLeuLeuSerValThrArgAsnAspThrGlyProTyrGluCysGlu 730                 750                 770
            .                   .                   .
ATACAGAACCCAGTGAGTGCGAACCGCAGTGACCCAGTCACCTTGAATGTCACCTATGGC
IleGlnAsnProValSerAlaAsnArgSerAspProValThrLeuAsnValThrTyrGly 790                 810                 830
            .                   .                   .
CCGGACACCCCCACCATTTCCCCTTCAGACACCTATTACCGTCCAGGGGCAAACCTCAGC
ProAspThrProThrIleSerProSerAspThrTyrTyrArgProGlyAlaAsnLeuSer 850                 870                 890
            .                   .                   .
CTCTCCTGCTATGCAGCCTCTAACCCACCTGCACAGTACTCCTGGCTTATCAATGGAACA
LeuSerCysTyrAlaAlaSerAsnProProAlaGlnTyrSerTrpLeuIleAsnGlyThr 910                 930                 950
            .                   .                   .
TTCCAGCAAAGCACACAAGAGCTCTTTATCCCTAACATCACTGTGAATAATAGTGGATCC
PheGlnGlnSerThrGlnGluLeuPheIleProAsnIleThrValAsnAsnSerGlySer 970                 990                1010
            .                   .                   .
TATACCTGCCACGCCAATAACTCAGTCACTGGCTGCAACAGGACCACAGTCAAGACGATC
TyrThrCysHisAlaAsnAsnSerValThrGlyCysAsnArgThrThrValLysThrIle 1030                1050                1070
            .                   .                   .
ATAGTCACTGAGCTAAGTCCAGTAGTAGCAAAGCCCCAAATCAAAGCCAGCAAGACCACA
IleValThrGluLeuSerProValValAlaLysProGlnIleLysAlaSerLysThrThr 1090                1110                1130
            .                   .                   .
GTCACAGGAGATAAGGACTCTGTGAACCTGACCTGCTCCACAAATGACACTGGAATCTCC
ValThrGlyAspLysAspSerValAsnLeuThrCysSerThrAsnAspThrGlyIleSer 1150                1170                1190
            .                   .                   .
ATCCGTTGGTTCTTCAAAAACCAGAGTCTCCCGTCCTCGGAGAGGATGAAGCTGTCCCAG
IleArgTrpPhePheLysAsnGlnSerLeuProSerSerGluArgMetLysLeuSerGln 1210                1230                1250
            .                   .                   .
GGCAACACCACCCTCAGCATAAACCCTGTCAAGAGGGAGGATGCTGGGACGTATTGGTGT
GlyAsnThrThrLeuSerIleAsnProValLysArgGluAspAlaGlyThrTyrTrpCys 1270                1290                1310
            .                   .                   .
GAGGTCTTCAACCCAATCAGTAAGAACCAAAGCGACCCCATCATGCTGAACGTAAACTAT
GluValPheAsnProIleSerLysAsnGlnSerAspProIleMetLeuAsnValAsnTyr 1330                1350                1370
```

```
                    .              .              .              .
AATGCTCTACCACAAGAAAATGGCCTCTCACCTGGGGCCATTGCTGGCATTGTGATTGGA
AsnAlaLeuProGlnGluAsnGlyLeuSerProGlyAlaIleAlaGlyIleValIleGly 1390           1410           1430
            .              .              .              .
GTAGTGGCCCTGGTTGCTCTGATAGCAGTAGCCCTGGCATGTTTTCTGCATTTCGGGAAG
ValValAlaLeuValAlaLeuIleAlaValAlaLeuAlaCysPheLeuHisPheGlyLys 1450           1470           1490
            .              .              .              .
ACCGGCAGGGCAAGCGACCAGCGTGATCTCACAGAGCACAAACCCTCAGTCTCCAACCAC
ThrGlyArgAlaSerAspGlnArgAspLeuThrGluHisLysProSerValSerAsnHis 1510           1530           1550
            .              .              .              .
ACTCAGGACCACTCCAATGACCCACCTAACAAGATGAATGAAGTTACTTATTCTACCCTG
ThrGlnAspHisSerAsnAspProProAsnLysMetAsnGluValThrTyrSerThrLeu 1570           1590           1610
            .              .              .              .
AACTTTGAAGCCCAGCAACCCACACAACCAACTTCAGCCTCCCCATCCCTAACAGCCACA
AsnPheGluAlaGlnGlnProThrGlnProThrSerAlaSerProSerLeuThrAlaThr 1630           1650           1670
            .              .              .              .
GAAATAATTTATTCAGAAGTAAAAAAGCAGTAATGAAACCTGTCCTGCTCACTGCAGTGC
GluIleIleTyrSerGluValLysLysGln 1690           1710           1730
            .              .              .              .
TGATGTATTTCAAGTCTCTCACCCTCATCACTAGGAGATTCCTTTCCCCTGTAGGGTAGA 1750           1770           1790
            .              .              .              .
GGGGTGGGGACAGAAACAACTTTCTCCTACTCTTCCTTCCTAATAGGCATCTCCAGGCTG 1810           1830           1850
            .              .              .              .
CCTGGTCACTGCCCCTCTCTCAGTGTCAATAGATGAAAGTACATTGGGAGTCTGTAGGAA 1870           1890           1910
            .              .              .              .
ACCCAACCTTCTTGTCATTGAAATTTGGCAAAGCTGACTTTGGGAAAGAGGGACCAGAAC 1930           1950           1970
            .              .              .              .
TTCCCCTCCCTTCCCCTTTTCCCAACCTGGACTTGTTTTAAACTTGCCTGTTCAGAGCAC 1990           2010           2030
            .              .              .              .
TCATTCCTTCCCACCCCCAGTCCTGTCCTATCACTCTAATTCGGATTTGCCATAGCCTTG 2050           2070           2090
            .              .              .              .
AGGTTATGTCCTTTTCCATTAAGTACATGTGCCAGGAAACAGCGAGAGAGAGAAAGTAAA 2110           2130           2150
            .              .              .              .
CGGCAGTAATGCTTCTCCTATTTCTCCAAAGCCTTGTGTGAACTAGCAAAGAGAAGAAAA 2170           2190           2210
            .              .              .              .
TCAAATATATAACCAATAGTGAAATGCCACAGGTTTGTCCACTGTCAGGGTTGTCTACCT 2230           2250           2270
            .              .              .              .
GTAGGATCAGGGTCTAAGCACCTTGGTGCTTAGCTAGAATACCACCTAATCCTTCTGGCA 2290           2310           2330
            .              .              .              .
AGCCTGTCTTCAGAGAACCCACTAGAAGCAACTAGGAAAAATCACTTGCCAAAATCCAAG 2350           2370           2390
            .              .              .              .
GCAATTCCTGATGGAAAATGCAAAAGCACATATATGTTTTAATATCTTTATGGGCTCTGT 2410           2430           2450
            .              .              .              .
TCAAGGCAGTGCTGAGAGGGAGGGGTTATAGCTTCAGGAGGGAACCAGCTTCTGATAAAC
```

```
          2470                2490                2510
           .                   .                   .
ACAATCTGCTAGGAACTTGGGAAAGGAATCAGAGAGCTGCCCTTCAGCGATTATTTAAAT 2530                2550                2570
           .                   .                   .
TGTTAAAGAATACACAATTTGGGGTATTGGGATTTTTCTCCTTTTCTCTGAGACATTCCA 2590                2610                2630
           .                   .                   .
CCATTTTAATTTTTGTAACTGCTTATTTATGTGAAAAGGGTTATTTTTACTTAGCTTAGC 2650                2670                2690
           .                   .                   .
TATGTCAGCCAATCCGATTGCCTTAGGTGAAAGAAACCACCGAAATCCCTCAGGTCCCTT 2710                2730                2750
           .                   .                   .
GGTCAGGAGCCTCTCAAGATTTTTTTTGTCAGAGGCTCCAAATAGAAAATAAGAAAAGGT 2770                2790                2810
           .                   .                   .
TTTCTTCATTCATGGCTAGAGCTAGATTTAACTCAGTTTCTAGGCACCTCAGACCAATCA 2830                2850                2870
           .                   .                   .
TCAACTACCATTCTATTCCATGTTTGCACCTGTGCATTTTCTGTTTGCCCCCATTCACTT 2890                2910                2930
           .                   .                   .
TGTCAGGAAACCTTGGCCTCTGCTAAGGTGTATTTGGTCCTTGAGAAGTGGGAGCACCCT 2950                2970                2990
           .                   .                   .
ACAGGGACACTATCACTCATGCTGGTGGCATTGTTTACAGCTAGAAAGCTGCACTGGTGC 3010                3030                3050
           .                   .                   .
TAATGCCCCTTGGGAAATGGGGCTGTGAGGAGGAGGATTATAACTTAGGCCTAGCCTCTT 3070                3090                3110
           .                   .                   .
TTAACAGCCTCTGAAATTTATCTTTTCTTCTATGGGGTCTATAAATGTATCTTATAATAA 3130                3150                3170
           .                   .                   .
AAAGGAAGGACAGGAGGAAGACAGGCAAATGTACTTCTCACCCAGTCTTCTACACAGATG 3190                3210                3230
           .                   .                   .
GAATCTCTTTGGGGCTAAGAGAAAGGTTTTATTCTATATTGCTTACCTGATCTCATGTTA 3250                3270                3290
           .                   .                   .
GGCCTAAGAGGCTTTCTCCAGGAGGATTAGCTTGGAGTTCTCTATACTCAGGTACCTCTT 3310                3330                3350
           .                   .                   .
TCAGGGTTTTCTAACCCTGACACGGACTGTGCATACTTTCCCTCATCCATGCTGTGCTGT 3370                3390                3410
           .                   .                   .
GTTATTTAATTTTTCCTGGCTAAGATCATGTCTGAATTATGTATGAAAATTATTCTATGT 3430                3450
           .                   .
TTTTATAATAAAAATAATATATCAGACATCGAAAAAAAAA

CEA-(d) (SEQ ID NO:7):

10                  30                  50
             .                   .                   .
CCGGGGGACACGCAGGGCCAACAGTCACAGCAGCCCTGACCAGAGCATTCCTGGAGCTCAAG 70                  90                 110
             .                   .                   .
   CTCTCTACAAAGAGGTGGACAGAGAAGACAGCAGAGACCATGGGACCCCCCTCAGCCCCT
                                    MetGlyProProSerAlaPro 130                 150                 170
             .                   .                   .
```

-continued

```
CCCTGCAGATTGCATGTCCCCTGGAAGGAGGTCCTGCTCACAGCCTCACTTCTAACCTTC
ProCysArgLeuHisValProTrpLysGluValLeuLeuThrAlaSerLeuLeuThrPhe 190              210              230
          .                .                .
TGGAACCCACCCACCACTGCCAAGCTCACTATTGAATCCACGCCATTCAATGTCGCAGAG
TrpAsnProProThrThrAlaLysLeuThrIleGluSerThrProPheAsnValAlaGlu 250              270              290
          .                .                .
GGGAAGGAGGTTCTTCTACTCGCCCACAACCTGCCCCAGAATCGTATTGGTTACAGCTGG
GlyLysGluValLeuLeuLeuAlaHisAsnLeuProGlnAsnArgIleGlyTyrSerTrp 310              330              350
          .                .                .
TACAAAGGCGAAAGAGTGGATGGCAACAGTCTAATTGTAGGATATGTAATAGGAACTCAA
TyrLysGlyGluArgValAspGlyAsnSerLeuIleValGlyTyrValIleGlyThrGln 370              390              410
          .                .                .
CAAGCTACCCCAGGGCCCGCATACAGTGGTCGAGAGACAATATACCCCAATGCATCCCTG
GlnAlaThrProGlyProAlaTyrSerGlyArgGluThrIleTyrProAsnAlaSerLeu 430              450              470
          .                .                .
CTGATCCAGAACGTCACCCAGAATGACACAGGATTCTACACCCTACAAGTCATAAAGTCA
LeuIleGlnAsnValThrGlnAsnAspThrGlyPheTyrThrLeuGlnValIleLysSer 490              510              530
          .                .                .
GATCTTGTGAATGAAGAAGCAACCGGACAGTTCCATGTATACCCGGAGCTGCCCAAGCCC
AspLeuValAsnGluGluAlaThrGlyGlnPheHisValTyrProGluLeuProLysPro 550              570              590
          .                .                .
TCCATCTCCAGCAACAACTCCAACCCCGTGGAGGACAAGGATGCTGTGGCCTTCACCTGT
SerIleSerSerAsnAsnSerAsnProValGluAspLysAspAlaValAlaPheThrCys 610              630              650
          .                .                .
GAACCTGAGGTTCAGAACACAACCTACCTGTGGTGGGTAAATGGTCAGAGCCTCCCGGTC
GluProGluValGlnAsnThrThrTyrLeuTrpTrpValAsnGlyGlnSerLeuProVal 670              690              710
          .                .                .
AGTCCCAGGCTGCAGCTGTCCAATGGCAACAGGACCCTCACTCTACTCAGCGTCAAAAGG
SerProArgLeuGlnLeuSerAsnGlyAsnArgThrLeuThrLeuLeuSerValLysArg 730              750              770
          .                .                .
AACGATGCAGGATCGTATGAATGTGAAATACAGAACCCAGCGAGTGCCAACCGCAGTGAC
AsnAspAlaGlySerTyrGluCysGluIleGlnAsnProAlaSerAlaAsnArgSerAsp 790              810              830
          .                .                .
CCAGTCACCCTGAATGTCCTCTATGGCCCAGATGGCCCCACCATTTCCCCCTCAAAGGCC
ProValThrLeuAsnValLeuTyrGlyProAspGlyProThrIleSerProSerLysAla 850              870              890
          .                .                .
AATTACCGTCCAGGGGAAAATCTGAACCTCTCCTGCCACGCAGCCTCTAACCCACCTGCA
AsnTyrArgProGlyGluAsnLeuAsnLeuSerCysHisAlaAlaSerAsnProProAla 910              930              950
          .                .                .
CAGTACTCTTGGTTTATCAATGGGACGTTCCAGCAATCCACACAAGAGCTCTTTATCCCC
GlnTyrSerTrpPheIleAsnGlyThrPheGlnGlnSerThrGlnGluLeuPheIlePro 970              990             1010
          .                .                .
AACATCACTGTGAATAATAGCGGATCCTATATGTGCCAAGCCCATAACTCAGCCACTGGC
AsnIleThrValAsnAsnSerGlySerTyrMetCysGlnAlaHisAsnSerAlaThrGly 1030             1050             1070
          .                .                .
CTCAATAGGACCACAGTCACGATGATCACAGTCTCTGGAAGTGCTCCTGTCCTCTCAGCT
LeuAsnArgThrThrValThrMetIleThrValSerGlySerAlaProValLeuSerAla 1090             1110             1130
          .                .                .
GTGGCCACCGTCGGCATCACGATTGGAGTGCTGGCCAGGGTGGCTCTGATATAGCAGCCC
```

-continued

ValAlaThrValGlyIleThrIleGlyValLeuAlaArgValAlaLeuIleEnd

```
         1150          1160          1170          1180          1190
          .             .             .             .             .
   TGG TGT ATT TTC GAT ATT TCA GGA AGA CTG GCA GAT TGG ACC AGA CCC TGA ATT CTT
1200          1210          1220          1230          1240          1250
  .             .             .             .             .             .
  CTA GCT CCT CCA ATC CCA TTT TAT CCC ATG GAA CCA CTA AAA ACA AGG TCT GCT CTG
         1260          1270          1280          1290          1300          1310
          .             .             .             .             .             .
   CTC CTG AAG CCC TAT ATG CTG GAG ATG GAC AAC TCA ATG AAA ATT TAA AGG AAA AAC
         1320          1330          1340          1350          1360          1370
          .             .             .             .             .             .
   CCT CAG GCC TGA GGT GTG TGC CAC TCA GAG ACT TCA CCT AAC TAG AGA CAG GCA AAC
              1380          1390          1400          1410          1420
               .             .             .             .             .
       TGC AAA CCA nnC CTC TTT CGC TTG GCA GGA TGA TGG TGT CAT TAG TAT TTC ACA AGA
1430          1440          1450          1460          1470          1480
  .             .             .             .             .             .
  AGT AGC TTC AGA GGG TAA CTT AAC AGA GTA TCA GAT CTA TCT TGT CAA TCC CAA CGT
         1490          1500          1510          1520          1530          1540
          .             .             .             .             .             .
   TTT ACA TAA AAT AAG CGA TCC TTT AGT GCA CCC AGT GAC TGA CAT TAG CAG CAT CTT
              1550          1560          1570          1580          1590
               .             .             .             .             .
       TAA CAC AGC CGT GTG TTC AAG TGT ACA GTG GTC CTT TTC AGA GTT GGn nnT ACT CCA
1600          1610          1620          1630          1640          1650
  .             .             .             .             .             .
  ACT GAA ATG TTA AGG AAG AAG ATA GAT CCA ATT AAA AAA AAT TAA AAC CAA TTT AAA
         1660          1670          1680          1690          1700          1710
          .             .             .             .             .             .
   AAA AAA AAA GAA CAC AGG AGA TTC CAG TCT ACT TGA GTT AGC ATA ATA CAG AAG TCC
              1720          1730          1740          1750          1760
               .             .             .             .             .
       CCT CTA CTT TAA CTT TTA CAA AAA AGT AAC CTG AAC TAA TCT GAT GTT AAC CAA TGT
1770          1780          1790          1800          1810          1820
  .             .             .             .             .             .
  ATT TAT TTG TCT GGT TCT GTT TCC TTG TTC CAA TTT GAC AAA ACC CAC TGT TCT TGT
         1830          1840          1850          1860          1870          1880
          .             .             .             .             .             .
   ATT GTA TTG CCC AGG GGG AGC TAT CAC TGT ACT TGT AGA GTG GTG CTG CTT TAA GTT
              1890          1900          1910          1920          1930          1940
               .             .             .             .             .             .
       CAT AAA TCA CAA ATA AAA GCC AAT TAG CTC TAT AAC TAA AAA AAA AAA AAA AAA AAA
                   1950          1960
                    .             .
           AAA AAA AAA AAA AAA AAA AAA AAA
```

Figure 1B:
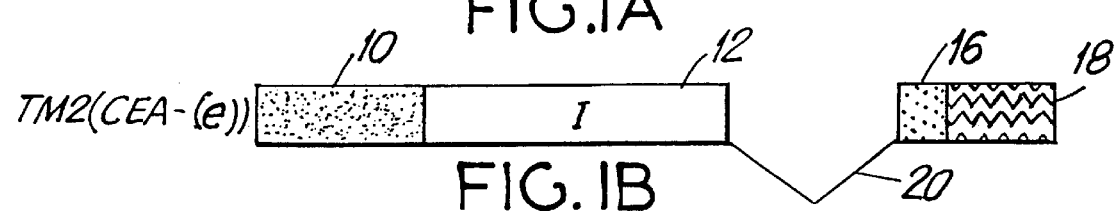
Figure 1C:
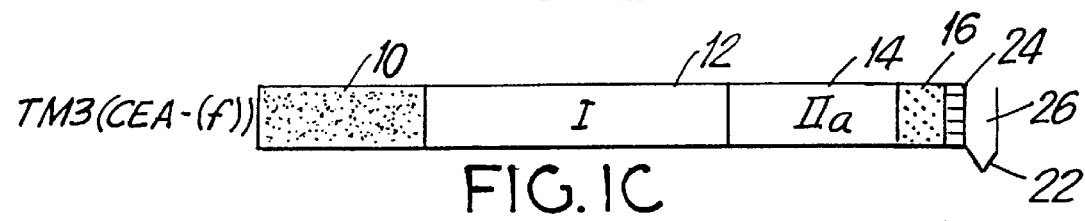
Figure 1D:
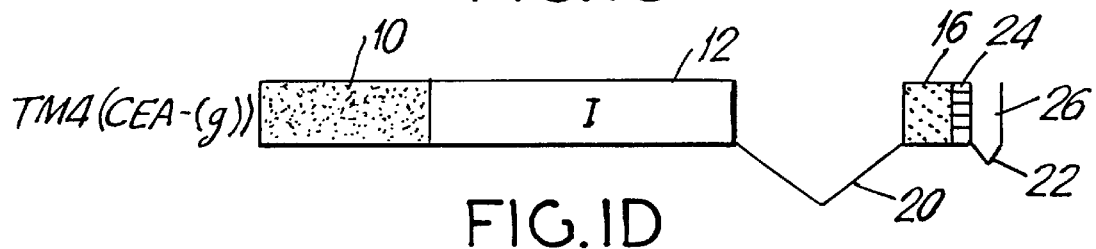

A schematic relationship of the transmembrane CEA'S, namely TM-1 (CEA-(c)), TM-2 (CEA-(e)), TM-3 (CEA-(f)) and TM-4 (CEA-(g)) is depicted in FIG. 1:

Assuming TM-1 is composed of five sections as depicted in FIG. 1, namely 10, 12, 14, 16 and 18, TM-2 differs from TM-1 in that the 100 amino acid (100 AA) section 14 is deleted and at splice point 20 betweeen sections 12 and 16, surprisingly an extra amino acid, namely Asp occurs.

TM-3 is the same as TM-1 except that section 18 is truncated at splice point 22, i.e., a section of 70 amino acids is deleted and results in a new section made up of subsections 24+26. Surprisingly, however, six new amino acids (section 26) occur. Another example of formation of a novel amino acid sequence resulting from a deletion of nucleic acid sequence is for platelet derived growth factor-A.

TM-4 is the same as TM-2 up until the end of subsection 24.

Subsection 24 is contained in section 18 of TM-1 and TM-2, but is not depicted in FIG. 1 for TM-1 and TM-2.

Some CEA epitopes are unique. These are the epitopes which have been useful for distinguishing the various CEA-like antigens immunologically. Peptide epitopes are defined by the linear amino acid sequence of the antigen and/or features resulting from protein folding. The information required for protein folding is encoded in the primary amino acid sequence. Therefore, antigenic differences ultimately result from differences in the primary structure of the different CEA molecules. The differences residing in the CEA protein in the CEA species can thus be determined by determining the primary amino acid sequences. This can be most readily accomplished by cloning and sequencing each of the genes for CEA. To determine which gene products will be most useful for cancer diagnosis, unique probes can be selected for each gene and expression of each gene can be determined in different tumor types by nucleic acid hybridization techniques. The present invention provides a tool with which to identify potential genes coding for different members of the CEA family and to determine the theoretical primary amino acid sequences for them. Using the method of automated peptide synthesis, peptides can then be synthesized corresponding to unique sequences in these antigens. With these peptides, antibodies to these sequences can be produced which, in the intact CEA molecule, might not be recognized by the animal being immunized. Having accomplished this, advantage can then be taken of the differences in these antigens to generate specific immunoassays for the measurement of each antigen.

A wide variety of host/cloning vehicle combinations may be employed in cloning the double-stranded nucleic acid prepared in accordance with this invention. For example, useful cloning vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB89 and their derivatives, wider host range plasmids, e.g., RP4, and phage DNAs, e.g., the numerous derivatives of phage, e.g., NM989, and other DNA phages, e.g., M13 and Filamenteous single-stranded DNA phages and vectors derived from combinations of plasmids and phage DNAs such as plasmids which have been modified to employ phage DNA or other expression control sequences or yeast plasmids such as the $2\mu$ plasmid or derivatives thereof. Useful hosts may include bacterial hosts such as strains of *E. coli*, such as *E. coli* HB 101, *E. coli* X1776, *E. coli* X2282, *E. coli* MRC1 and strains of Pseudomonas, *Bacillus subtilis, Bacillus stearothermophilus* and other *E. coli*, bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the nucleic acid according to the present invention. These sites are usually designated by the restriction endonuclease which cuts them. For example, in pBR322 the PstI site is located in the gene for beta-lactamase, between the nucleotide triplets that code for amino acids 181 and 182 of that protein. One of the two HindII endonuclease recognition sites is between the triplets coding for amino acids 101 and 102 and one of the several Taq sites at the triplet coding for amino acid 45 of beta-lactamase in pBR322. In similar fashion, the EcoRI site and the PVUII site in this plasmid lie outside of any coding region, the EcoRl site being located between the genes coding for resistance to tetracycline and ampicillin, respectively. These sites are well recognized by those of skill in the art. It is, of course, to be understood that a cloning vehicle useful in this invention need not have a restriction endonuclease site for insertion of the chosen DNA fragment. Instead, the vehicle could be cut and joined to the fragment by alternative means.

The vector or cloning vehicle and in particular the site chosen therein for attachment of a selected nucleic acid fragment to form a recombinant nucleic acid molecule is determined by a variety of factors, e.g., the number of sites susceptible to a particular restriction enzyme, the size of the protein to be expressed, the susceptibility of the desired protein to proteolytic degradation by host cell enzymes, the contamination of the protein to be expressed by host cell proteins difficult to remove during purification, the expression characteristics, such as the location of start and stop codons relative to the vector sequences, and other factors recognized by those of skill in the art. The choice of a vector and an insertion site for a particular gene is determined by a balance of these factors, not all sections being equally effective for a given case.

Methods of inserting nucleic acid sequences into cloning vehicles to form recombinant nucleic acid molecules include, for example, dA-dT tailing, direct ligation, synthetic linkers, exonuclease and polymerase-linked repair reactions followed by ligation, or extension of the nucleic acid strand with an appropriate polymerase and an appropriate single-stranded template followed by ligation.

It should also be understood that the nucleotide sequences or nucleic acid fragments inserted at the selected site of the cloning vehicle may include nucleotides which are not part of the actual structural gene for the desired polypeptide or mature protein or may include only a fragment of the complete structural gene for the desired protein or mature protein.

The cloning vehicle or vector containing the foreign gene is employed to transform an appropriate host so as to permit that host to replicate the foreign gene and to express the protein coded by the foreign gene or portion thereof. The selection of an appropriate host is also controlled by a number of factors recognized by the art. These include, for example, the compatibility with the chosen vector, the toxicity of proteins encoded by the hybrid plasmid, the ease of recovery of the desired protein, the expression characteristics, biosafety and costs. A balance of these factors must be struck with the understanding that not all hosts may be equally effective for expression of a particular recombinant DNA molecule.

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered nucleic acid, e.g., DNA, fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli*

("the trp system"), the major operator and promoter regions of phage λ ($O_L P_L$ and $O_R P'_R$), the control region of Filamenteous single-stranded DNA phages, or other sequences which control the expression of genes of prokaryotic or eukaryotic cells and their viruses. Therefore, to improve the production of a particular polypeptide in an appropriate host, the gene coding for that polypeptide may be selected and removed from a recombinant nucleic acid molecule containing it and reinserted into a recombinant nucleic acid molecule closer or in a more appropriate relationship to its former expression control sequence or under the control of one of the above described expression control sequences. Such methods are known in the art.

As used herein "relationship" may encompass many factors, e.g., the distance separating the expression enhancing and promoting regions of the recombinant nucleic acid molecule and the inserted nucleic acid sequence, the transcription and translation characteristics of the inserted nucleic acid sequence or other sequences in the vector itself, the particular nucleotide sequence of the inserted nucleic acid sequence and other sequences of the vector and the particular characteristics of the expression enhancing and promoting regions of the vector.

Further increases in the cellular yield of the desired products depend upon an increase in the number of genes that can be utilized in the cell. This is achieved, for illustration purposes, by insertion of recombinant nucleic acid molecules engineered into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al, "Lambdoid Phages That Simplify the Recovery of In Vitro Recombinants", *Molec. Gen. Genet.*, 150, pp. 53–61 (1977) and N. E. Murray et al, "Molecular Cloning of the DNA Ligase Gene From Bacteriophage T4", *J. Mol. Biol.*, 132, pp. 493–505 (1979)) and the recombinant DNA molecule recircularized by incubation with DNA ligase. The desired recombinant phage is then selected as before and used to lysogenize a host strain of *E. coli*.

Particularly useful λ cloning vehicles contain a temperature-sensitive mutation in the repression gene cl and suppressible mutations in gene S, the product of which is necessary for lysis of the host cell, and gene E, the product of which is major capsid protein of the virus. With this system, the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsulated it remains available for further transcription. Artificial lysis of the cells then releases the desired product in high yield.

In addition, it should be understood that the yield of polypeptides prepared in accordance with this invention may also be improved by substituting different codons for some or all of the codons of the present DNA sequences, these substituted codons coding for amino acids identical to those coded for by the codons replaced.

Finally, the activity of the polypeptides produced by the recombinant nucleic acid molecules of this invention may be improved by fragmenting, modifying or derivatizing the nucleic acid sequences or polypeptides of this invention by well-known means, without departing from the scope of this invention.

The polypeptides of the present invention include the following:

(1) the polypeptides expressed by the above described cells, (2) polypeptides prepared by synthetic means, (3) fragments of polypeptides (1) or (2) above, such fragments produced by synthesis of amino acids or by digestion or cleavage.

Regarding the synthetic peptides according to the invention, chemical synthesis of peptides is described in the following publications: S. B. H. Kent, *Biomedical Polymers*, eds. Goldberg, E. P. and Nakajima, A. (Academic Press, New York), 213–242, (1980); A. R. Mitchell, S. B. H. Kent, M. Engelhard and R. B. Merrifield, *J. Org. Chem.*, 43, 2845–2852, (1978); J. P. Tam, T.-W. Wong, M. Riemen, F. -S. Tjoeng and R.B. Merrifield, *Tet. Letters*, 4033–4036, (1979); S. Mojsov, A. R. Mitchell and R. B. Merrifield, *J. Org. Chem.*, 45, 555–560, (1980); J. P. Tam, R. D. DiMarchi and R. B. Merrifield, *Tet. Letters*, 2851–2854, (1981); and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.) 1981.

In the Merrifield solid phase procedure, the appropriate sequence of L-amino acids is built up from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure. The peptide-resin is:

(a) washed with methylene chloride;

(b) neutralized by making for 10 minutes at room temperature with 5% (v/v) diisopropylethylamine (or other hindered base) in methylene chloride;

(c) washed with methylene chloride;

(d) an amount of amino acid equal to six times the molar amount of the growing peptide chain is activated by combining it with one-half as many moles of a carbodiimide (e.g., dicyclohexylcarbodiimide, or diisopropylcarbodiimide) for ten minutes at 0° C., to form the symmetric anhydride of the amino acid. The amino acid used should be provided originally as the N-alpha-tert.-butyloxycarbonyl derivative, with side chains protected with benzyl esters (e.g., aspartic or glutamic acids), benzyl ethers (e.g., serine, threonine, cysteine or tyrosine), benzyloxycarbonyl groups (e.g., lysine) or other protecting groups commonly used in peptide synthesis;

(e) the activated amino acid is reacted with the peptide-resin for two hours at room temperature, resulting in addition of the new amino acid to the end of the growing peptide chain;

(f) the peptide-resin is washed with methylene chloride;

(g) the N-alpha-(tert.-butyloxycarbonyl) group is removed from the most recently added amino acid by reacting with 30 to 65%, preferably 50% (v/v) trifluoroacetic acid in methylene chloride for 10 to 30 minutes at room temperature;

(h) the peptide-resin is washed with methylene chloride;

(i) steps (a) through (h) are repeated until the required peptide sequence has been constructed.

The peptide is then removed from the resin and simultaneously the side-chain protecting groups are removed, by reaction with anhydrous hydrofluoric acid containing 10% v/v of anisole or other suitable (aromatic) scavenger.

Subsequently, the peptide can be purified by gel filtration, ion exchange, high pressure liquid chromatography, or other suitable means.

In some cases, chemical synthesis can be carried out without the solid phase resin, in which case the synthetic reactions are performed entirely in solution. The reactions are similar and well known in the art, and the final product is essentially identical.

Digestion of the polypeptide can be accomplished by using proteolytic enzymes, especially those enzymes whose substrate specificity results in cleavage of the polypeptide at sites immediately adjacent to the desired sequence of amino acids.

Cleavage of the polypeptide can be accomplished by chemical means. Particular bonds between amino acids can be cleaved by reaction with specific reagents. Examples include the following: bonds involving methionine are cleaved by cyanogen bromide; asparaginyl-glycine bonds are cleaved by hydroxylamine.

The present invention has the following advantages:
  (1) The nucleic acids coding for TM-1, TM-2 and TM-3 can be used as probes to isolate other members of the CEA gene family.
  (2) The nucleic acids coding for TM-1, TM-2 and TM-3 can be used to derive oligonucleotide probes to determine the expression of TM-1, TM-2, TM-3 and other CEA genes in various tumor types.
  (3) TM-1, TM-2, TM-3 and TM-4 nucleotide sequences can be used to predict the primary amino acid sequence of the protein for production of synthetic peptides.
  (4) Synthetic peptides derived from the above sequences can be used to produce sequence-specific antibodies.
  (5) Immunoassays for each member of the CEA antigen family can be produced with these sequence-specific antibodies and synthetic peptides.
  (6) The aforementioned immunoassays can be used as diagnostics for different types of cancer if it is determined that different members of the CEA family are clinically useful markers for different types of cancer.

Peptides according to the present invention can be labelled by conventional means using radioactive moieties (e.g., 5I), enzymes, dyes and fluorescent compounds, just to name a few.

Several possible configurations for immunoassays according to the present invention can be used. The readout systems capable of being employed in these assays are numerous and non-limiting examples of such systems include fluorescent and colorimetric enzyme systems, radioisotopic labelling and detection and chemiluminescent systems. Two examples of immunoassay methods are as follows:
  (1) An enzyme linked immunoassay (ELISA) using an antibody preparation according to the present invention (including Fab or F(ab)' fragments derived therefrom) to a solid phase (such as a microtiter plate or latex beads) is attached a purified antibody of a specificity other than that which is conjugated to the enzyme. This solid phase antibody is contacted with the sample containing CEA antigen family members. After washing, the solid phase antibody-antigen complex is contacted with the conjugated anti-peptide antibody (or conjugated fragment). After washing away unbound conjugate, color or fluorescence is developed by adding a chromogenic or fluorogenic substrate for the enzyme. The amount of color or fluorescence developed is proportional to the amount of antigen in the sample.
  (2) A competitive fluorometric immunoassay using fluorescently labelled peptide or synthetic peptides of the sequences for TM-2, TM-2, TM-3 and TM-4. In this example, the purified peptide expressed by cells or synthetic peptides thereof are fluorescently labelled. To a solid phase is attached a purified antibody. This solid phase is then contacted with sample containing CEA antigen family members to which has been added fluorescent peptide probe. After binding, excess probe is washed away the amount of bound probe is quantitated. The amount of bound fluorescent probe will be inversely proportional to the amount of antigen in the sample.

In the nucleic acid hybridization method according to the present invention, the nucleic acid probe is conjugated with a label, for example, an enzyme, a fluorophore, a radioisotope, a chemiluminescent compound, etc. In the most general case, the probe would be contacted with the sample and the presence of any hybridizable nucleic acid sequence would be detected by developing in the presence of a chromogenic enzyme substrate, detection of the fluorophore by epifluorescence, by autoradiography of the radioisotopically labelled probe or by chemiluminescence. The detection of hybridizable RNA sequences can be accomplished by (1) a dot blot methodology or (2) an in situ hybridization methodology. Methods for these last two techniques are described by D. Gillespie and J. Bresser, "mRNA Immobilization in NaI: Quick Blots", *Biotechniques*, 184–192, November/December 1983 and J. Lawrence and R. Singer, "Intracellular Localization of Messenger RNAs for Cytosketal Proteins", *Cell*, 45, 407–415, May 9, 1986, respectively. The readout systems can be the same as described above, e.g., enzyme labelling, radiolabelling, etc.

As stated above, the invention also relates to the use in medicine of the aforementioned complex of the invention.

The invention further provides a pharmaceutical composition containing as an active ingredient a complex of the invention in the form of a sterile and/or physiologically isotonic aqueous solution.

For parenteral administration, solutions and emulsions containing as an active ingredient the complex of the invention should be sterile and, if appropriate, blood-isotonic.

It is envisaged that the active complex will be administered perorally, parenterally (for example, intramuscularly, intraperitoneally, or intravenously), rectally or locally.

EXAMPLE 1

Preparation of cDNA in pcE22 which codes for TM2-CEA [CEA-(e)]

Example 1a
RNA Preparation

Messenger RNA was prepared by the proteinase K extraction method of J. Favolaro, R. Treisman and R. Kamen, *Methods in Enzymology*, 65, 718, Academic Press, Inc. (1980), followed by oligo dT cellulose chromatography to yield poly A+ RNA (3'-polyadenylated eukaryotic RNA containing most mRNA sequences that can be translated into polypeptides). To obtain approximately 100 $\mu$g of poly A+ RNA, approximately $3 \times 10^8$ cells of transfectant 23.411 (ATCC No. CRL 9731, deposited with the ATCC on Jun. 1, 1988), that expresses TM-1, TM-2, TM-3 and TM-4, Kamarck et al, *Proc. Natl. Acad. Sci.*, USA, 84, 5350–5354, August 1987, were harvested from roller bottles after late logarithmic growth. Cells were lysed by homogenization in an ice-cold solution of 140 mM NaCl, 1.5 mM $MgCl_2$, 10 mM Tris-NCl, pH 8.0, 0.5% NP40, 4 mM dithiothreitol and 20 units of placental ribonuclease inhibitor/ml. sodium deoxycholate was then added to 0.2%. Cytoplasm and nuclei were separated by centrifugation of the homogenate at 12,000×g for 20 minutes. The cytoplasmic fraction was mixed with an equal volume of 0.2 M Tris-HCl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obrtained by ethanol precipitation of the separated aqueous phase. Total RNA was enriched by passage in 0.5 M NaCl, 10 mM Tris-HCl, p7.8, 0.1% sarcosyl through an oligo dT(12–18) cellulose column. After washing, bound RNA was eluted in the same solution without sodium chloride.

Example 1b
Reverse Transcription of mRNA

Ten micrograms of poly A+ RNA were primed for reverse transcription with oligo dT(12–18) and pdN$_6$ printers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase II, E. coli DNA polymerase I and E. coli DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-liCl, pH 7.8, 1 mM EDTA (TE).

Example 1c
Cloning of pcE22 (plasmid cDNA E22)

```
Synthetic    5' pCCCGGG    3'     (SEQ ID NO:14)
DNA linkers  3'  GGGCCCTTAA 5'
``` were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the 23.411 cell line, the size of the CEA-related mRNA was estimated at 3.6 kb. Therefore, cDNA fragments between 2 and 4 kb were recovered from gel slices and fragments were ethanol precipitated. After resuspension of cDNA in TE, EcoRI-cleaved lambada gtl0 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained ofter in vitro packaging and infection of E. coli host NM514.

Example 1d
Screening of Recombinant Library

Five hundred thousand packaged lambda particles were plated on lawns of E. coli NM514 and replicate patterns were lifted onto nitrocellulose sheets as described by W. D. Benton and R. W. Davis, Science 196, 180–182, (1977). Positive phage were selected by hybridization with $^{32}$P-labeled L,V7 cDNA insert probe that contained a domain repeated amoung various CEA family members. By multiple rounds of screening. Phage from individual plaques were amplified and titered, and these were used to prepare small quantities of recombinant phage DNA.

Example 1e
DNA Manipulation

Phage DNA was prepared according to T. Maniatis, E. Fritsch and J. Sambrook, Molecular Cloning, A Laboratory Manual, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, Proc. Natl. Acad. Sci., U.S.A., 74, 5463–5467, (1977). The nucleic acid and translated sequence for cDNA in pcE22 is given hereinabove (TM-2 (CEA-(e)).

EXAMPLE 2

Preparation of cDNA in pcHT-6 which Particlally Codes for TM3-CEA [CEA-(f)]

Example 2a
RNA Preparation

Messenger RNA was prepared by the proteinase K extraction method of J. Favolaro, R. Treisman and R. Kamen, Methods in Enzymology, 65 718, Academic Press, Inc. (1980), followed by oligo dT cellulose chromatography to yield poly A+RNA (3'-polyadenylated eukaryotic RNA containing most mRNA sequences that can be translated into polypeptides). To obtain approximately 100 ug of poly A+ RNA, approximately 3×10$^8$ cells of IIT-29 tumor cells (ATCC HTB38) were harvested form roller bottles after late logarithmic growth. Cells were lysed by homogenization in an ice-cold solution of 140 mM NaCl, 1.5 mM MgCl$_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei were separated by centrifugation of the homogenate at 12,000×g for 20 minutes. The cytoplasmic fraction was mixed with an equal volume of 0.2 M Tris-Hcl, pH 7.8, 25 mM EDTA, 0.3 M NaCl, 2% sodium dodecyl sulfate and 400 μg/ml of proteinase K, incubated for 1 hour at 37° C., then extracted once with an equal volume of phenol/cholorform (1:1/v:v) solution. Nucleic acids were obrtained by ethanol precipitation of the separated aqueous phase. Total RNA was enriched by passage in 0.5 M NaCl, 10 mM Tris-HCl, pH 7.8, 0.1% sarcosyl through an oligo dT(12–18) cellulose column. After washing, bound RNA was eluted in the same solution without sodium chloride.

Example 2b
Reverse Transcription of mRNA

Ten micrograms of HT-29 poly A+ RNA were primed for reverse transcription with oligo dT(12–18) and pdN$_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids was replaced with the second complementary strand by treatment with RNase H, E. coli DNA polymerase I and E. coli DNA ligase at 12° C. and 22° C. for 1.5 hours each. Molecular ends were polished by treatment with T4 DNA polymerase. cDNA was phenol/chloroform extracted and purified over a "SEPHADEX G-50" spun column prepared in 10 mM Tris-HCl, pH 7.8, 1 mM EDTA (TE).

Example 2c
Cloning of pcHT-6 (plasmid cDNA HT-6)
Synthetic DNA linkers
5' pCCCGGG 3'
3' GGGCCCTTAA 5' (SEQ ID NO: 14)
were attached to the ends of cDNA by blunt end ligation with excess T4 DNA ligase. Excess linkers were removed by chromatography through "SEPHADEX G-50" (medium) in TE, and by fractionation on 0.8% low melting agarose gel. Based on Northern blot analysis of poly A+ RNA of the HT-29 cell line, the size of the CEA-related mRNA was estimated at 2.2 kb. Therefore, cDNA fragments between 2 and 3 kb were recovered from gel slices and fragments were ethanol precipitated. After resuspension of cDNA in TE, EcoRI-cleaved lambada gt10 arms were added to cDNA at an estimated molar ratio of 1:1. Ligation proceeded at 7° C. for 2 days in the presence of T4 DNA ligase. Aliquots of the ligation reaction were added to commercially-obtained packaging mix (Stratagene, San Diego, Calif., U.S.A.). Five million phage particles were obtained ofter in vitro packaging and infection of E. coli host NM514.

Example 2d

Screening of Recombinant Library

Five hundred thousand packaged lambda particles were plated on lawns of E. coli NM514 and replicate patterns were lifted onto nitrocellulose sheets as described by W. D. Benton and R. W. Davis, Science, 196, 180–182, (1977). Positive phage were selected by hybridization with ⁻P-labeled LV7 CDNA insert probe that contained a domain repeated amoung various CEA family members. By multiple rounds of screening. Phage from individual plaques were amplified and titered, and these were used to prepare small quantities of recombinant phage DNA.

Example 2e

DNA Manipulation

Phage DNA was prepared according to T. Maniatis, E. Fritsch and J. Sambrook, *Molecular Cloning, A Laboratory Manual*, Cold Spring Habor, (1982). DNA segments were isolated from low melting agarose gels and inserted for subcloning into Bluescript plasmid vectors (Stratagene, San Diego, Calif., U.S.A.). DNA sequencing was performed by the dideoxy termination method of F. Sanger, S. Nicklen and A. Coulson, *Proc. Natl. Acad. Sci.*, U.S.A., 74, 5463–5467, (1977). The nucleic acid and translated sequence for cDNA in HT-6 not complete at the 5' end of its coding region, but the nucleotide sequenece and restriction map of the HT-6 insert indicates that it is related to nucleic acid sequences of cDNA clones coding for CEA-(c) and CEA-(e). The nucleotide sequence of HT-6 insert differs from these clones at only nucleotide position 1463 to 1515 and 1676 to 2429 of the CEA-(c) cDNA. It is inferred from this result that the pcHT-6 insert is a partial coding sequence for CEA-(f) and the presumed nucleic acid and translated sequence of CEA-(f) is given hereinabove (TM-3 (CEA-(f)).

Example 3

Preparation of cDNA which codes for TM4-CEA [CEA-(g)]

Example 3a

RNA Preparation

Messenger RNA is prepared by the proteinase K extraction method of J. Favolaro, R. Treisman and R. Kamen, *Methos in Enzymology*, 65, 718, Academic Press, Inc. (1980), followed by oligo dT cellulose chromatography to yield poly A+RNA (3'-polyadenylated eukaryotic RNA containing most mRNA sequences that can be translated into polypeptides). To obtain approximately 100 ug of poly A+ RNA, approximately $3 \times 10^8$ cells of transfectant 23.411 or tumor cell line HT-29 (ATCC HTB 38) are harvested from roller bottles after late logarithmic growth. Cells are lysed by homogenization in an ice-cold solution of 140 mM NaCl, 1.5 mM $MgCl_2$, 10 mM Tris-HCl, pH 8.0, 0.5% NP40, 4 mM dithiothreitol and 20 units of placental ribonuclease inhibitor/ml. Sodium deoxycholate was then added to 0.2%. Cytoplasm and nuclei are separated by centrifugation of the homogenate at 12,000×g for 20 minutes. The cytoplasmic fraction is mixed with an equal volume of 0.2 M Tris-Hcl, pH 7.8, 25 mM EDTA, 0.3 M NaCl, 2% sodium dodecyl sulfate and 400 µg/ml of proteinase K, incubated for 1 hour at 37° C., then extracted once with an equal volume of phenol/cholorform (1:1/v:v) solution. Nucleic acids are obtained by ethanol precipitation of the separated aqueous phase. Total RNA is enriched by passage in 0.5 M NaCl, 10 mM Tris-HCl, pH 7.8, 0.1% sarcosyl through an oligo dT(12–18) cellulose column. After washing, bound RNA is eluted in the same solution without sodium chloride.

Example 3b

Reverse Transcription of mRNA

Ten micrograms of 23.411 or HT 29 poly A+RNA are primed for reverse transcription with oligo dT(12–18) and $pdN_6$ primers. One hundred microliter reaction was performed for 4 hours at 42° C. with 200 units AMV reverse transcriptase (Life Science, Inc. St. Petersburg, Fla., U.S.A.). The RNA component of the cDNA/mRNA hybrids is replaced with the second complementary strand by treatment with RNase H, E. coli DNA polymerase I and E. coli DNA ligase at 12° C. and 22° C. for 1.5 hours each. Molecular ends are polished by treatment with T4 DNA polymerase. cDNA is phenol/chloroform extracted and purified over a "SEPHADEX G-50" spun column prepared in 10 mM Tris-HCl, pH 7.8, 1 mM EDTA (TE).

Example 3c

Cloning of CDNA for CEA-(g)

Synthetic DNA linkers

5' pCCCGGG 3'

3' GGGCCCTTAA 5' (SEQ ID NO: 14)

are attached to the ends of CDNA by blunt end ligation with excess T4 DNA ligase. Excess linkers are removed by chromatography through "SEPHADEX G-50" (medium) in TE, and by fractionation on 0.8% low melting agarose gel. Based on Northern blot analysis of poly A+ RNA of the 23.411 and HT-29 cell lines, the size of the CEA-related mRNA is estimated at 1.7 kb. Therefore, CDNA fragments between 1 and 2 kb are recovered from gel slices and fragments are ethanol precipitated. After resuspension of cDNA in TE, EcoRI-cleaved lambda gt10 arms are added to cDNA at an estimated molar ratio of 1:1. Ligation proceeds at 7° C. for 2 days in the presence of T4 DNA ligase. Aliquots of the ligation reaction are added to commercially-obtained packaging mix (Stratagene, San Diego, Calif., U.S.A.). Phage particles are obtained after in vitro packaging and infection of E. coli host NM514.

Example 3d

Screening of Recombinant Library

Five hundred thousand to one million packaged lambda particles are plated on lawns of E. coli NM514 and replicate patterns are lifted onto nitrocellulose sheets as described by W. D. Benton and R. W. Davis, Science, 196, 180–182, (1977). Positive phage are selected by hybridization with $^{32}$P-labeled LV7 cDNA insert probe that contained a domain repeated amoung various CEA family members. By this selection method, positive phage are obtained after multiple rounds of screening. Phage from individual plaques are amplified and titered, and these are used to prepare small quantities of recombinant phage DNA.

Example 3e

DNA Manipulation

Phage DNA is prepared according to T. Maniatis, E. Fritsch and J. Sambrook, *Molecular Cloning, A Laboratory Manual*, Cold Spring Harbor, (1982). DNA segments are isolated from low melting agarose gels and inserted for subcloning into Bluescript plasmid vectors (Stratagene, San Diego, Calif., U.S.A.). DNA sequencing is performed by the dideoxy termination method of F. Sanger, S. Nicklen and A. Coulson, *Proc. Natl. Acad. Sci., U.S.A.*, 74, 5463–5467, (1977). The nucleotide and translated sequence for a cDNA coding for CEA-(g) is given hereinabove (TM-4 (CEA-(g)).

Example 4

Screening of a KG-1 cDNA Library with $^{32}$P-labelled CEA Probe, LV7 (CEA-(A))

A segment of cDNA coding for a portion of carcinoembryonic antigen [LV7 or CEA-(a)] was radiolabelled by random priming and used to detect homologous sequences on filter replicas of a commercial cDNA library prepared from KG-1 cells in bacteriophage vector λ gt11 (Clontech Laboratories, Inc., Palo Alto, Calif., U.S.A.). Hybridizations were performed at 68° C. in 2xSSSPE (1xSSPE—0.15 M NaCl, 0.01 M sodium phosphate and 1 mM EDTA, pH 7), 5xDenhardt's solution and 100 μg of denatured salmon sperm DNA per ml, and post-hybridization washes were in 0.2xSSC, 0.25% sodium dodecyl sulfate.

Positive phage were picked, rescreened to homogeneity, and amplified for production of DNA. cDNA inserts were excised from phage DNA with EcoRI endonuclease and subcloned into the EcoRI site of the plasmid vector pBluescript KS. DNA sequencing on double-stranded DNA was by the method of Sanger et al, supra. The sequences of two different inserts from the KG-1 cDNA library are shown below:

```
pcKGCEA1 (SEQ ID NO:8):

1 acagcacagctgacagccgtactcaggaagcttctggatcctaggcttatctccacagag    60

61 gagaacacacaagcagcagagaccatggggcccctctcagccctccctgcacacacctc   120
                                 MetGlyProLeuSerAlaProProCysThrHisLeu 121 atcacttggaaggggtcctgctcacagcatcacttttaaacttctggaatccgcccaca   180
     IleThrTrpLysGlyValLeuLeuThrAlaSerLeuLeuAsnPheTrpAsnProProThr 181 actgcccaagtcacgattgaagcccagccacccaaagtttctgaggggaaggatgttctt   240
     ThrAlaGlnValThrIleGluAlaGlnProProLysValSerGluGlyLysAspValLeu 241 ctacttgtccacaatttgccccagaatcttgctggctacatttggtacaaagggcaaatg   300
     LeuLeuValHisAsnLeuProGlnAsnLeuAlaGlyTyrIleTrpTyrLysGlyGlnMet 301 acatacgtctaccattacattacatcatatgtagtagacggtcaaagaattatatatggg   360
     ThrTyrValTyrHisTyrIleThrSerTyrValValAspGlyGlnArgIleIleTyrGly 361 cctgcatacagtggaagagaaagagtatattccaatgcatccctgctgatccagaatgtc   420
     ProAlaTyrSerGlyArgGluArgValTyrSerAsnAlaSerLeuLeuIleGlnAsnVal 421 acgcaggaggatgcaggatcctacaccttacacatcataaagcgacgcgatgggactgga   480
     ThrGlnGluAspAlaGlySerTyrThrLeuHisIleIleLysArgArgAspGlyThrGly 481 ggagtaactggacatttcaccttcacccttacacctggagactcccaagccctccatctcc   540
     GlyValThrGlyHisPheThrPheThrLeuHisLeuGluThrProLysProSerIleSer 541 agcagcaacttaaatcccaggaggccatggaggctgtgatcttaacctgtgatcctgcg   600
     SerSerAsnLeuAsnProArgGluAlaMetGluAlaValIleLeuThrCysAspProAla 601 actccagccgcaagctaccagtggtggatgaatggtcagagcctccctatgactcacagg   660
     ThrProAlaAlaSerTyrGlnTrpTrpMetAsnGlyGlnSerLeuProMetThrHisArg 661 ttgcagctgtccaaaaccaacaggaccctctttatatttggtgtcacaaagtatattgca   720
     LeuGlnLeuSerLysThrAsnArgThrLeuPheIlePheGlyValThrLysTyrIleAla 721 ggaccctatgaatgtgaaatacggaacccagtgagtgccagccgcagtgacccagtcacc   780
     GlyProTyrGluCysGluIleArgAsnProValSerAlaSerArgSerAspProValThr 781 ctgaatctcctcccaaagctgtccaagccctacatcacaatcaacaacttaaacccaga   840
     LeuAsnLeuLeuProLysLeuSerLysProTyrIleThrIleAsnAsnLeuAsnProArg 841 gagaataaggatgtcttaaccttcacctgtgaacctaagagtgagaactacacctacatt   900
     GluAsnLysAspValLeuThrPheThrCysGluProLysSerGluAsnTyrThrTyrIle 901 tggtggctaaatggtcagagcctccctgtcagtcccagggtaaagcgacccattgaaaac   960
     TrpTrpLeuAsnGlyGlnSerLeuProValSerProArgValLysArgProIleGluAsn 961 aggatcctcattctacccaatgtcacgagaaatgaaacaggaccttatcaatgtgaaata  1020
     ArgIleLeuIleLeuProAsnValThrArgAsnGluThrGlyProTyrGlnCysGluIle 1021 cgggaccgatatggtggcatccgcagtgacccagtcaccctgaatgtcctctatggtcca  1080
     ArgAspArgTyrGlyGlyIleArgSerAspProValThrLeuAsnValLeuTyrGlyPro 1081 gacctcccagcatttaccttcattcacctattaccgttcaggagaaaacctctacttt   1140
     AspLeuProSerIleTyrProSerPheThrTyrTyrArgSerGlyGluAsnLeuTyrPhe 1141 tcctgcttcggtgagtctaacccacgggcacaatattcttggacaattaatgggaagttt  1200
     SerCysPheGlyGluSerAsnProArgAlaGlnTyrSerTrpThrIleAsnGlyLysPhe 1201 cagctatcaggacaaaagctctctatcccccaataactacaaagcatagtgggctctat  1260
     GlnLeuSerGlyGlnLysLeuSerIleProGlnIleThrThrLysHisSerGlyLeuTyr 1261 gcttgctctgttcgtaactcagccactggcaaggaaagctccaaatccatcacagtcaaa  1320
     AlaCysSerValArgAsnSerAlaThrGlyLysGluSerSerLysSerIleThrValLys
```

-continued

```
1321  gtctctgactggatattaccctgaattctactagttcctccaattccattttctcccatg  1380
      ValSerAspTrpIleLeuProEnd 1381  gaatcacgaagagcaagacccactctgttccagaagccctataatctggaggtggacaac  1440

1441  tcgatgtaaatttcatgggaaaaccttgtacctgacatgtgagccactcagaactcacc   1500

1501  aaaatgttcgacaccataacaacagctactcaaactgtaaaccaggataagaagttgatg  1560

1561  acttcacactgtggacagtttttcaaagatgtcataacaagactccccatcatgacaagg  1620

1621  ctccaccctctactgtctgctcatgcctgcctctttcacttggcaggataatgcagtcat  1680

1681  tagaatttcacatgtagtagcttctgagggtaacaacagagtgtcagatatgtcatctca  1740

1741  acctcaaacttttacgtaacatctcagggaaatgtggctctctccatcttgcatacaggg  1800

1801  ctcccaatagaaatgaacacagagatattgcctgtgtgtttgcagagaagatggtttcta  1860

1861  taaagagtaggaaagctgaaattatagtagagtctcctttaaatgcacattgtgtggatg  1920

1921  gctctcaccatttcctaagagatacagtgtaaaaacgtgacagtaatactgattctagca  1980

1981  gaataaacatgtaccacatttgcaaaaaa                                  2010
``` pcKGCEA2 (SEQ ID NO:9):

```
   1  gggtggatcctaggctcatctccataggggagaacacacatacagcagagaccatggga   59
                                                              MetGly 60  cccctctcagcccctcctgcactcagcacatcacctggaaggggctcctgctcacagca   119
      ProLeuSerAlaProProCysThrGlnHisIleThrTrpLysGlyLeuLeuLeuThrAla 120  tcacttttaaacttctggaacctgcccaccactgcccaagtaataattgaagcccagcca  179
      SerLeuLeuAsnPheTrpAsnLeuProThrThrAlaGlnValIleIleGluAlaGlnPro 180  cccaaagtttctgagggaaggatgttcttctacttgtccacaatttgccccagaatctt   239
      ProLysValSerGluGlyLysAspValLeuLeuLeuValHisAsnLeuProGlnAsnLeu 240  actggctacatctggtacaaagggcaaatgacggacctctaccattacattacatcatat  299
      ThrGlyTyrIleTrpTyrLysGlyGlnMetThrAspLeuTyrHisTyrIleThrSerTyr 300  gtagtagacggtcaaattatatatgggcctgcctacagtggacgagaaacagtatattcc  359
      ValValAspGlyGlnIleIleTyrGlyProAlaTyrSerGlyArgGluThrValTyrSer 360  aatgcatccctgctgatccagaatgtcacacaggaggatgcaggatcctacaccttacac  419
      AsnAlaSerLeuLeuIleGlnAsnValThrGlnGluAspAlaGlySerTyrThrLeuHis 420  atcataaagcgaggcgatgggactggaggagtaactggatatttcactgtcaccttatac  479
      IleIleLysArgGlyAspGlyThrGlyGlyValThrGlyTyrPheThrValThrLeuTyr 480  tcggagactcccaagcgctccatctccagcagcaacttaaaccccagggaggtcatggag  539
      SerGluThrProLysArgSerIleSerSerSerAsnLeuAsnProArgGluValMetGlu 540  gctgtgcgcttaatctgtgatcctgagactccggatgcaagctacctgtggttgctgaat  599
      AlaValArgLeuIleCysAspProGluThrProAspAlaSerTyrLeuTrpLeuLeuAsn 600  ggtcagaacctcccctatgactcacaggttgcagctgtccaaaaccaacaggaccctctat  659
      GlyGlnAsnLeuProMetThrHisArgLeuGlnLeuSerLysThrAsnArgThrLeuTyr 660  ctatttggtgtcacaaagtatattgcagggccctatgaatgtgaaatacggaggggagtg  719
      LeuPheGlyValThrLysTyrIleAlaGlyProTyrGluCysGluIleArgArgGlyVal 720  agtgccagccgcagtgacccagtcaccctgaatctcctcccgaagctgcccatgccttac  779
      SerAlaSerArgSerAspProValThrLeuAsnLeuLeuProLysLeuProMetProTyr 780  atcaccatcaacaacttaaaccccagggagaagaaggatgtgttagccttcacctgtgaa  839
      IleThrIleAsnAsnLeuAsnProArgGluLysLysAspValLeuAlaPheThrCysGlu 840  cctaagagtcggaactacacctacatttggtggctaaatggtcagagcctcccggtcagt  899
      ProLysSerArgAsnTyrThrTyrIleTrpTrpLeuAsnGlyGlnSerLeuProValSer 900  ccgagggtaaagcgacccattgaaaacaggatactcattctacccagtgtcacgagaaat  959
      ProArgValLysArgProIleGluAsnArgIleLeuIleLeuProSerValThrArgAsn 960  gaaacaggaccctatcaatgtgaaatacgggaccgatatggtggcatccgcagtaaccca  1019
      GluThrGlyProTyrGlnCysGluIleArgAspArgTyrGlyGlyIleArgSerAsnPro 1020  gtcaccctgaatgtcctctatggtccagacctccccagaatttaccccttacttccacctat  1079
      ValThrLeuAsnValLeuTyrGlyProAspLeuProArgIleTyrProTyrPheThrTyr
```

-continued

```
1080  taccgttcaggagaaaacctcgacttgtcctgctttgcggactctaacccaccggcagag  1139
      TyrArgSerGlyGluAsnLeuAspLeuSerCysPheAlaAspSerAsnProProAlaGlu 1140  tattttggacaattaatgggaagtttcagctatcaggacaaaagctctttatcccccaa  1199
      TyrPheTrpThrIleAsnGlyLysPheGlnLeuSerGlyGlnLysLeuPheIleProGln 1200  attactacaaatcatagcgggctctatgcttgctctgttcgtaactcagccactggcaag  1259
      IleThrThrAsnHisSerGlyLeuTyrAlaCysSerValArgAsnSerAlaThrGlyLys 1260  gaaatctccaaatccatgatagtcaaagtctctggtccctgccatggaaaccagacagag  1319
      GluIleSerLysSerMetIleValLysValSerGlyProCysHisGlyAsnGlnThrGlu 1320  tctcattaatggctgccacaatagagacactgagaaaaagaacaggttgataccttcatg  1379
      SerHisEnd 1380  aaattcaagacaaagaagaaaaaggctcaatgttattggactaaataatcaaaaggataa  1439

1440  tgttttcataattttattggaaaatgtgctgattcttggaatgttttattctccagatt  1499

1500  tatgaacttttttcttcagcaattggtaaagtatactttgtaaacaaaaattgaaaca  1559

1560  tttgcttttgctctctatctgagtgccccccc  1591
```

It will be appreciated that the instant specification and claims are set forth by way of illustration and not limitation and that various modifications and changes may be made without departing from the spirit and scope of the present invention.

---

What is claimed is:

1. An isolated and purified antibody preparation that specifically binds to a unique determinant of a polypeptide selected from the group consisting of the polypeptides encoded by the cDNA sequences TM-2 (SEQ ID NO.: 1), TM-3 (SEQ ID NO.: 2), KGCEA-1 (SEQ ID NO.: 8) and KGCEA-2 (SEQ ID NO.: 9).

2. An immunoassay method for detecting a carcinoembryonic antigen family member in a test sample comprising the steps of contacting the test sample with an antibody preparation according to claim 1 and determining binding thereof to said carcinoembryonic antigen family member in the sample.

* * * * *